(12) United States Patent
Kavash et al.

(10) Patent No.: US 8,354,556 B2
(45) Date of Patent: Jan. 15, 2013

(54) PROCESSES FOR PREPARING A POLYMERIC COMPOUND

(75) Inventors: Robert W. Kavash, Radnor, PA (US); Haizhong Tang, Radnor, PA (US); Carol Mulrooney, Radnor, PA (US); Dahui Liu, Radnor, PA (US)

(73) Assignee: PolyMedix, Inc., Radnor, PA (US)

( * ) Notice: Subject to any disclaimer, the term of this patent is extended or adjusted under 35 U.S.C. 154(b) by 268 days.

(21) Appl. No.: 12/908,977

(22) Filed: Oct. 21, 2010

(65) Prior Publication Data

US 2011/0098498 A1 Apr. 28, 2011

Related U.S. Application Data

(60) Provisional application No. 61/253,975, filed on Oct. 22, 2009.

(51) Int. Cl.
C07C 233/65 (2006.01)
C07C 229/44 (2006.01)
(52) U.S. Cl. .................... 564/153; 560/45; 562/442
(58) Field of Classification Search .............. 560/45; 562/442; 564/153
See application file for complete search history.

(56) References Cited

U.S. PATENT DOCUMENTS

| 4,011,386 | A | 3/1977 | Matsumoto et al. | |
|---|---|---|---|---|
| 7,858,737 | B2* | 12/2010 | Gellman et al. | 530/300 |
| 2003/0181753 | A1 | 9/2003 | Groger et al. | |
| 2003/0212113 | A1 | 11/2003 | Dyatkina et al. | |
| 2005/0107307 | A1 | 5/2005 | Bernadini et al. | |
| 2006/0024264 | A1 | 2/2006 | Kuroda et al. | |
| 2006/0041024 | A1* | 2/2006 | Shaker | 514/616 |
| 2009/0239811 | A1 | 9/2009 | Shaker | |

FOREIGN PATENT DOCUMENTS

| WO | 97/49413 | 12/1997 |
|---|---|---|
| WO | 02/100295 | 12/2002 |
| WO | 2006/021001 | 2/2006 |

OTHER PUBLICATIONS

Konig, et al., [A new method for synthesis of peptides: activation of the carboxyl group with dicyclohexylcarbodiimide using 1-hydroxybenzotriazoles as additives], Chem Ber. 1970;103(3):788-98.
Greene, et al., Protective Groups in Organic Synthesis, 2d. Ed., Wiley & Sons, 1991.
Smith et al., Acyclic Diene Metathesis (ADMET) Polymerization Design and Synthesis of Unsaturated Poly (carbosiloxane)s, Macromolecules, 1993, 26, 1633-1642.
Bew, et al, Hybrid Caliz[4]arenes via Ionic Hydrogenation and Transition-Metal-Mediated Process, Organic Letters, May 15, 2009;11(12):2483-2486.
Heylin, Chemistry Grads Post Gains in 2005, C&ENews, Jul. 24, 2006, pp. 43-52.
Debono et al., Antibiotics That Inhibit Fungal Cell Wall Development, 1994, Ann. Rev. Microbiol. 48:471-497.
Bastian et al., Human a-defensin 1 (HNP-1) inhibits adenoviral infection in vitro, 2001, Regulatory Peptides 15:157-161.

Andersen et al., Lactoferricin and cyclic lactoferricin inhibit the entry of human cytomegalovirus into human fibroblasts, 2001, Antiviral Res. 51:141-149.
Delucca et al., Antifungal Peptides: Novel Therapeutic Compounds against Emerging Pathogens, 1999, Antimicrob. Agents and Chemother. 43(1):1-11.
Egal et al., Antiviral effects of synthetic membrane-active peptides on Herpes Simplex Virus, Type 1,1999, Int. J. Antimicrob. Agents 13:57-60.
Belaid et al., In Vitro Antiviral Activity of Dermaseptins Against Herpes Simplex Virus Type 1, 2002, J. Med. Virol. 66:229-234.
Liu et al., De Novo Design, Synthesis, and Characterization of Antimicrobial lJ-Peptides, 2001, J. Amer. Chem. Soc. 123:7553-7559.
Tew et al., De novo design of b 5114 omimetic antimicrobial polymers, 2002, Proc. Natl. Acad. Sci. USA 99(8):5110.
Delefuente et al., Homopolymerization of Methyl MEthacrylate and Styrene: Determination of the Chain-Transfer Constant from the Mayo Equation and the Number Distribution for n-Dodecanethiol, 2000, J. Polymer Sci.: Part A: Polymer Chemistry 38:170-178.
Henriquez et al., Thiols as chain transfer agents in free radical polymerization in aqueous solut Polymer 44:5559-5561 on, 2003. Sanda et al., Synthesis and Reactions of a Poly(methacrylate) from an Optically Active Amino Alcohol, 1998, J. Polymer Sci.: Part A: Polymer Chemistry 36:1981-1986.
Braun, et al., Polymer Synthesis: Theory and Practice, 3rd ed. Springer-Verlag, Berlin.
Turpie, Pharmacology of the low-molecular-we ght heparins, 1998, Am. Heart J. 135:S329-S335.
Mayo, Chain Transfer in the Polymerization of Styrene: The Reaction of Solvents with Free Radicals, 1943, J. Am. Chem. Soc. 65:2324-2329.
Hirsh et al., Low Molecular Weight Heparin, 1992, Blood 79(1):1-17.
Wakefield et al., A [+18RGD] Protamine Variant for Nontoxic and Effective Reversal of Conventional Heparin and Low-Molecular-Weight Heparin Anticoagulation, 1996, J. Surg. Res. 63:280-286.
Cole et al., Retrocyclin: A primate peptide that protects cells from infection by T- and M-tropic strains of HIV-1, 2002, Proc. Natl. Acad. Sci. USA 99(4):1813-1818.

(Continued)

Primary Examiner — Shailendra Kumar
(74) Attorney, Agent, or Firm — Pepper Hamilton LLP

(57) ABSTRACT

The present invention provides methods for preparing a polymeric compound of Formula I:

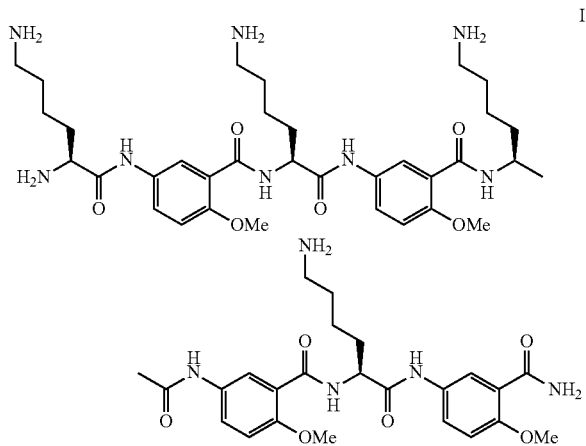

or pharmaceutically acceptable salt thereof. The present invention also provides useful intermediates for preparing the compound of Formula I or pharmaceutically acceptable salt thereof.

23 Claims, No Drawings

OTHER PUBLICATIONS

Edwards et al., In Vitro Antibacterial Activity of SM-7338, a Carbapenum Antibiotic with Stability to Dehydropeptidase 1,1989, Antimicrob. Agents & Chemotherapy 33(2):215-222.

Broekaert et al., An automated quantitative assay for fungal growth inhibition, 1990, FEMS Microbiol. Lett. 69:55-60.

Kuroda et al., Amphiphilic Polymethacrylate Derivatives as Antimicrobial Agents, 2005, J. Amer. Chem. Soc. 127:4128-4129.

Javadpour et al., De Novo Antimicrobial Peptides with Low Mammalian Cell Toxicity, 1996, J. Med. Chem. 39:3107-3113.

Kandrotas et al., Heparin Pharmacokinetics and Pharmacodynamics, 1996, Clin. Pharmacokinet 22(5):359-374.

Diness et al., Neutralization of a Low Molecular Weight-Heparin (LHN-1) and Conventional Heparin by Protamine Sulfate in Rats, 1986, Thrombosis and Haemostasis 56(3):318-322.

Wong et al., Nonpeptide Factor Xa Inhibitors: 1. Studies with SF303 and SK549, a New Class of Potent Antithrombotics, 2000, J. Pharm. Exp. Therap. 292(1):351-357.

Ryn-McKenna et al., Neutralization of Enoxaparine-Induced Bleeding by Protamine Sulfate, 1990, Thrombosis and Haemostasis 63(2):271-274.

Banker et al., Modern Pharmaceutics, Marcel Dekker, Inc. 1979 (TOC).

Goodman and Gilman's The Pharmaceutical Basis of Therapeutics, 6"1 ed., MacMillan Publishing Co., New York, 1980 (TOC).

Andreu et al., Animal Antimicrobial Peptides: An Overview, 1998, Biopolymers Peptide Science 47(6):415-433.

Fernandez-Lopez et al., Antibacterial agents based on the cyclic D,L-a-peptide architecture, 2001, Nature 412:452-455.

Patch et al., Helical Peptoid Mimics of Magainin-2 Amide, 2003, J. Am. Chem. Soc. 125:12092-12093.

Liu et al., Nontoxic membrane-Active Antimicrobial Arylamide Oligomers, 2004, Chem. Int. Edit. 43:1158-1162.

Tashiro, Antibacterial and Bacterium Absorbing Macromolecules, 2001, Macromolecular Mat. and Eng. 286:63-87.

Worley et al., Biocidal Polymers, 1996, Trends in Polymer Science 4(11):364-370.

Stiriba et al., Dendritic Polymers in Biomedical Applications: From Potential to Clinical Use in Diagnostics and Therapy, 2002, Angew. Chem. Int. Ed. 41(8):1329-1334.

Lim et al., Review of Chitosan and Its Derivatives as Antimicrobial Agents and Their Uses as Textile Chemicals, 2003, J. Macromolecular Science-Polymer Reviews C43(2):223-269.

Thorsteinsson et al., Soft Antibacterial Agents, 2003, Current Medicinal Chemistry 10:1129-1136.

Vogelberg et al., In Vitro Toxicity of Polyheranide (PHMB), 1994, Investigative Ophthalmology & Visual Science-Annual Meeting Abstract Issue 35(4):1337:373-8.

Albert et al., Structure-Activity Relationships of Oligoguanidines-Influence of Counterion, Diamine, and Average Molecular Weight on Biocidal Activities, 2003, Biomacromolecules 4:1811-1817.

Messick et al., In-vitro activity of polyhexamethylene biguanide (PHMB) against fungal isolates associated with infective keratitis, 1999, J. Antimicrob. Chemother. 44:297-298.

Hiraki et al., Use of ADME studies to confirm the safety of 6-polylysine as a preservative in food, 2003, Regulatory Toxicology and Pharmacology 37:328-340.

Pavlikova, et al., Quantitative Relationships Between Structure, Aggregation Propert Activity of Quaternary Ammonium Bolaamphiphiles, 1995, Collect. Czech. Chem. Comn es and Antimicrobial nun. 60:1213-1228.

Li et al., Study of Pyridinium-Type Functional Polymers. II. Antibacterial Activity of Soluble Pyridinium-Type Polymers, 1998, J. Appl. Polym. Sci. 67:1761-1768.

Rowden et al., In Vitro Corneal Endothelial Toxicity of PHMB, 1997, Investigative Ophthalmology & Visual Science: Abstract Book-Part III 38(4):5135-B642.

Liu et al., In Vitro Susceptibility of Ocular Bacterial and Fungal Pathogens to Polyhexamethylene Biguanide, 1996, Investigative Ophthalmology & Visual Science: Abstract Book 37(3):S876:4058-B844.

Shima et al., Antimicrobial Action of e-Poly-L-Lysine, 1984, J. Antibiot. 37(11):1449-1455.

Gelman et al., Biocidal Activity of Polystyrenes that are Cationic by Virtue of Protonat on, 2004, Organic Letters 6 (4):557-560.

Arnt et al., Nonhemolytic Abiogenic Polymers as Antimicrobial Peptide Mimics, 2004, J. Polymer Science Part A-Polymer Chemistry 42: 3860-3864.

Kiessling et al., Synthesis and Applications of Bioactive Polymers Generated by Ring-Opening Metathesis Polymerization, Handbook of Metathesis, Grubbs ed., Wiley-VCH: Weinheim, 2003, vol. 3:180-225.

Trnka et al., The Development of L2X2Ru-CHR Olefin Metathesis Catalysts: An Organometallic Success Story, 2001, Ace. Chem. Res. 34:18-29.

Buchmeiser, Homogenous Metathesis Polymerization by Well-Defined Group VI and Group VIII Transition-Metal Alkylidenes: Fundamentals and Applications in the Preparation of Advanced Materials, 2000, Chem. Rev. 100:1565-1604.

Maynard et al., Synthesis of Norbornenyl Polymers with Bioactive Oligopeptides by Ring-Opening Meththesis Polymerization, 2000, Macromolecules 33:6239-6248.

Watson et al., DNA-Block Copolymer Conjugates, J. Am. Chem. Soc. 123:5592-5593.

Mortell et al., Synthesis of Cell Agglutination Inhibitors by Aqueous Ring-Opening Metathesis Polymerization, 1994, J. Am. Chem. Soc. 116:12053-12054.

Mortell et al., Recognition Specificity of Neoglycopolymers Prepared by Ring-Opening Metathesis Polymerization, 1996, J. Am. Chem. Soc. 118:2297-2298.

Meier et al., Carbohydrate analogue polymers by ring opening metathesis polymerization (ROMP) and subsequent catalytic dihydroxylation, 2001, Chem. Commun. 9:855-856.

Watson et al., Communications to the Editor, 2001, Macromolecules 34(11):3507-3509.

Ilker etal., Modular Norbornene Derivatives for the Preparation of Well-Defined Amphiphilic Polymers: Study of the Lipid Membrane Disruption Activities, 2004, Macromolecules 37:694-700.

Arimoto et al., Multi-valent polymer of vancomycin: enhanced antibacterial activity against VRE, 1999, Chem. Commun. 1361-1362.

Love et al., A Practical and Highly Active Ruthenium-Based Catalyst that Effects the Cross Metathesis of Acrylonitrile, 2002, Angew. Chem. Int. Edit. 41 (21 ):4035-4037.

Wolfert et al., Polyelectrolyte Vectors for Gene Delivery: Influence of Cationic Polymer on Biophysical Properties of Complexes Formed with DNA, 1999, Bioconjugate Chemistry 10:993-1004.

Helmerhorst et al., A critical comparison of the hemolytic and fungicidal activities of cationic antimicrobial peptides, 1999, N. FEBS Lett. 449:105-110.

Frenzel et al., Ruthenium-Based Metathesis Initiators: Development and Use in Ring-Opening Metathesis Polymerization, 2002, J. Polymer Science Part A-Polymer Chemistry 40:2895-2916.

Biagini, et al., Synthesis of penicillin derived polymers utilizing ring-opening metathesis polymerization methodology, 1997, Chem. Commun. 12:1097-1098.

Ilker et al., Alternating Copolymerizations of Polar and Nonpolar Cyclic Olefins by Ring-Opening Metathesis Polymerization, 2002, Macromolecules 35:54-58.

Zasloff, Antimicrobial peptides of multicellular organisms, 2002, Nature 415:389-395.

Hancock, Host Defence (Cationic) Peptides—What is Their Future Clinical Potential?. 1999, Drugs 57(4):469-473.

Van'Thof et al., Antimicrobial Peptides: Properties and Applicability, 2001, Biol. Chem. 382:597-619.

Oren et al., Mode of Action of Linear Amphipathic a-Helical Antimicrobial Peptides, 1998, Biopolymers 47:451-463.

Huang, Action of Antimicrobial Peptides: Two-State Model, 2000, Biochemistry 39(29):8347-8352.

Oren, et al., Selective Lysis of Bacteria but Not Mammalian Cells by Diastereomers of Melittin: Structure-Function Study, 1997, Biochemistry 36:1862-1835.

Wade et al., All-D amino acid-containing channel-forming antibiotic peptides, 1990, Proc. Natl. Acad. Sci. USA 87:4761-4765.

Dathe et al., Peptide Helicity and Membrane Surface Charge Modulate the Balance of Electrostatic and Hydrophobic Interactions with Lipid Bilayers and Biological Membranes, 1996, Biochemistry 35:12612-12622.

Porter et al., Non-haemolytic P-amino-acid oligomers, 2000, Nature 404:565.

Porter et al., Erratum: Non-haemolytic P-amino-acid oligomers, 2000, Nature 405:298 (orig. article in Nature, 2000, 404: 565).

Raguse et al., Structure-Activity Studies of 14-Helical Antimicrobial B-Peptides: Probing the Relationship between Conformational Stability and Antimicrobial Potency, 2002, J. Am. Chem. Soc. 124:12774-12785.

Schmitt et al., Unexpected Relationships between Structure and Function in a P-Pep des: Antimicrobial Foldamers with Heterogeneous Backbones, 2004, J. Am. Chem. Soc. 126:6848-6849.

Gruzensky, et al., The use of a cecropin analog, Hecate, against Acanthamoeba in vitro. Invest Ophthalmol Vis Sci. 1994;35(Suppl):Abstract: 1337.

Osterblad, et al., Antimicrobial resistance levels of enterobacteria isolated from minced meat, J Antimicrob Chemother. Aug. 1999;44(2):298-9.

Kenawy, et al., Biologically Active Polymers, 6a Synthesis and Antimicrobial Activity of Some Linear Copolymers with Quaternary Ammonium and Phosphonium Groups, Macromol Biosci., 2003;3(2):107-116.

Limmertink, et al., Morphology Control of Organometallic Domains in Phase-Separated Poly(styrene-blockferrocenyldimethylsilanes), J. of Polymer Science, Jul. 20, 1998;36(12):Abstract 2147.

Non-Final Office Action for co-pending U.S. Appl. No. 11/206,378 dated Jan. 13, 2009.

Final Office Action for co-pending U.S. Appl. No. 11/206,378 dated Nov. 4, 2009.

Non-Final Office Action for co-pending U.S. Appl. No. 11/206,378 dated Aug. 24, 2010.

Advisory Action for co-pending U.S. Appl. No. 11/206,378 dated Jan. 15, 2010.

Final Office Action for co-pending U.S. Appl. No. 11/206,378 dated Jan. 11, 2011.

Final Office Action for related U.S. Appl. No. 11/206,378 dated May 11, 2012.

Non-Final Office Action for co-pending U.S. Appl. No. 11/206,378 dated Oct. 19, 2011.

* cited by examiner

PROCESSES FOR PREPARING A POLYMERIC COMPOUND

This application claims benefit of 61/253,975, filed Oct. 22, 2009.

REFERENCE TO GOVERNMENT GRANTS

The present invention was supported, in part, by funds from the U.S. Government (SBIR Phase 1 grant No. 1R43HL090113-01) and the U.S. Government may therefore have certain rights in the invention.

FIELD OF THE INVENTION

The present invention is directed, in part, to methods for preparing a polymeric salicylamide compound and/or pharmaceutically acceptable salts thereof, as well as to useful intermediates for the preparation of the polymeric salicylamide compound and/or pharmaceutically acceptable salts thereof.

BACKGROUND OF THE INVENTION

The polymeric salicylamide compound of Formula I:

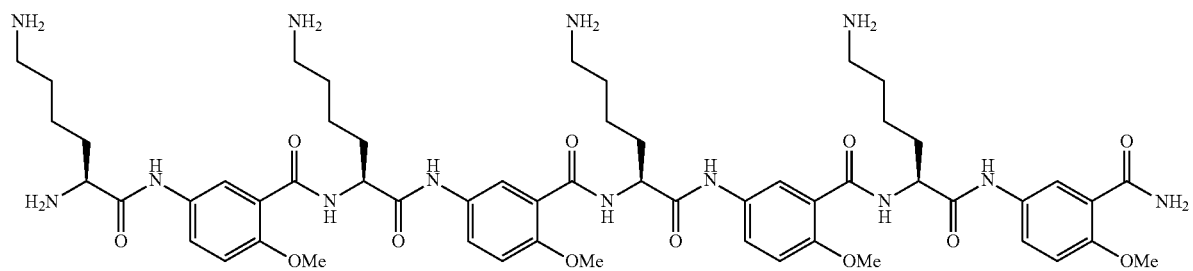

and/or pharmaceutically acceptable salts thereof are useful, for example, as pharmaceutical agents for inhibiting angiogenesis (see, WO 2005/123660). Given the importance of the compound of Formula I and/or pharmaceutically acceptable salts thereof as pharmaceutical agents, effective synthetic methods for preparing the compound and its pharmaceutically acceptable salts is of great import. This invention is directed to this, as well as other, important ends.

SUMMARY OF THE INVENTION

The present invention provides, in part, methods for preparing a compound of Formula I:

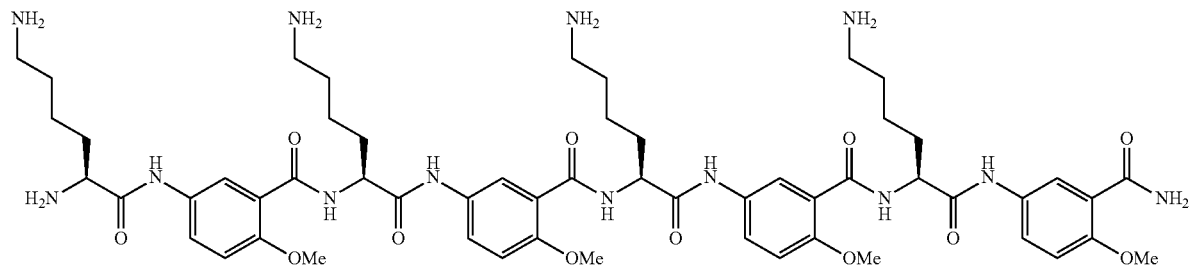

or pharmaceutically acceptable salt thereof, comprising:
a) removing the Cbz groups from a compound of Formula II:

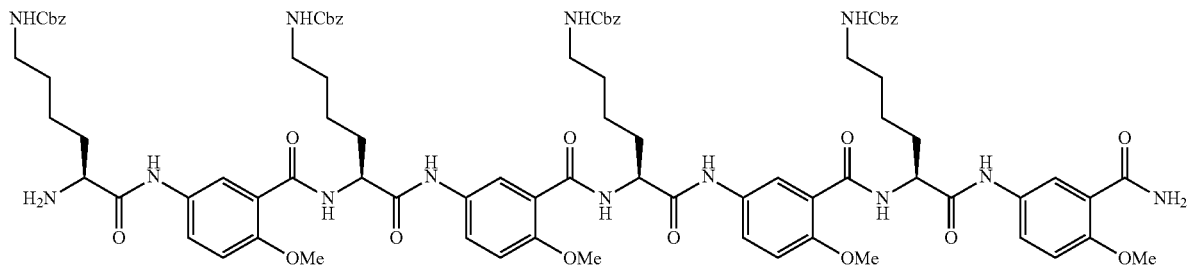

II or pharmaceutically acceptable salt thereof, under a hydrogenation/hydrogenolysis condition to form the compound of Formula I, or pharmaceutically acceptable salt thereof; and
b) optionally isolating the compound of Formula I, or pharmaceutically acceptable salt thereof.

In some embodiments, the hydrogenation/hydrogenolysis condition comprises using a metal catalyst. In some embodiments, the metal catalyst is Pd/C. In some embodiments, the reaction yield in step a) is greater than about 85%.

In some embodiments, the methods further comprise:
c) removing the Boc group from a compound of Formula III:

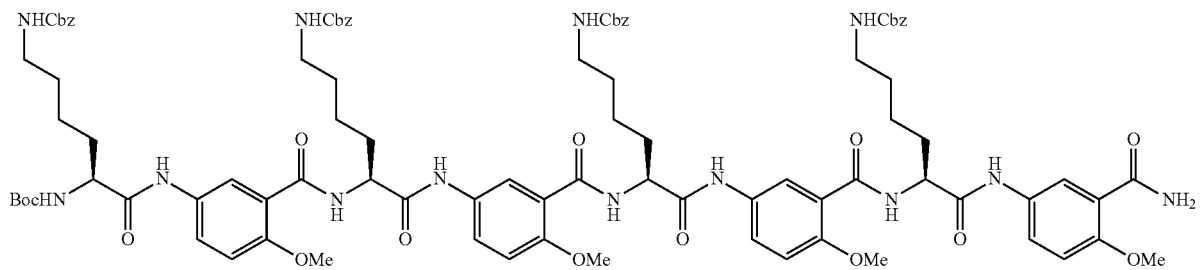

III or pharmaceutically acceptable salt thereof, in the presence of an acid to form the compound of Formula II, or pharmaceutically acceptable salt thereof.

In some embodiments, the acid is H$_3$PO$_4$. In some embodiments, the reaction yield in step c) is greater than about 85%.

In some embodiments, the methods further comprise:
d) reacting a compound of Formula IV:

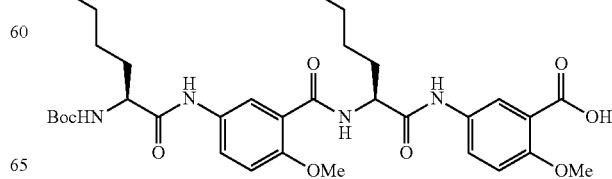

IV or pharmaceutically acceptable salt thereof, with a compound of Formula V:

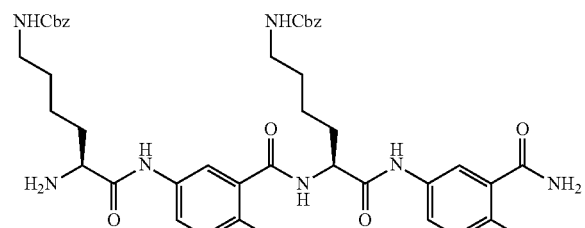

or pharmaceutically acceptable salt thereof, in the presence of a coupling reagent and an organic base to form the compound of Formula III, or pharmaceutically acceptable salt thereof.

In some embodiments, the coupling reagent is a mixture of 1-ethyl-3-(3-dimethylaminopropyl)carbodiimide and N-hydroxybenzotriazole, and wherein the organic base is N-methylmorpholine.

In some embodiments, the methods further comprise:

e) reacting a compound of Formula IV:

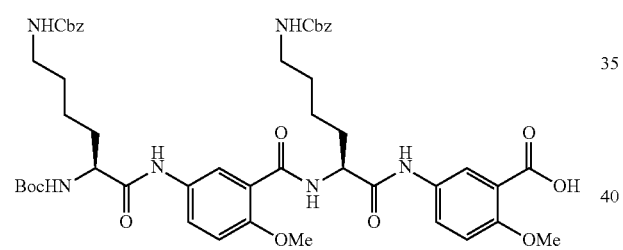

or pharmaceutically acceptable salt thereof, with ammonia or an ammonia producing reagent, in the presence of an activating reagent and an organic base to form a compound of Formula VI:

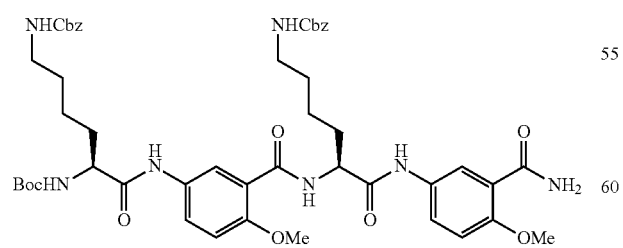

or pharmaceutically acceptable salt thereof; and f) removing the Boc group from the compound of Formula VI, or pharmaceutically acceptable salt thereof, in the presence of an acid to form the compound of Formula V, or pharmaceutically acceptable salt thereof.

In some embodiments, the activating reagent is ethyl chloroformate and the organic base is diisopropylethylamine; and wherein the acid comprises trifluoroacetic acid.

In some embodiments, the methods further comprise:

g) hydrolyzing a compound of Formula VII:

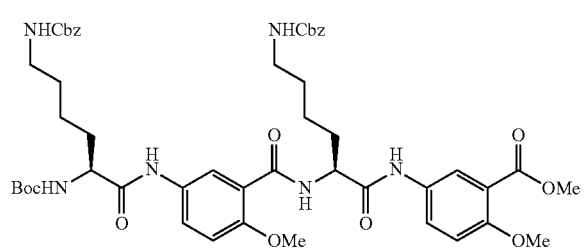

or pharmaceutically acceptable salt thereof, in the presence of a base to form the compound of Formula IV.

In some embodiments, the base is LiOH.

In some embodiments, the methods further comprise:

h) reacting a compound of Formula VIII:

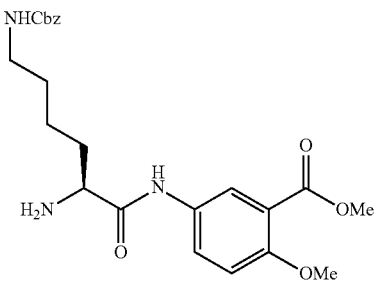

or pharmaceutically acceptable salt thereof, with a compound of Formula IX:

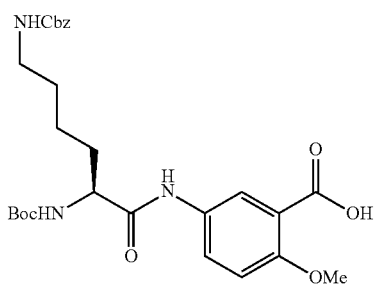

or pharmaceutically acceptable salt thereof, in the presence of a coupling reagent and an organic base to form the compound of Formula VII, or pharmaceutically acceptable salt thereof.

In some embodiments, the coupling reagent is a mixture of 1-ethyl-3-(3-dimethylaminopropyl)carbodiimide and N-hydroxybenzotriazole; and wherein the organic base is N-methylmorpholine.

In some embodiments, the methods further comprise:

i) hydrolyzing a compound of Formula X:

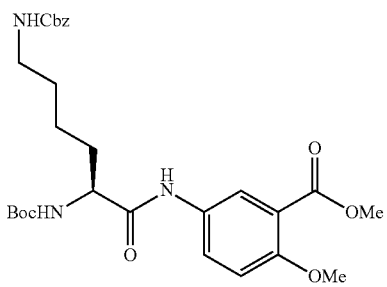

X or pharmaceutically acceptable salt thereof, in the presence of a base to form the compound of Formula IX; and j) removing the Boc group from a compound of Formula X, or pharmaceutically acceptable salt thereof, in the presence of an acid to form the compound of Formula VIII, or pharmaceutically acceptable salt thereof.

In some embodiments, the base is LiOH, and the acid is TsOH.

In some embodiments, the methods further comprise:
k) reacting a compound of Formula XI:

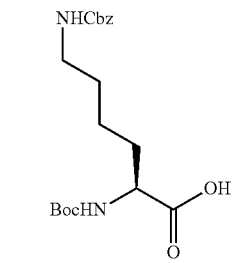

XI or pharmaceutically acceptable salt thereof, with a compound of Formula XII:

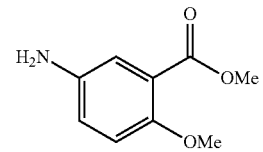

XII or pharmaceutically acceptable salt thereof, in the presence of a coupling reagent and an organic base to form the compound of Formula X, or pharmaceutically acceptable salt thereof.

In some embodiments, the coupling reagent is a mixture of 1-ethyl-3-(3-dimethylaminopropyl)carbodiimide and N-hydroxybenzotriazole; and wherein the organic base is N-methylmorpholine.

The present invention also provides, in part, methods for preparing a compound of formula I:

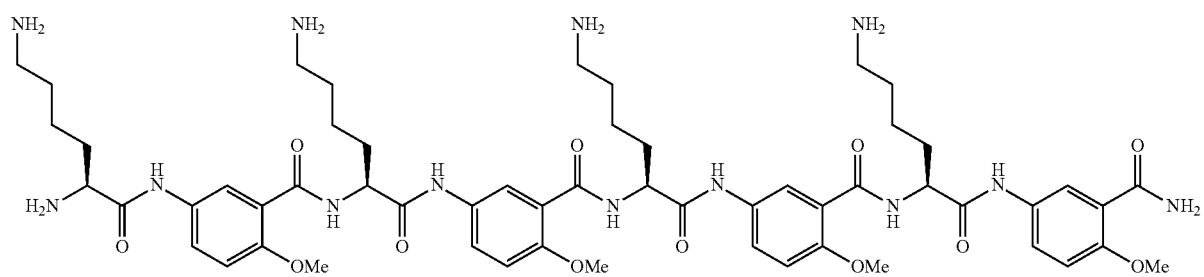

I or pharmaceutically acceptable salt thereof, comprising:
a1) removing the Cbz groups from a compound of Formula II-1:

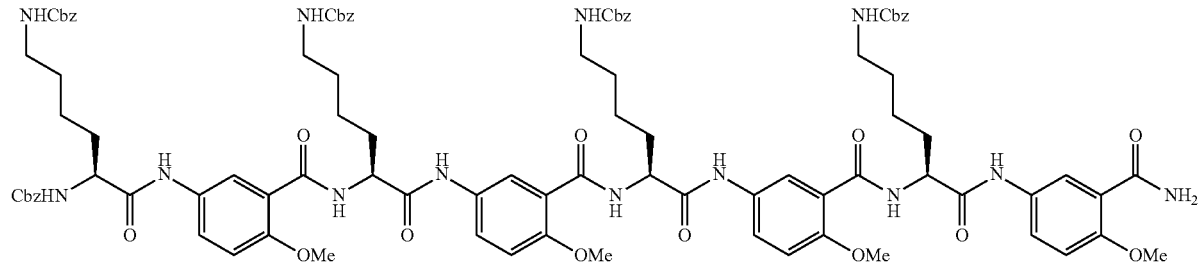

or pharmaceutically acceptable salt thereof, under a hydrogenation/hydrogenolysis condition to form the compound of Formula I, or pharmaceutically acceptable salt thereof; and
b1) optionally isolating the compound of Formula I, or pharmaceutically acceptable salt thereof.

In some embodiments, the hydrogenation/hydrogenolysis condition comprises using a metal catalyst. In some embodiments, the metal catalyst is Pd/C. In some embodiments, the reaction yield in step a1) is greater than about 85%.

In some embodiments, the methods further comprise:
c1) reacting a compound of Formula III-1:

or pharmaceutically acceptable salt thereof, with a compound of Formula IV-1:

or pharmaceutically acceptable salt thereof, in the presence of a coupling reagent and an organic base to form the compound of Formula II-1, or pharmaceutically acceptable salt thereof.

In some embodiments, the coupling reagent is a mixture of 1-ethyl-3-(3-dimethylaminopropyl)carbodiimide and N-hydroxybenzotriazole; and wherein the organic base is N-methylmorpholine.

In some embodiments, the methods further comprise:
d1) reacting a compound of Formula VI-1:

or pharmaceutically acceptable salt thereof, with a compound of Formula VII-1:

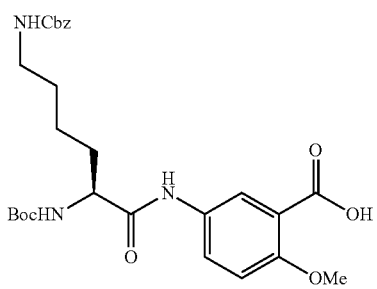

VII-1 or pharmaceutically acceptable salt thereof, in the presence of a coupling reagent and an organic base to form a compound of Formula V-1:

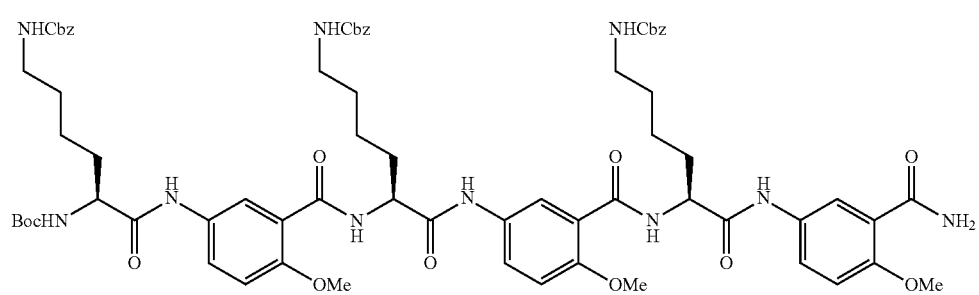

V-1 or pharmaceutically acceptable salt thereof; and e1) removing the Boc group from the compound of Formula V-1, or pharmaceutically acceptable salt thereof, in the presence of an acid to form the compound of Formula III-1, or pharmaceutically acceptable salt thereof.

In some embodiments, the coupling reagent is a mixture of 1-ethyl-3-(3-dimethylaminopropyl)carbodiimide and N-hydroxybenzotriazole, the organic base is N-methylmorpholine, and the acid is $H_3PO_4$.

In some embodiments, the methods further comprise:

f1) reacting a compound of Formula VIII-1:

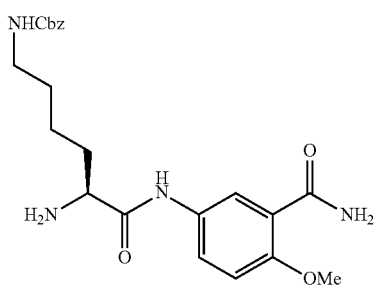

VIII-1 or pharmaceutically acceptable salt thereof, with a compound of Formula VII-1:

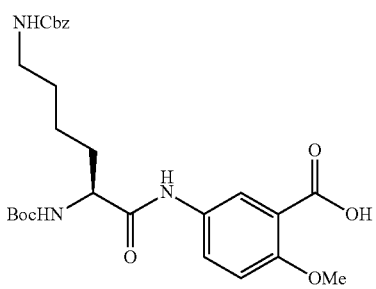

VII-1 or pharmaceutically acceptable salt thereof, in the presence of a coupling reagent and an organic base to form a compound of Formula IX-1:

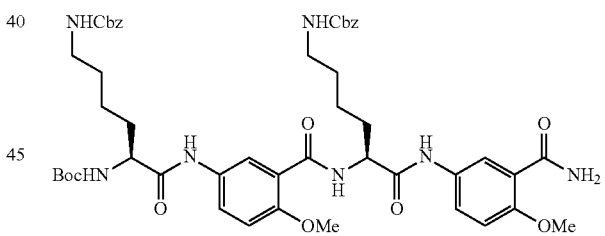

IX-1 or pharmaceutically acceptable salt thereof; and g1) removing the Boc group from the compound of Formula IX-1, or pharmaceutically acceptable salt thereof, in the presence of an acid to form the compound of Formula VI-1, or pharmaceutically acceptable salt thereof.

In some embodiments, the coupling reagent is a mixture of 1-ethyl-3-(3-dimethylaminopropyl)carbodiimide and N-hydroxybenzotriazole, the organic base is N-methylmorpholine, and the acid is $H_3PO_4$.

In some embodiments, the methods further comprise:

h1) reacting a compound of Formula XI-1:

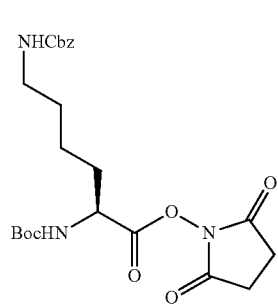

XI-1 or pharmaceutically acceptable salt thereof, with a compound of Formula XII-1:

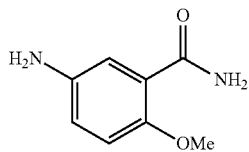

XII-1 or pharmaceutically acceptable salt thereof, optionally in the presence of an organic base to form a compound of Formula X-1:

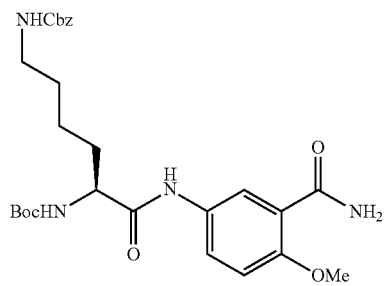

X-1 or pharmaceutically acceptable salt thereof; and i1) removing the Boc group from the compound of Formula X-1 or pharmaceutically acceptable salt thereof, in the presence of an acid to form the compound of Formula VIII-1, or pharmaceutically acceptable salt thereof.

In some embodiments, the organic base, if present, comprises N—N-dimethylaminopyridine, and the acid is hydrochloric acid.

In some embodiments, the methods further comprise:

j1) reacting a compound of Formula XI-1:

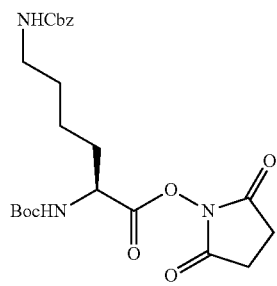

XI-1 or pharmaceutically acceptable salt thereof, with a compound of Formula XIII-1:

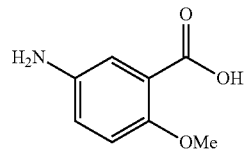

XIII-1 or pharmaceutically acceptable salt thereof, to form the compound of Formula VII-1, or pharmaceutically acceptable salt thereof.

In some embodiments, the methods further comprise:

k1) reacting a compound of Formula XIV-1:

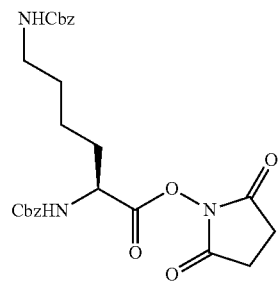

XIV-1 or pharmaceutically acceptable salt thereof, with a compound of Formula XIII-1:

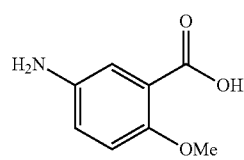

XIII-1 or pharmaceutically acceptable salt thereof, to form the compound of Formula IV-1, or pharmaceutically acceptable salt thereof.

In some embodiments, the methods further comprise:
c2) reacting a compound of Formula III-2:

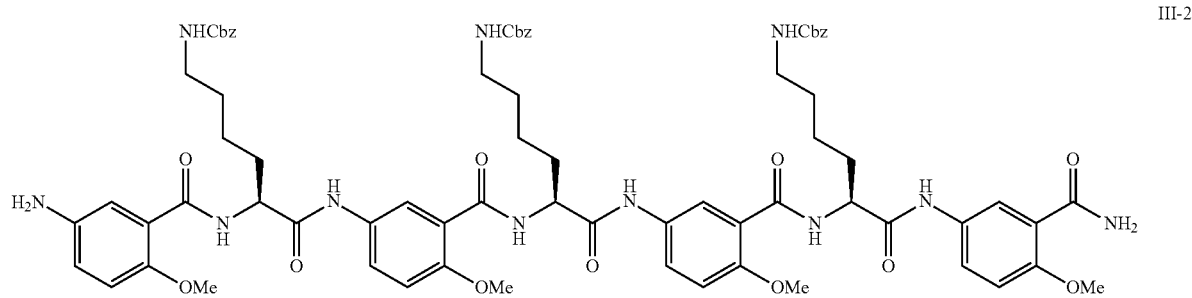 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)[C@H](CCCCNC(=O)OCc4ccccc4)NC(=O)c4cc(N)ccc4OC)ccc3OC)ccc2OC)cc1C(N)=O]

or pharmaceutically acceptable salt thereof, with a compound of Formula IV-2:

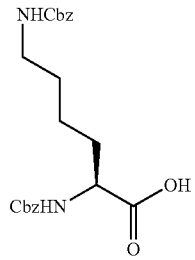

or pharmaceutically acceptable salt thereof, in the presence of a coupling reagent and an organic base to form the compound of Formula II-1, or pharmaceutically acceptable salt thereof.

In some embodiments, the coupling reagent is 2-chloro-4,6-dimethoxy-1,3,5-triazine, and the organic base is N-methylmorpholine.

In some embodiments, the methods further comprise:

d2) removing the Boc group from a compound of Formula V-2:

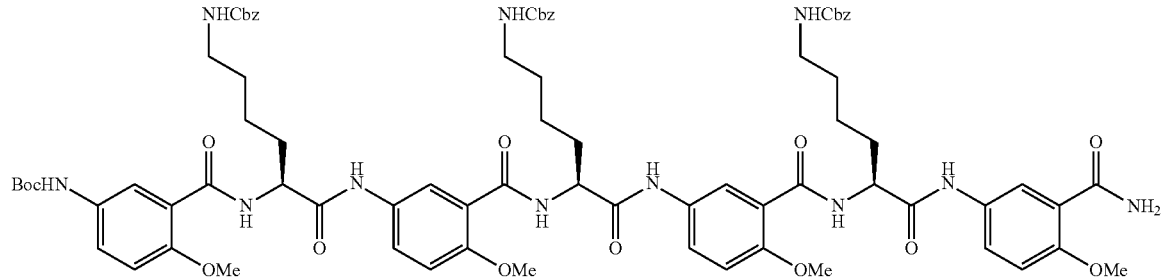

or pharmaceutically acceptable salt thereof, under an acidic condition to form the compound of Formula III-2, or pharmaceutically acceptable salt thereof.

In some embodiments, the acidic condition comprises using HCl.

In some embodiments, the methods further comprise:

e2) reacting a compound of Formula VI-2:

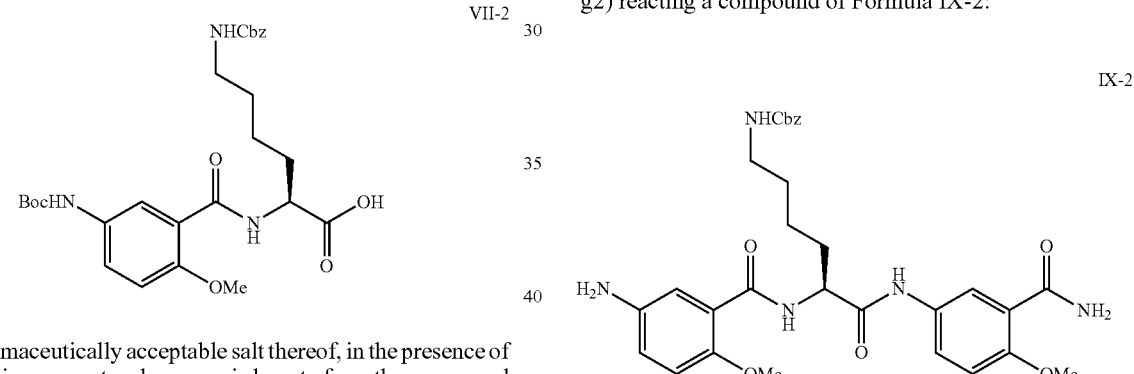

VI-2 or pharmaceutically acceptable salt thereof, with a compound of Formula VII-2:

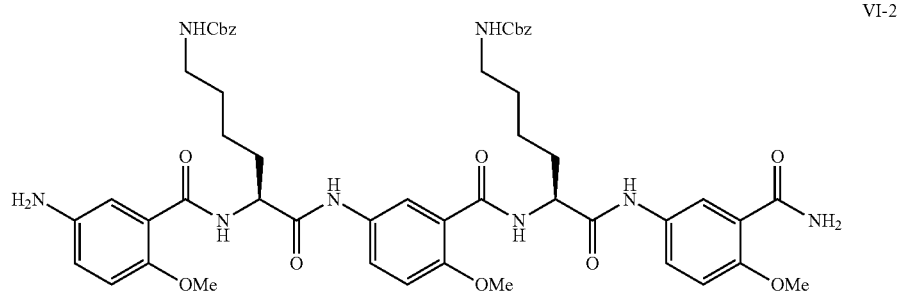 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(N)ccc3OC)ccc2OC)cc1C(N)=O]

VII-2 or pharmaceutically acceptable salt thereof, in the presence of a coupling reagent and an organic base to form the compound of Formula V-2, or pharmaceutically acceptable salt thereof.

In some embodiments, the coupling reagent is 2-chloro-4,6-dimethoxy-1,3,5-triazine, and the organic base is N-methylmorpholine.

In some embodiments, the methods further comprise:

f2) removing the Boc group from a compound of Formula VIII-2:

or pharmaceutically acceptable salt thereof, under an acidic condition to form the compound of Formula VI-2, or pharmaceutically acceptable salt thereof.

In some embodiments, the acidic condition comprises using HCl.

In some embodiments, the methods further comprise:

g2) reacting a compound of Formula IX-2:

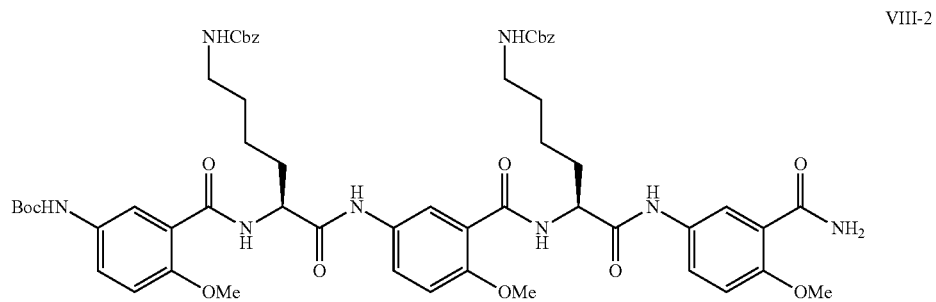 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)OC(C)(C)C)ccc3OC)ccc2OC)cc1C(N)=O]

IX-2 or pharmaceutically acceptable salt thereof, with a compound of Formula VII-2:

VIII-2

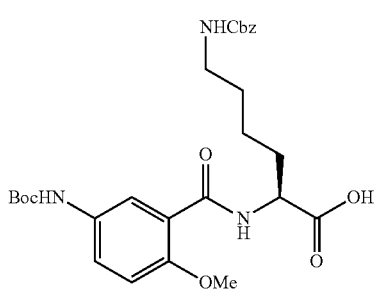

or pharmaceutically acceptable salt thereof, in the presence of a coupling reagent and an organic base to form the compound of Formula VIII-2, or pharmaceutically acceptable salt thereof.

In some embodiments, the coupling reagent is 2-chloro-4,6-dimethoxy-1,3,5-triazine, and the organic base is N-methylmorpholine.

In some embodiments, the methods further comprise:

h2) removing the Boc group from a compound of Formula X-2:

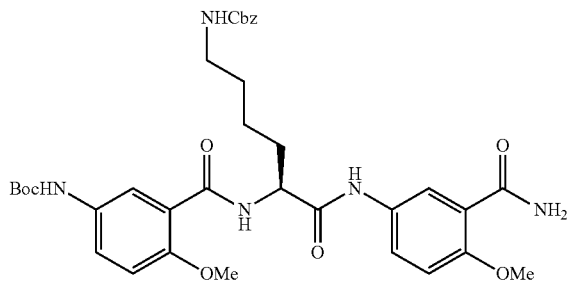

or pharmaceutically acceptable salt thereof, under an acidic condition to form the compound of Formula IX-2, or pharmaceutically acceptable salt thereof.

In some embodiments, the acidic condition comprises using HCl.

In some embodiments, the methods further comprise:

i2) reacting a compound of Formula VII-2:

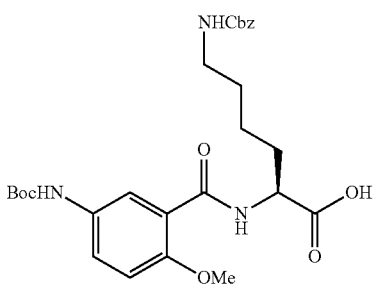

or pharmaceutically acceptable salt thereof, with a compound of Formula XI-2:

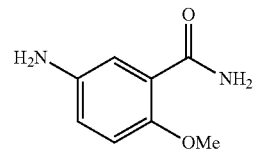

or pharmaceutically acceptable salt thereof, in the presence of a coupling reagent and an organic base to form the compound of Formula X-2, or pharmaceutically acceptable salt thereof.

In some embodiments, the coupling reagent is 2-chloro-4,6-dimethoxy-1,3,5-triazine, and the organic base is N-methylmorpholine.

The present invention also provides, in part, one or more compounds chosen from:

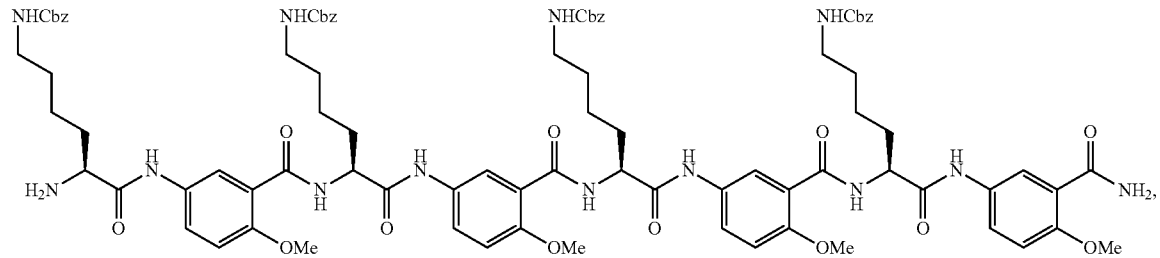

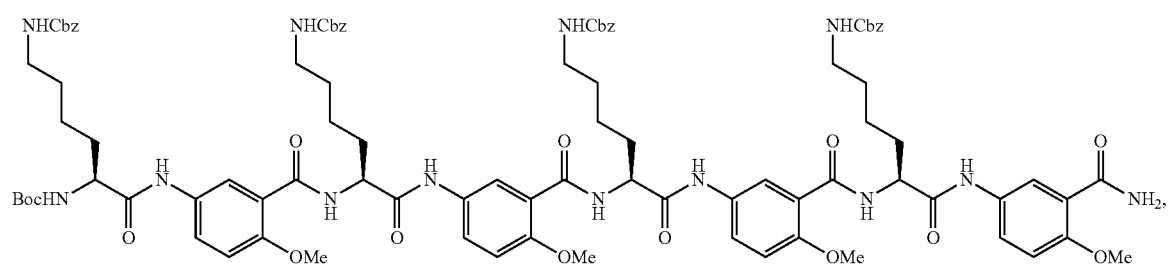

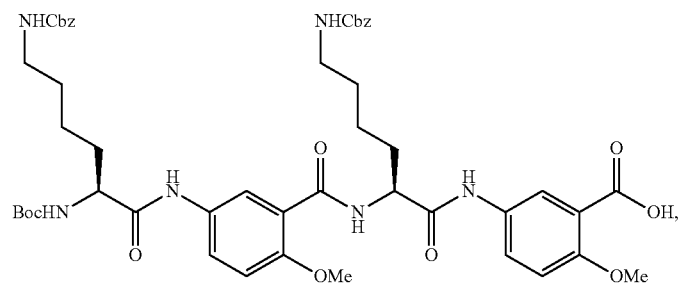
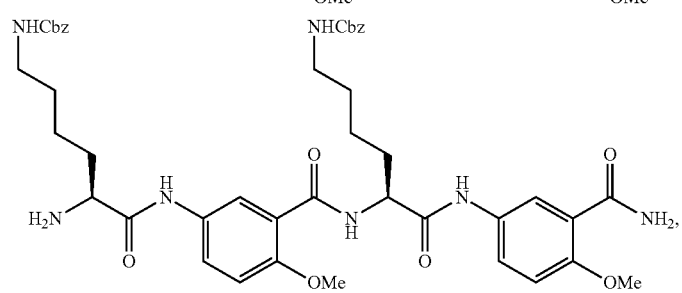
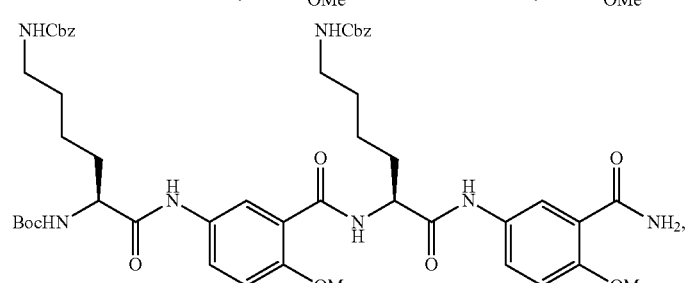
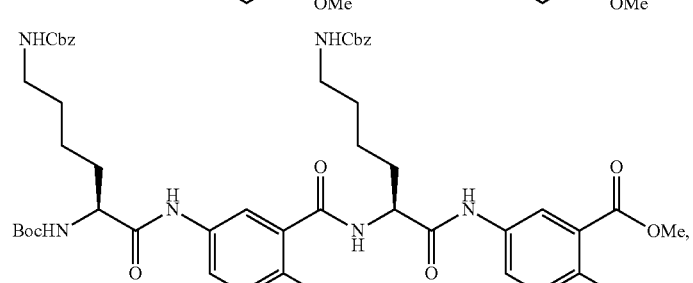
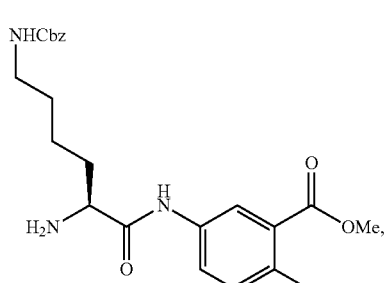
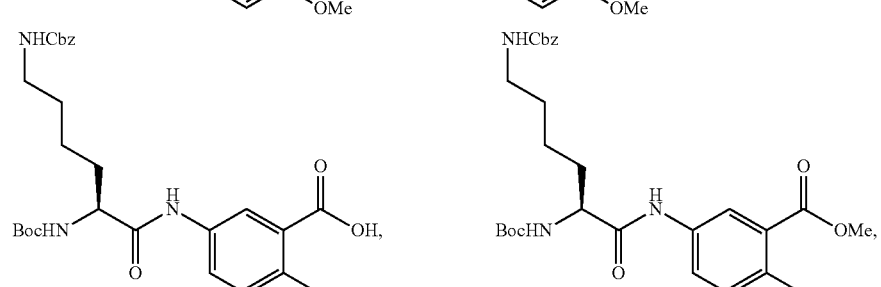
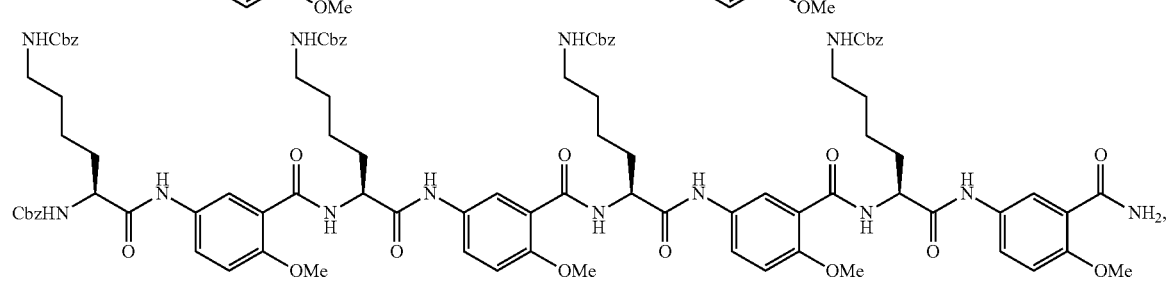

-continued
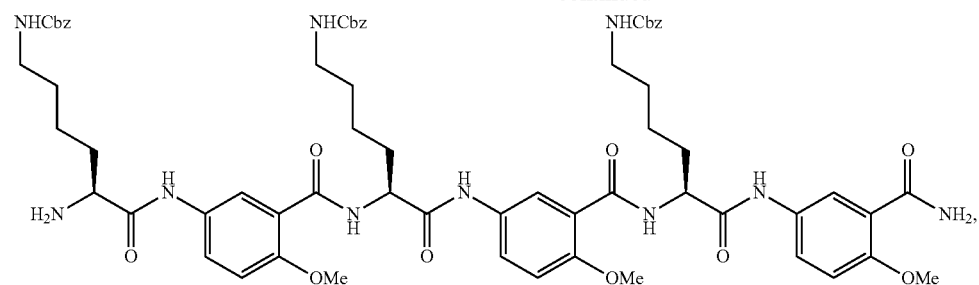
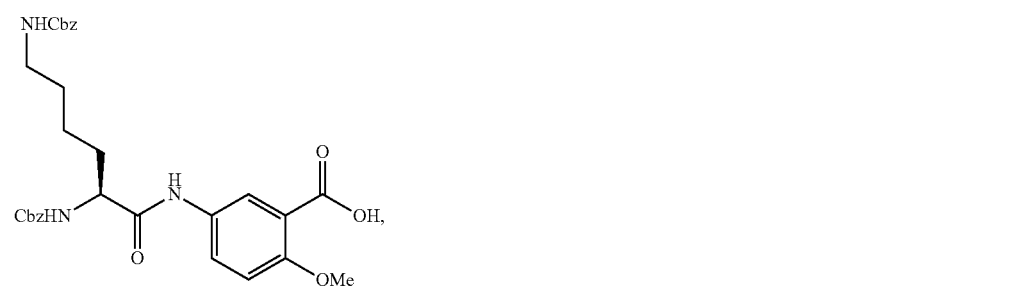
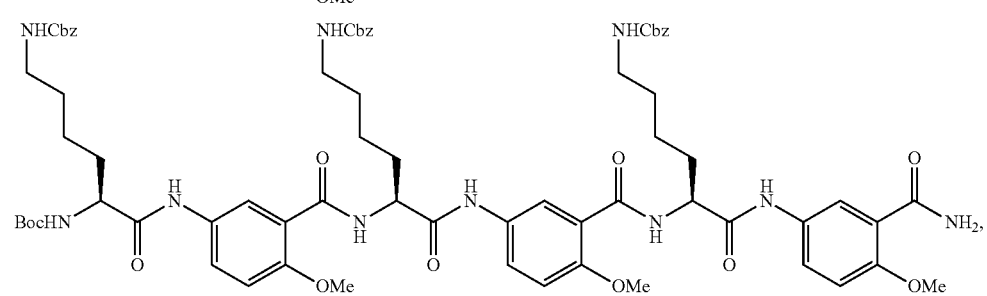
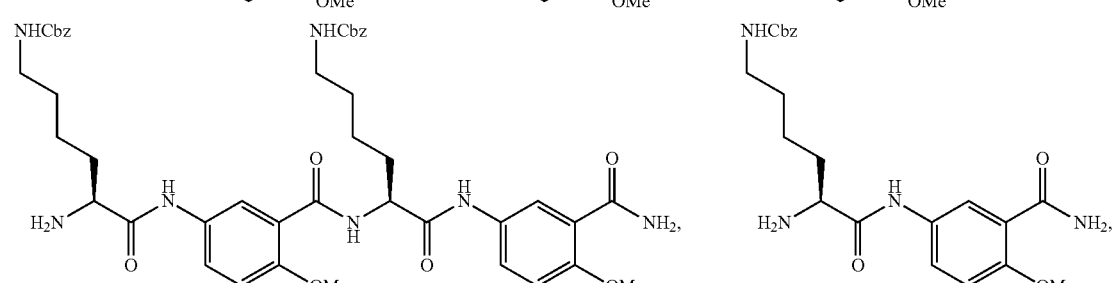
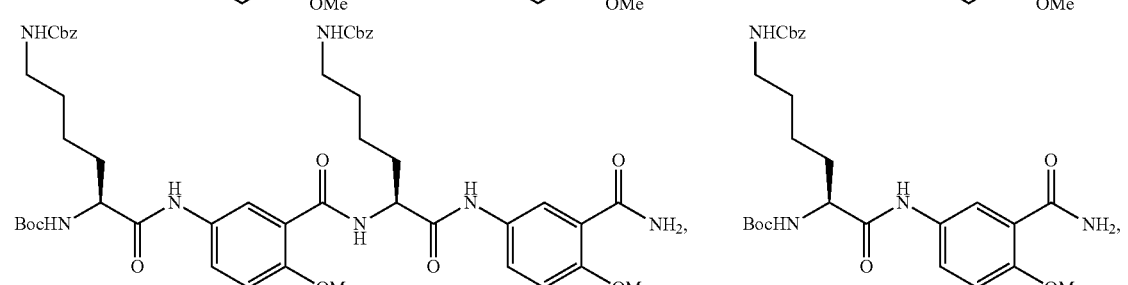
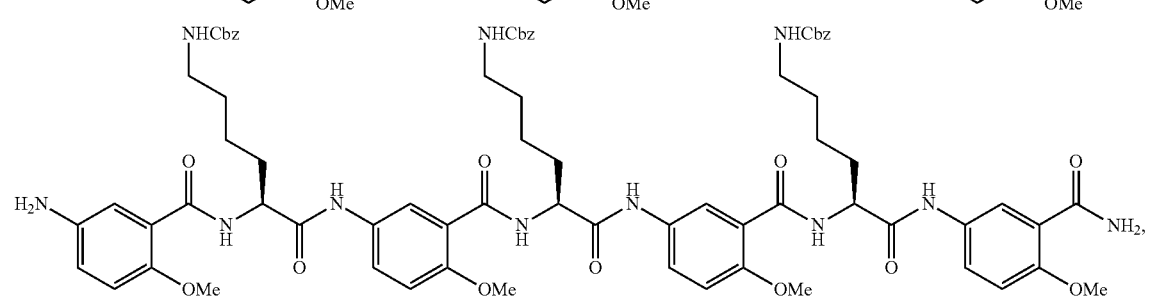

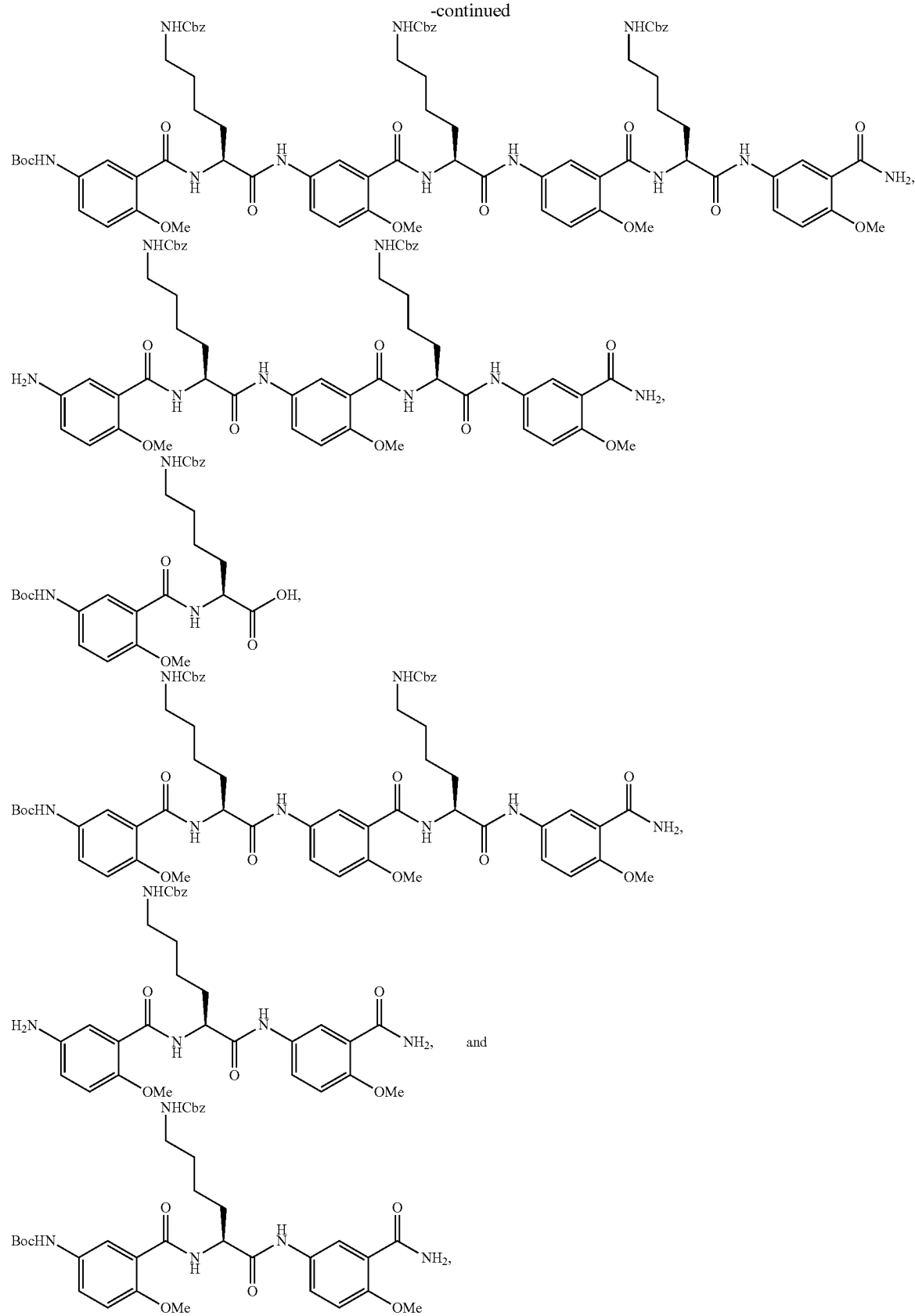
or pharmaceutically acceptable salt thereof.

DESCRIPTION OF EMBODIMENTS

As used herein, the term "about" means±5% of the value it describes. For example, about 90 means from 85.5 to 94.5.

As used herein, the term "reacting" refers to the bringing together of designated chemical reactants such that a chemical transformation takes place generating a compound different from any initially introduced into the system. Reacting can take place in the presence or absence of solvent.

As used herein, the terms "optional" or "optionally" mean that the subsequently described structure, event, or circumstance may or may not occur, and that the description includes instances where the event occurs and instances where it does not.

As used herein, the phrase "isolating a compound" means that the compound is separated from other components of a mixture (e.g., a synthetic organic chemical reaction mixture), such as by conventional techniques, and the compound isolated is purified (and can be subject to further purification).

In some embodiments, the present invention provides methods for preparing a compound of Formula I:

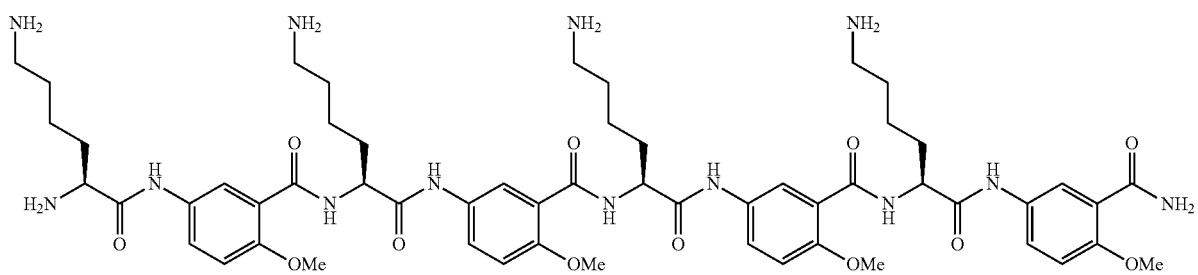

and/or a pharmaceutically acceptable salt thereof, comprising:

a) removing the Cbz groups from a compound of Formula II:

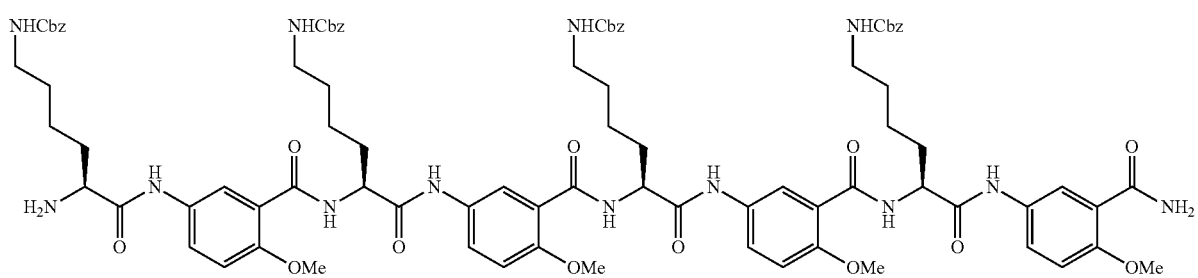

or pharmaceutically acceptable salt thereof, under a hydrogenation/hydrogenolysis condition to form the compound of Formula I, or pharmaceutically acceptable salt thereof; and b) optionally isolating the compound of Formula I or pharmaceutically acceptable salt thereof.

Removal of the Cbz group from the compound of Formula II, or pharmaceutically acceptable salt thereof, can be carried out by using a suitable hydrogenation/hydrogenolysis condition. Examples of suitable hydrogenation/hydrogenolysis conditions that can be used in step a) include those conditions known in the art of synthetic organic chemistry. For example, a $H_2$ gas (optionally under a pressure of more than 1 atmosphere, for example a pressure of about 30 to about 80 psi, or about 40 to about 70 psi) and a metal catalyst can be used. Examples of suitable metal catalysts include, but are not limited to, a Pd catalyst (for example, a Pd/C catalyst (e.g., a 5%, 10%, or 20% Pd/C); Pd black; $Pd(OH)_2$; and $PdCl_2$); Raney Ni, a platinum catalyst, a rhodium catalyst, and a ruthenium catalyst. Other hydrogen sources can also be used, for example, those suitable for transfer hydrogenolysis such as formic acid, ammonium formate, and 1,4-cyclohexadiene. In some embodiments, the metal catalyst used in step a) is Pd/C.

In some embodiments, the reaction product is a salt of the compound of Formula I, for example, a (penta) HCl salt. In such embodiments, an acid (such as 5 molar equivalent HCl relative to the compound of the compound of Formula II) can be added to the reaction mixture. The reaction in step a) can be carried out in a suitable solvent such as a polar solvent, such as an alcohol (such as methanol or ethanol) or a mixture of suitable solvents. The reaction can be carried out at a suitable temperature, for example, ambient temperature (about 20-25° C.) or up to a temperature at which the solvent in the reaction mixture is at reflux. The progress of the reaction can be monitored by a suitable method, such as an in-progress HPLC, GC, LC, or thin-layer-Chromatography method. In some embodiments, the yield of step a) is greater than about 80%, 85%, 90%, 92%, 95%, 97%, 98%, or 99%. In some embodiments, the yield of step a) is greater than about 85%.

Use of 5 molar equivalents of a weak organic acid, such as, for example, acetic acid, during the hydrogenation may provide for significantly less leaching of Pd into the compound versus use of HCl. Subsequent to the reaction, the acetate is displaced by a stoichiometric amount of HCl to provide the compound in the desired HCl salt form. Thus, it may be suitable to use a weak, non-mineral acid for the reaction that can be displaced by the strong mineral acid subsequent to the reaction.

The compound of Formula I, or pharmaceutically acceptable salt thereof, can be isolated (including purification) by various techniques known in the art. For example, in some cases it might be desired to isolate the reaction product by filtration and subsequent precipitation of the product from the filtrate (for example, by removal of all or part of the solvents from the filtrate). For another example, in some cases it might be desired to isolate the reaction product by extraction with an appropriate solvent or mixture of solvents, for example diethyl ether or ethyl acetate, and subsequent chromatography. Alternately, it might be desired in some cases to directly collect the product. In some embodiments, the isolated product may be further purified by washing one or more times with an appropriate solvent, or mixture of solvents. In some embodiments, the product can be further purified, for example, by recrystallization. The recrystallization can be performed with a solvent, or with a mixture of solvents. In some embodiments, the product can be further purified, for example, by chromatography (for example on silica gel such as 3-mercaptopropyl ethyl sulfided silica gel). Suitable elution solvents include, but are not limited to, halogenated hydrocarbons, for example methylene chloride, alcohol (e.g., methanol), or mixtures thereof. Those skilled in the art will be able to choose other suitable solvents. In some embodiments, isolation (including purification) of the reaction product includes removing the catalyst from the reaction product. The purity of the isolated (or purified) product can be determined by a suitable method, such as using HPLC. For example, levels of Pd catalyst can be determined by a suitable method, such as Inductively Coupled Plasma (ICP) spectroscopy.

In some embodiments, the compound of Formula II, or pharmaceutically acceptable salt thereof, used in step a) can be prepared by:

c) removing the Boc group from a compound of Formula III:

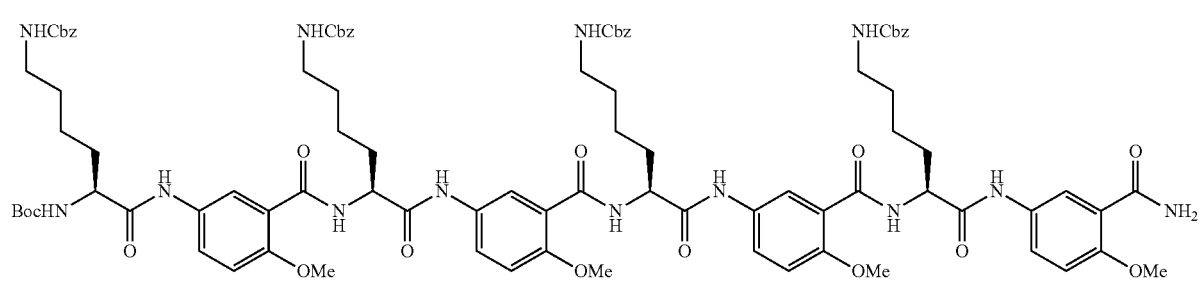

III or pharmaceutically acceptable salt thereof, to form the compound of Formula II or pharmaceutically acceptable salt thereof.

Removal of the Boc group can be carried out by using a suitable reagent or reagents, such as a an acid (e.g., $H_3PO_4$, TFA, HCl, TsOH, or $H_2SO_4$) or TMSOTf/2,6-lutidine. In some embodiments, an acid (e.g., $H_3PO_4$) is used for the removal of the Boc Group. In some embodiments, the reagent or acid used for the removal of the Boc group can be neat or present in a suitable solvent such as $CH_2Cl_2$, EtOAc, THF, dioxane, water, or a mixture of any two or more of these solvents.

The reaction in step c) can be carried out in a suitable solvent such as a polar solvent, for example, an ether (e.g., THF), a halogenated solvent (such as DCM), an alcohol (e.g., methanol or ethanol), or a mixture of suitable solvents. The reaction can be carried out at a suitable temperature, for example, ambient temperature (about 20-25° C.). The reaction product of step c) can be isolated as either the compound of Formula II or a salt thereof (for example, using a base, such as NaOH, to neutralize the acid used in the reaction of step c)). In some embodiments, the yield of step c) is greater than about 80%, 85%, 90%, 92%, 95%, 97%, 98%, or 99%. In some embodiments, the yield of step c) is greater than about 90%.

In some embodiments, the compound of Formula III, or pharmaceutically acceptable salt thereof, used in step c) can be prepared by:

d) reacting a compound of Formula IV:

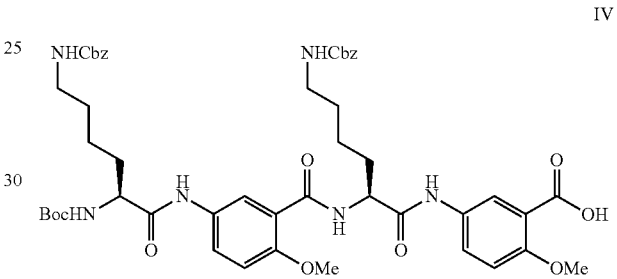

IV or pharmaceutically acceptable salt thereof with a compound of Formula V:

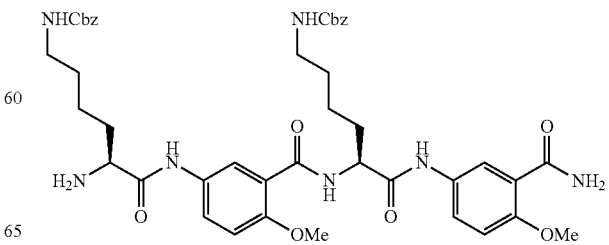

V or pharmaceutically acceptable salt thereof.

The reaction of step d) can be carried out in the presence of a coupling reagent and an organic base, to form the compound of Formula III, or pharmaceutically acceptable salt thereof. Examples of suitable coupling reagents include, but are not limited to, benzotriazol-1-yloxytris(dimethylamino)phosphonium hexafluorophosphate (BOP), 2-(1H-benzotriazol-1-yl)-1,1,3,3-tetramethyluronium hexafluorophosphate (HBTU), O-(7-azabenzotriazol1-yl)-N,N,N',N'-tetramethyluronium hexafluorophosphate (HATU), 1-ethyl-3-(3-dimethylaminopropyl)carbodiimide (EDC or EDAC), dicyclohexylcarbodimide (DCC), N,N'-diisopropylcarbodiimide (DIC), benzotriazol-1-yl-oxytripyrrolidinophosphonium hexafluorophosphate (Py-BOP), N,N'-carbonyldiimidazole (CDI), N-hydroxybenzotriazole (HOBt), 1H-Benzotriazolium 1-[bis(dimethyl-amino)methylene]-5-chloro-hexafluorophosphate (1-),3-oxide (HCTU), a suitable 1,3,5-triazine derivative (see, for example, Kaminski, Tetrahedron Letters, 1985, 26, 2901-2904; examples of suitable 1,3,5-triazine derivatives include, but are not limited to, 2,4,6-trichloro-1, 3,5-triazine; 2-chloro-4,6-diphenoxy-1,3,5-triazine; 2-chloro-4,6-dibenzyloxy-1,3,5-triazine; 2-chloro-4,6-dimethoxy-1,3,5-triazine; 2,4-dichloro-6-phenoxy-1,3,5-triazine; 2,4-dichloro-6-benzyloxy-1,3,5-triazine; or 2,4-dichloro-6-methoxy-1,3,5-triazine), and a mixture of two or more thereof. In some embodiments, the coupling reagent in step d) includes a mixture of EDAC and HOBt.

In some embodiments, the acid used in the coupling reaction can be converted to a more reactive species (by using a suitable activating reagent), for example, an acid halide or a mixed anhydride. In some embodiments wherein the acid is converted to an activated species, the coupling reagent is optional for the coupling reaction. In some embodiments, the activated species can be isolated before the coupling reaction. Examples of suitable activating reagents include, but are not limited to, alkyl chloroformate (e.g., ethyl chloroformate or isobutyl chloroformate), thionyl chloride, oxalyl chloride, cyanuric chloride, and $PBr_3$.

In some embodiments, the activating or coupling reagent in step d) is chosen from those that prevent racemization of any chiral center present in the reactants (and/or reaction products) (see, Konig et al., Chem. Ber., 1970, 103, 788; listing HOBt as such a coupling reagent).

The coupling reaction can be carried out in the presence of a suitable base. Examples of suitable bases include, but are not limited to, triethylamine (TEA), diisopropylethylamine (DIEA), N-methylmorpholine (NMM), N—N-dimethylaminopyridine (DMAP), pyridine, and imidazole. In some embodiments, the base is N-methylmorpholine.

The reaction in step d) can be carried out in a suitable solvent such as a polar solvent, for example, an ether (e.g., tetrahydrofuran or THF), a halogenated solvent (such as dichloromethane (DCM) or chloroform), or a mixture of suitable solvents. The reaction can be carried out at a suitable temperature, for example, ambient temperature (about 20-25° C.) or up to a temperature at which the solvent in the reaction mixture is at reflux. The reaction product of step d) can be isolated (including purification) by any suitable techniques known in the art. In some embodiments, the yield of step d) is greater than about 65%, 70%, 75%, 80%, 85%, 90%, 92%, 95%, 97%, 98%, or 99%. In some embodiments, the yield of step d) is greater than about 80%.

In some embodiments, the compound of Formula V, or pharmaceutically acceptable salt thereof, used in step d) can be prepared by:

e) reacting a compound of Formula IV:

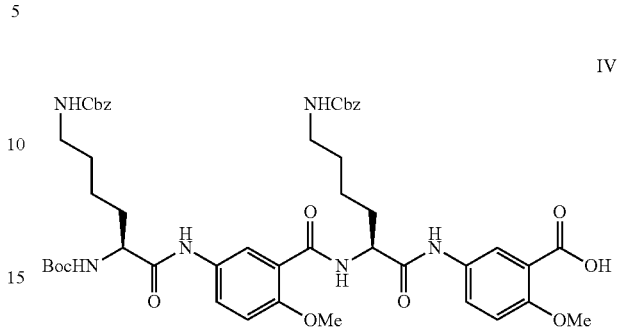

IV or, pharmaceutically acceptable salt thereof, with ammonia or an ammonia producing reagent, to form a compound of Formula VI:

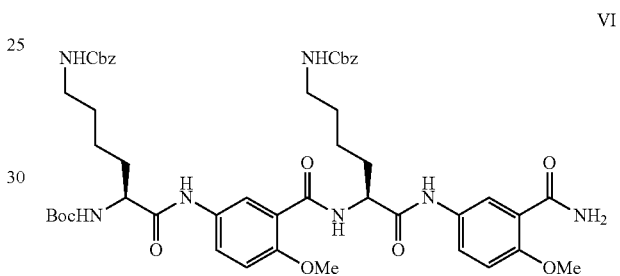

VI or, pharmaceutically acceptable salt thereof and f) removing the Boc group from the compound of Formula VI, or pharmaceutically acceptable salt thereof, to form the compound of Formula V, or pharmaceutically acceptable salt thereof.

In some embodiments, the coupling reaction of step e) is carried out in the presence of an activating reagent (or a coupling reagent) and an organic base. Suitable activating reagents (or coupling reagents) and organic bases are known in the art.

In some embodiments, ammonia (either neat or in a solvent such as water or dioxane) is used in step e). In some embodiments, an ammonia producing reagent (such as $NH_4Cl$) is used.

In some embodiments, the acid (i.e., the compound of Formula IV) used in the coupling reaction can be converted to a more reactive species (by using a suitable activating reagent), for example, an acid halide or a mixed anhydride. In some embodiments wherein the acid is converted to an activated species, the coupling reagent is optional for the coupling reaction. In some embodiments, the activated species can be isolated before the coupling reaction. Examples of suitable activating reagents include, but are not limited to, alkyl chloroformate (e.g., ethyl chloroformate or isobutyl chloroformate), thionyl chloride, oxalyl chloride, cyanuric chloride, and $PBr_3$. In some embodiments, the activating reagent used is ethyl chloroformate. In some embodiments, the base used is DIEA.

In some embodiments, the yield of step e) is greater than about 80%, 85%, 90%, 92%, 95%, 97%, 98%, or 99%. In some embodiments, the yield of step e) is greater than about 92%.

Removal of the Boc group in step f) can be carried out by using a suitable reagent or suitable reagents, such as an acid (e.g., $H_3PO_4$, TFA, HCl, TsOH, or $H_2SO_4$) or TMSOTf/2,6-lutidine. In some embodiments, an acid (e.g., trifluoroacetic acid (TFA)) is used for removal of the Boc Group. In some embodiments, the yield of step f) is greater than about 70%, 75%, 80%, 85%, 90%, 92%, 95%, 97%, 98%, or 99%. In some embodiments, the yield of step f) is greater than about 85%.

In some embodiments, the compound of Formula V, or pharmaceutically acceptable salt thereof, used in the present invention can be prepared by:

g) hydrolyzing a compound of Formula VII:

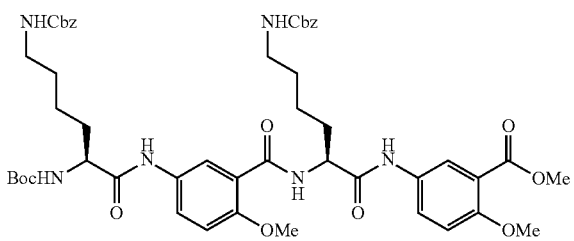

VII or pharmaceutically acceptable salt thereof, in the presence of a base, to form the compound of Formula IV.

Examples of suitable bases in step g) include, but are not limited to, metal hydroxide (e.g., LiOH, NaOH, KOH, $Ba(OH)_2$) and metal carbonate (e.g., $Na_2CO_3$, $K_2CO_3$, and $Cs_2CO_3$). In some embodiments, the base in step g) is LiOH. In some embodiments, the yield of step g) is greater than about 80%, 85%, 90%, 92%, 95%, 97%, 98%, or 99%. In some embodiments, the yield of step g) is greater than about 95%.

In some embodiments, the compound of Formula VII, or pharmaceutically acceptable salt thereof, used in the present invention can be prepared by:

h) reacting a compound of Formula VIII:

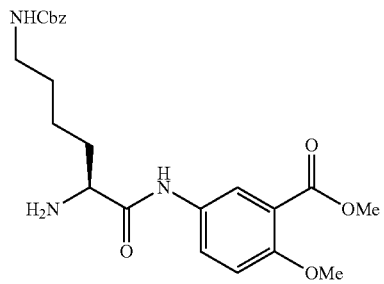

VIII or pharmaceutically acceptable salt thereof, with a compound of Formula IX:

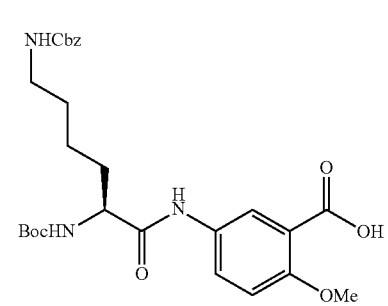

IX or pharmaceutically acceptable salt thereof, to form the compound of Formula VII, or pharmaceutically acceptable salt thereof.

In some embodiments, the coupling reaction of step h) is carried out in the presence of an activating reagent (or a coupling reagent) and an organic base. Suitable activating reagents (or coupling reagents) and organic bases are known in the art. In some embodiments, the coupling reaction of step h) is carried out in the presence of a coupling reagent. In some embodiments, the coupling reagent in step h) includes a mixture of EDAC and HOBt.

In some embodiments, the organic base in step h) is NMM. In some embodiments, the yield of step h) is greater than about 65%, 70%, 75%, 80%, 85%, 90%, 92%, 95%, 97%, 98%, or 99%. In some embodiments, the yield of step h) is greater than about 80%.

In some embodiments, the compound of Formula VIII, or pharmaceutically acceptable salt thereof, used in the present invention can be prepared by:

i) hydrolyzing a compound of Formula X:

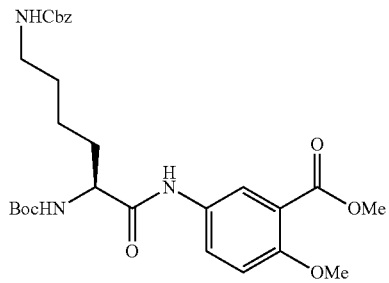

X or pharmaceutically acceptable salt thereof, in the presence of a base, to form a compound of Formula IX:

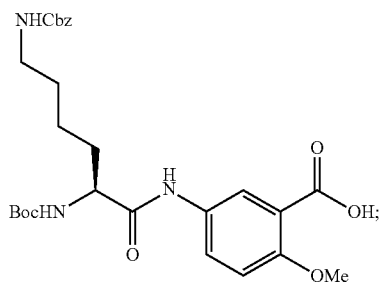

IX and j) removing the Boc group from a compound of Formula X, or pharmaceutically acceptable salt thereof, to form the compound of Formula VIII, or pharmaceutically acceptable salt thereof.

Thus, the compound of Formula X is taken in two directions. The compound of Formula VIII is prepared by removal of a Boc group from the compound of Formula X (i.e., the compound of Formula VIII is obtained directly from the compound of Formula X via removal of the Boc group). Hydrolysis also affords the compound of Formula IX and removal of the Boc group affords the compound of Formula VIII.

Examples of suitable bases in step i) include, but are not limited to, metal hydroxide (e.g., LiOH, NaOH, KOH, $Ba(OH)_2$) and metal carbonate (e.g., $Na_2CO_3$, $K_2CO_3$, and $Cs_2CO_3$). In some embodiments, the base in step i) is LiOH. In some embodiments, the yield of step i) is greater than about 80%, 85%, 90%, 92%, 95%, 97%, 98%, or 99%. In some embodiments, the yield of step i) is greater than about 92%.

Removal of the Boc group in step j) can be carried out by using a suitable reagent or suitable reagents, such as an acid (e.g., $H_3PO_4$, TFA, HCl, TsOH, or $H_2SO_4$) or TMSOTf/2,6-lutidine. In some embodiments, an acid (e.g., TsOH) is used for removal of the Boc Group. In some embodiments, the yield of step j) is greater than about 80%, 85%, 90%, 92%, 95%, 97%, 98%, or 99%. In some embodiments, the yield of step j) is greater than about 95%.

In some embodiments, the compound of Formula X, or pharmaceutically acceptable salt thereof, used in the present invention can be prepared by:

k) reacting a compound of Formula XI:

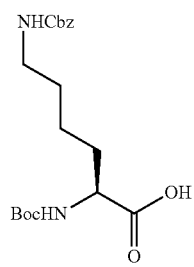

XI or pharmaceutically acceptable salt thereof, with a compound of Formula XII:

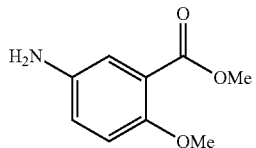

XII or pharmaceutically acceptable salt thereof, to form the compound of Formula X, or pharmaceutically acceptable salt thereof.

In some embodiments, the coupling reaction of step k) is carried out in the presence of an activating reagent (or a coupling reagent) and an organic base. Suitable activating reagents (or coupling reagents) and organic bases are known in the art. In some embodiments, the coupling reaction of step k) is carried out in the presence of a coupling reagent. In some embodiments, the coupling reagent in step k) is a mixture of EDAC and HOBt.

In some embodiments, the organic base in step k) is NMM. In some embodiments, the yield of step k) is greater than about 80%, 85%, 90%, 92%, 95%, 97%, 98%, or 99%. In some embodiments, the yield of step k) is greater than about 90%.

The present invention also provides methods for preparing a compound of Formula I:

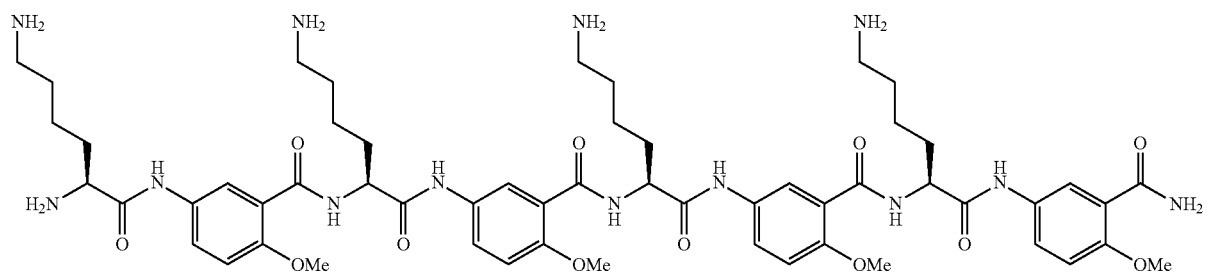

I or pharmaceutically acceptable salt thereof, comprising:

a1) removing the Cbz groups from a compound of Formula II-1:

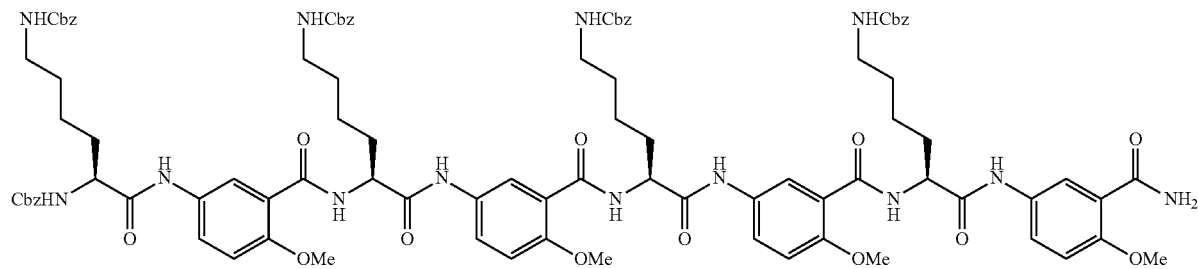

II-1 or pharmaceutically acceptable salt thereof, under a hydrogenation/hydrogenolysis condition to form the compound of Formula I, or pharmaceutically acceptable salt thereof; and b1) optionally isolating the compound of Formula I or pharmaceutically acceptable salt thereof.

Removal of the Cbz group from the compound of Formula II-1, or pharmaceutically acceptable salt thereof, can be realized by using a suitable hydrogenation/hydrogenolysis reaction condition. Examples of suitable hydrogenation/hydrogenolysis conditions that can be used in step a-1) include those conditions known in the art of synthetic organic chemistry. For example, a $H_2$ gas (optionally under a pressure more than 1 atmosphere, for example a pressure of about 30 to about 80 psi, or about 40 to about 70 psi) and a metal catalyst can be used. Examples of suitable metal catalysts include, but are not limited to, a Pd catalyst (for example, a Pd/C catalyst (e.g., a 5%, 10%, or 20% Pd/C); Pd black; $Pd(OH)_2$; and $PdCl_2$); Raney Ni, a platinum catalyst, a rhodium catalyst, and a ruthenium catalyst. Other hydrogen sources can also be used, for example, those suitable for transfer hydrogenolysis such as formic acid, ammonium formate, and 1,4-cyclohexadiene. In some embodiments, the metal catalyst used in step a1) is Pd/C (e.g., a 5%, 10%, or 20% Pd/C).

In some embodiments, the reaction product of step a1) is a salt of the compound of Formula I, for example, a (penta) HCl salt thereof. In some embodiments, an acid (such as 5 molar equivalents of HCl relative to the compound of Formula II-1) can be added to the reaction mixture. The reaction in step a1) can be carried out in a suitable solvent such as a polar solvent, such as an alcohol (such as methanol or ethanol), or an ether (e.g., THF), or a mixture of suitable solvents. The reaction can be carried out at a suitable temperature, for example, ambient temperature (about 20-25° C.) or up to a temperature at which the solvent in the reaction mixture is at reflux. The progress of the reaction can be monitored by a suitable method, such as an in-progress HPLC, GC, LC, or thin-layer-Chromatography method. In some embodiments, the yield of step a1) is greater than about 70%, 75%, 80%, 85%, 90%, 92%, 95%, 97%, 98%, or 99%. In some embodiments, the yield of step a1) is greater than about 85%.

It has been observed that use of 5 molar equivalents of a weak organic acid, such as, for example, acetic acid, during the hydrogenation may provide for significantly less leaching of Pd into the compound versus use of HCl. Subsequent to the reaction, the acetate is displaced by a stoichiometric amount of HCl to provide the compound in the desired HCl salt form. Thus, it may be suitable to use a weak, non-mineral acid for the reaction that can be displaced by the strong mineral acid subsequent to the reaction.

The compound of Formula I, or pharmaceutically acceptable salt thereof, can be isolated (including purification) by various techniques known in the art, such as those described hereinabove.

In some embodiments, the compound of Formula II-1, or pharmaceutically acceptable salt thereof, used in step a1) can be prepared by:

c1) reacting a compound of Formula III-1:

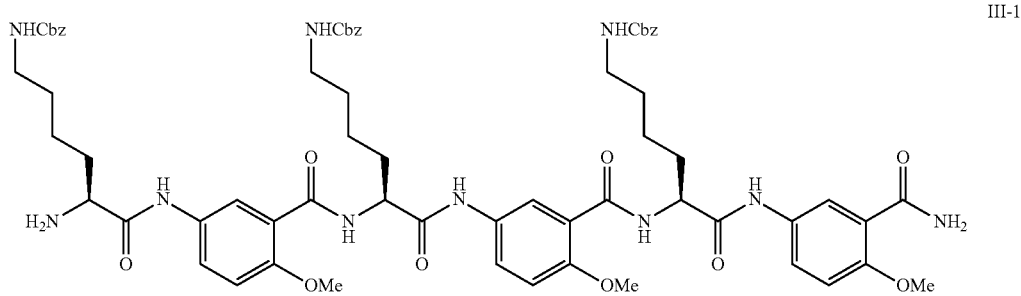 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)[C@@H](N)CCCCNC(=O)OCc4ccccc4)ccc3OC)ccc2OC)cc1C(N)=O]

III-1 or pharmaceutically acceptable salt thereof, with a compound of Formula IV-1:

IV-1 or pharmaceutically acceptable salt thereof, to form the compound of Formula II-1, or pharmaceutically acceptable salt thereof.

The reaction of step c1) can be carried out in the presence of a coupling reagent and an organic base, to form the compound of Formula II-1, or pharmaceutically acceptable salt thereof. Examples of suitable coupling reagents include, but are not limited to, BOP, HBTU, HATU, EDAC, DCC, DIC, Py-BOP, CDI, HOBt, HCTU, a suitable 1,3,5-triazine derivative, and a mixture of two or more thereof.

In some embodiments, the acid used in the coupling reaction (i.e., the compound of Formula IV-1) can be converted to a more reactive species (by using a suitable activating reagent), for example, an acid halide or a mixed anhydride. In some embodiments wherein the acid is converted to an activated species, the coupling reagent is optional for the coupling reaction. In some embodiments, the activated species can be isolated before the coupling reaction. Examples of suitable activating reagents include, but are not limited to, alkyl chloroformate (e.g., ethyl chloroformate or isobutyl chloroformate), thionyl chloride, oxalyl chloride, cyanuric chloride, and $PBr_3$.

In some embodiments, the activating or coupling reagent in step c1) is chosen from those that prevent racemization of any chiral center present in the reactants (and/or the products). In some embodiments, the coupling reagent in step c1) includes a mixture of EDAC and HOBt.

The coupling reaction in step c1) can be carried out in the presence of a suitable base. Examples of suitable bases include, but are not limited to, TEA, DIEA, NMM, DMAP, pyridine, and imidazole. In some embodiments, the base is NMM.

The reaction in step c1) can be carried out in a suitable solvent such as a polar solvent, for example, an ether (e.g., THF), a halogenated solvent (such as DCM or chloroform), or a mixture of suitable solvents. The reaction can be carried out at a suitable temperature, for example, ambient temperature (about 20-25° C.) or up to a temperature at which the solvent in the reaction mixture is at reflux. The reaction product of step c1) can be isolated (including purification) by any suitable techniques known in the art. In some embodiments, the yield of step c1) is greater than about 65%, 70%, 75%, 80%, 85%, 90%, 92%, 95%, 97%, 98%, or 99%. In some embodiments, the yield of step c1) is greater than about 80%.

In some embodiments, the compound of Formula V-1, or pharmaceutically acceptable salt thereof, used in step c1) can be prepared by:

d1) reacting a compound of Formula VI-1:

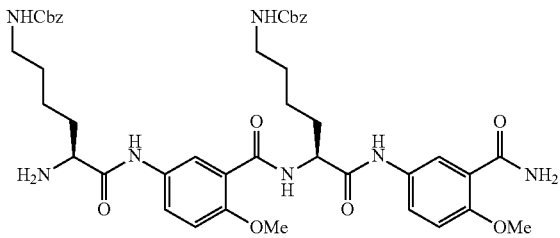

VI-1 or pharmaceutically acceptable salt thereof, with a compound of Formula VII-1:

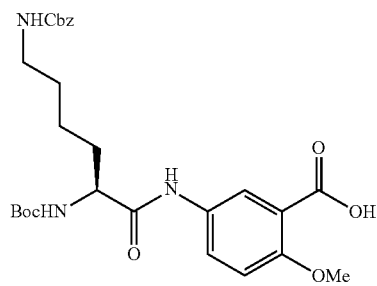

VII-1 or pharmaceutically acceptable salt thereof, to form a compound of Formula V-1:

or pharmaceutically acceptable salt thereof; and e1) removing the Boc group from the compound of Formula V-1, or pharmaceutically acceptable salt thereof, to form the compound of Formula III-1, or pharmaceutically acceptable salt thereof.

The reaction of step d1) can be carried out in the presence of a coupling reagent and an organic base, to form the compound of Formula V-1, or pharmaceutically acceptable salt thereof. Examples of suitable coupling reagents include, but are not limited to, BOP, HBTU, HATU, EDAC, DCC, DIC, Py-BOP, CDI, HOBt, HCTU, a suitable 1,3,5-triazine derivative, and a mixture of two or more thereof. In some embodiments, the acid used in the reaction (i.e., the compound of Formula IV-1) of step d1) can be converted to a more reactive species (by using a suitable activating reagent), for example, an acid halide or a mixed anhydride (in certain such embodiments, a coupling reagent is optional for the coupling reaction of d1); in certain such embodiments, the activated species can be isolated before the coupling reaction of d1)). In some embodiments, the activating or coupling reagent in step d1) is chosen from those that prevent racemization of any chiral center present in the reactants (and/or the products). In some embodiments, the coupling reagent in step d1) includes a mixture of EDAC and HOBt.

The reaction in step d1) can be carried out in the presence of a suitable base. Examples of suitable bases include, but are not limited to, TEA, DIEA, NMM, DMAP, pyridine, and imidazole. In some embodiments, the base is NMM.

The reaction in step d1) can be carried out in a suitable solvent such as a polar solvent, for example, an ether (e.g., THF), a halogenated solvent (such as DCM or chloroform), or a mixture of suitable solvents. The reaction can be carried out at a suitable temperature, for example, ambient temperature (about 20-25° C.) or up to a temperature at which the solvent in the reaction mixture is at reflux. The reaction product of step d1) can be isolated (including purification) by any suitable techniques known in the art. In some embodiments, the yield of step d1) is greater than about 80%, 85%, 90%, 92%, 95%, 97%, 98%, or 99%. In some embodiments, the yield of step d1) is greater than about 92%.

The reaction to remove the Boc group in step e1) can be carried out by using a suitable reagent or suitable reagents, such as an acid (e.g., $H_3PO_4$, TFA, HCl, TsOH, or $H_2SO_4$) or TMSOTf/2,6-lutidine. In some embodiments, an acid (e.g., TFA) is used for removal of the Boc group. In some embodiments, the reagent or acid used for the removal of the Boc group can be neat or present in a suitable solvent such as $CH_2Cl_2$, EtOAc, THF, dioxane, water, or a mixture of any two or more of these solvents.

The reaction in step e1) can be carried out in a suitable solvent such as a polar solvent, for example, an ether (e.g.,

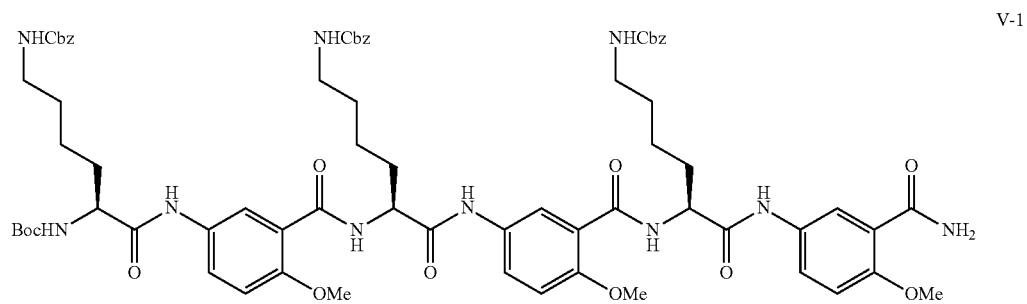 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)[C@H](CCCCNC(=O)OCc4ccccc4)NC(=O)OC(C)(C)C)ccc3OC)ccc2OC)cc1C(N)=O]

V-1

THF), a halogenated solvent (such as DCM), an alcohol (e.g., methanol or ethanol), or a mixture of suitable solvents. The reaction can be carried out at a suitable temperature, for example, ambient temperature (about 20-25° C.) or up to a temperature at which the solvent in the reaction mixture is at reflux. The reaction product of step e1) can be isolated as either the compound of Formula III-1, or a salt thereof, (for example, using a base such as NaOH to neutralize the acid used in the reaction of step e1)). In some embodiments, the yield of step e1) is greater than about 65%, 70%, 75%, 80%, 85%, 90%, 92%, 95%, 97%, 98%, or 99%. In some embodiments, the yield of step e1) is greater than about 85%.

In some embodiments, the compound of Formula VI-1, or pharmaceutically acceptable salt thereof, used in step d1) can be prepared by:

f1) reacting a compound of Formula VIII-1:

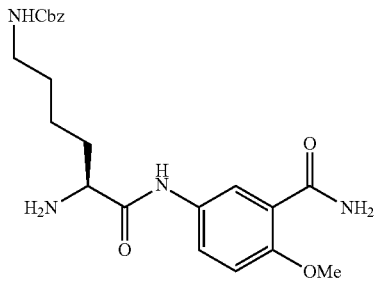

VIII-1 or pharmaceutically acceptable salt thereof, with a compound of Formula VII-1:

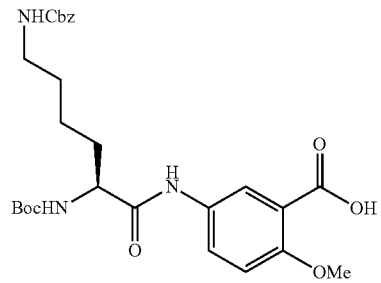

VII-1 or pharmaceutically acceptable salt thereof, in the presence of a coupling reagent and an organic base, to form a compound of Formula IX-1:

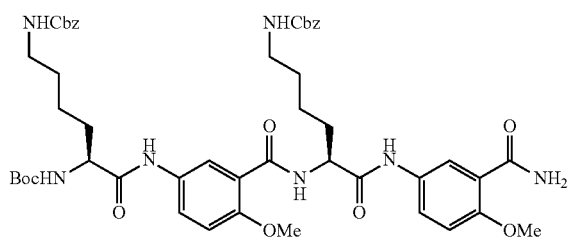

IX-1 or pharmaceutically acceptable salt thereof; and g1) removing the Boc group from the compound of Formula IX-1, or pharmaceutically acceptable salt thereof, in the presence of an acid, to form the compound of Formula VI-1, or pharmaceutically acceptable salt thereof.

The reaction of step f1) can be carried out in the presence of a coupling reagent and an organic base, to form the compound of Formula IX-1, or pharmaceutically acceptable salt thereof. Examples of suitable coupling reagents include, but are not limited to, BOP, HBTU, HATU, EDAC, DCC, DIC, Py-BOP, CDI, HOBt, HCTU, a suitable 1,3,5-triazine derivative, and a mixture of two or more thereof. In some embodiments, the acid used in the reaction (i.e., the compound of Formula VII-1) of step f1) can be converted to a more reactive species (by using a suitable activating reagent), for example, an acid halide or a mixed anhydride (in certain such embodiments, a coupling reagent is optional for the coupling reaction of f1); in certain such embodiments, the activated species can be isolated before the coupling reaction of f1)). In some embodiments, the activating or coupling reagent in step f1) is chosen from those that prevent racemization of any chiral center present in the reactants (and/or the products). In some embodiments, the coupling reagent in step f1) includes a mixture of EDAC and HOBt.

The reaction in step f1) can be carried out in the presence of a suitable base. Examples of suitable bases include, but are not limited to, TEA, DIEA, NMM, DMAP, pyridine, and imidazole. In some embodiments, the base is NMM.

The reaction in step f1) can be carried out in a suitable solvent such as a polar solvent, for example, an ether (e.g., THF), a halogenated solvent (such as DCM or chloroform), or a mixture of suitable solvents. The reaction can be carried out at a suitable temperature, for example, ambient temperature (about 20-25° C.). The reaction product of step f1) can be isolated (including purification) by any suitable techniques known in the art. In some embodiments, the yield of step f1) is greater than about 65%, 70%, 75%, 80%, 85%, 90%, 92%, 95%, 97%, 98%, or 99%. In some embodiments, the yield of step f1) is greater than about 92%.

Removal of the Boc group in step g1) can be carried out by using a suitable reagent or suitable reagents, such as an acid (e.g., $H_3PO_4$, TFA, HCl, TsOH, or $H_2SO_4$) or TMSOTf/2,6-lutidine. In some embodiments, an acid (e.g., TFA) is used for removal of the Boc group. In some embodiments, the reagent or acid used for removal of the Boc group can be neat or present in a suitable solvent such as $CH_2Cl_2$, EtOAc, THF, dioxane, water, or a mixture of any two or more of these solvents.

The reaction in step g1) can be carried out in a suitable solvent such as a polar solvent, for example, an ether (e.g., THF), a halogenated solvent (such as DCM), an alcohol (e.g., methanol or ethanol), or a mixture of suitable solvents. The reaction can be carried out at a suitable temperature, for example, ambient temperature (about 20-25° C.) or up to a temperature at which the solvent in the reaction mixture is at reflux. The reaction product of step g1) can be isolated as either the compound of Formula VI-1, or a salt thereof, (for example, using a base such as NaOH to neutralize the acid used in the reaction of step (g1)). In some embodiments, the yield of step g1) is greater than about 70%, 75%, 80%, 85%, 90%, 92%, 95%, 97%, 98%, or 99%. In some embodiments, the yield of step g1) is greater than about 85%.

In some embodiments, the compound of Formula VIII-1, or pharmaceutically acceptable salt thereof, used in step f1) can be prepared by:

h1) reacting a compound of Formula XI-1:

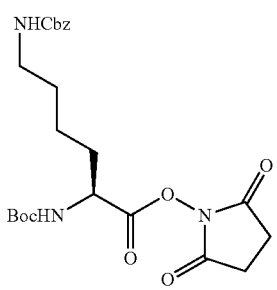

XI-1 or pharmaceutically acceptable salt thereof, with a compound of Formula XII-1:

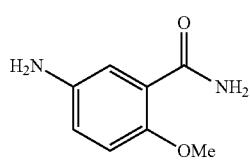

XII-1 or pharmaceutically acceptable salt thereof, optionally in the presence of an organic base, to form a compound of Formula X-1:

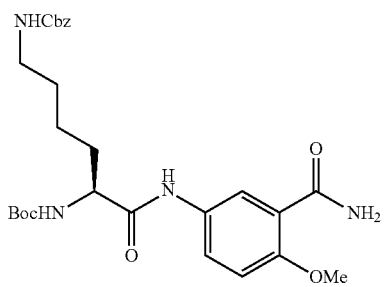

X-1 or pharmaceutically acceptable salt thereof; and i1) removing the Boc group from the compound of Formula X-1, or pharmaceutically acceptable salt thereof, in the presence of an acid to form the compound of Formula VIII-1, or pharmaceutically acceptable salt thereof.

The reaction in step h1) can be carried out in the presence of a suitable base. Examples of suitable bases include, but are not limited to, TEA, DIEA, NMM, DMAP, pyridine, and imidazole. In some embodiments, the base is DMAP.

The reaction in step h1) can be carried out in a suitable solvent such as a polar solvent, for example, an ether (e.g., THF), a halogenated solvent (such as DCM or chloroform), ethyl acetate, or a mixture of suitable solvents. The reaction can be carried out at a suitable temperature, for example, ambient temperature (about 20-25° C.) or up to a temperature at which the solvent in the reaction mixture is at reflux. The reaction product of step h1) can be isolated (including purification) by any suitable techniques known in the art. In some embodiments, the yield of step h1) is greater than about 80%, 85%, 90%, 92%, 95%, 97%, 98%, or 99%. In some embodiments, the yield of step h1) is greater than about 98%.

Removal of the Boc group in step i1) can be carried out by using a suitable reagent or suitable reagents, such as a an acid (e.g., $H_3PO_4$, TFA, HCl, TsOH, or $H_2SO_4$) or TMSOTf/2,6-lutidine. In some embodiments, an acid (e.g., TFA) is used for removal of the Boc group. In some embodiments, the reagent or acid used for removal of the Boc group can be neat or present in a suitable solvent such as $CH_2Cl_2$, EtOAc, THF, dioxane, water, or a mixture of any two or more of these solvents.

The reaction in step i1) can be carried out in a suitable solvent such as a polar solvent, for example, an ether (e.g., THF), a halogenated solvent (such as DCM), an alcohol (e.g., methanol or ethanol), or a mixture of suitable solvents. The reaction can be carried out at a suitable temperature, for example, ambient temperature (about 20-25° C.) or up to a temperature at which the solvent in the reaction mixture is at reflux. The reaction product of step i1) can be isolated as either the compound of Formula VIII-1, or a salt thereof, (for example, using a base such as NaOH to neutralize the acid used in the reaction of step i1)). In some embodiments, the yield of step i1) is greater than about 65%, 70%, 75%, 80%, 85%, 90%, 92%, 95%, 97%, 98%, or 99%. In some embodiments, the yield of step i1) is greater than about 85%.

In some embodiments, the compound of Formula VII-1, or pharmaceutically acceptable salt thereof, used herein can be prepared by:

j1) reacting a compound of Formula XI-1:

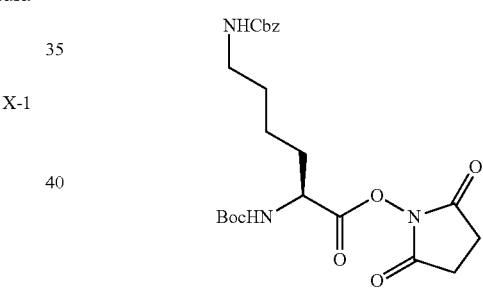

XI-1 or pharmaceutically acceptable salt thereof, with a compound of Formula XIII-1:

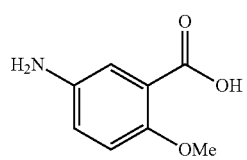

XIII-1 or pharmaceutically acceptable salt thereof, to form the compound of Formula VII-1, or pharmaceutically acceptable salt thereof.

The reaction in step j1) can be carried out in a suitable solvent such as a polar solvent, for example, an ether (e.g., THF), a halogenated solvent (such as DCM or chloroform), ethyl acetate, or a mixture of suitable solvents. The reaction can be carried out at a suitable temperature, for example, ambient temperature (about 20-25° C.) or up to a temperature at which the solvent in the reaction mixture is at reflux. The reaction product of step j1) can be isolated (including purification) by any suitable techniques known in the art. In some embodiments, the yield of step j1) is greater than about 80%, 85%, 90%, 92%, 95%, 97%, 98%, or 99%. In some embodiments, the yield of step j1) is greater than about 95%.

In some embodiments, the compound of Formula IV-1, or pharmaceutically acceptable salt thereof, used herein can be prepared by:

embodiments, the yield of step k1) is greater than about 65%, 70%, 75%, 80%, 85%, 90%, 92%, 95%, 97%, 98%, or 99%. In some embodiments, the yield of step k1) is greater than about 80%.

In some embodiments, the compound of Formula II-1, or pharmaceutically acceptable salt thereof, used in step a1) can also be prepared by:

c2) reacting a compound of Formula III-2:

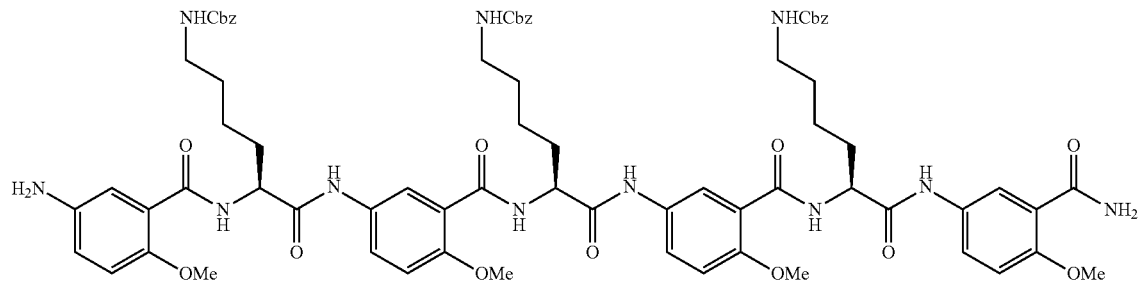

k1) reacting a compound of Formula XIV-1:

or pharmaceutically acceptable salt thereof, with a compound of Formula IV-2:

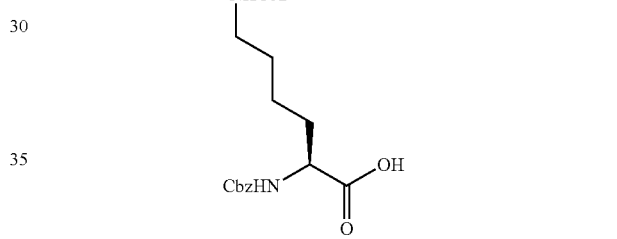

or pharmaceutically acceptable salt thereof, with a compound of Formula XIII-1:

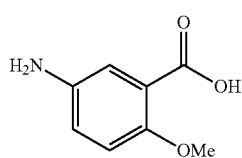

or pharmaceutically acceptable salt thereof, to form the compound of Formula IV-1, or pharmaceutically acceptable salt thereof.

The reaction in step k1) can be carried out in a suitable solvent such as a polar solvent, for example, an ether (e.g., THF), a halogenated solvent (such as DCM or chloroform), ethyl acetate, or a mixture of suitable solvents. The reaction can be carried out at a suitable temperature, for example, ambient temperature (about 20-25° C.) or up to a temperature at which the solvent in the reaction mixture is at reflux. The reaction product of step k1) can be isolated (including purification) by any suitable techniques known in the art. In some or pharmaceutically acceptable salt thereof, to form the compound of Formula II-1 or pharmaceutically acceptable salt thereof.

The reaction of step c2) can be carried out in the presence of a coupling reagent and an organic base, to form the compound of Formula II-1, or pharmaceutically acceptable salt thereof. Examples of suitable coupling reagents include, but are not limited to, BOP, HBTU, HATU, EDAC, DCC, DIC, Py-BOP, CDI, HOBt, HCTU, a suitable 1,3,5-triazine derivative, and a mixture of two or more thereof.

In some embodiments, the acid used in the coupling reaction (i.e., the compound of Formula IV-2) can be converted to a more reactive species (by using a suitable activating reagent), for example, an acid halide or a mixed anhydride. In such embodiments wherein the acid was converted to an activated species, the coupling reagent is optional for the coupling reaction. In some such embodiments, the activated species can be isolated before the coupling reaction. Examples of suitable activating reagents include, but are not limited to, alkyl chloroformate (e.g., ethyl chloroformate or isobutyl chloroformate), thionyl chloride, oxalyl chloride, cyanuric chloride, and $PBr_3$.

In some embodiments, the activating or coupling reagent in step c2) is chosen from those that prevent racemization of any chiral center present in the reactants (and/or the products). In some embodiments, the coupling reagent in step c2) includes a suitable 1,3,5-triazine derivative (e.g., 2-chloro-4,6-dimethoxy-1,3,5-triazine).

The coupling reaction in step c2) can be carried out in the presence of a suitable base. Examples of suitable bases include, but are not limited to, TEA, DIEA, NMM, DMAP, pyridine, and imidazole. In some embodiments, the base is NMM.

The reaction in step c2) can be carried out in a suitable solvent such as a polar solvent, for example, an ether (e.g., THF), a halogenated solvent (such as DCM or chloroform), or a mixture of suitable solvents. The reaction can be carried out at a suitable temperature, for example, ambient temperature (about 20-25° C.) or up to a temperature at which the solvent in the reaction mixture is at reflux. The reaction product of step c2) can be isolated (including purification) by any suitable techniques known in the art. In some embodiments, the yield of step c2) is greater than about 65%, 70%, 75%, 79%, 80%, 85%, 90%, 92%, 95%, 97%, 98%, or 99%. In some embodiments, the yield of step c2) is greater than about 79%.

In some embodiments, the compound of Formula III-2, or pharmaceutically acceptable salt thereof, used herein can be prepared by:

d2) removing the Boc group from a compound of Formula V-2:

present in a suitable solvent such as $CH_2Cl_2$, EtOAc, THF, dioxane, water, or a mixture of any two or more of these solvents.

The reaction in step d2) can be carried out in a suitable solvent such as a polar solvent, for example, an ether (e.g., THF), a halogenated solvent (such as DCM), an alcohol (e.g., methanol or ethanol), or a mixture of suitable solvents. The reaction can be carried out at a suitable temperature, for example, ambient temperature (about 20-25° C.) or up to a temperature at which the solvent in the reaction mixture is at reflux. The reaction product of step d2) can be isolated as either the compound of Formula III-2, or a salt thereof, (for example, using a base such as NaOH to neutralize the acid used in the reaction of step d2)).

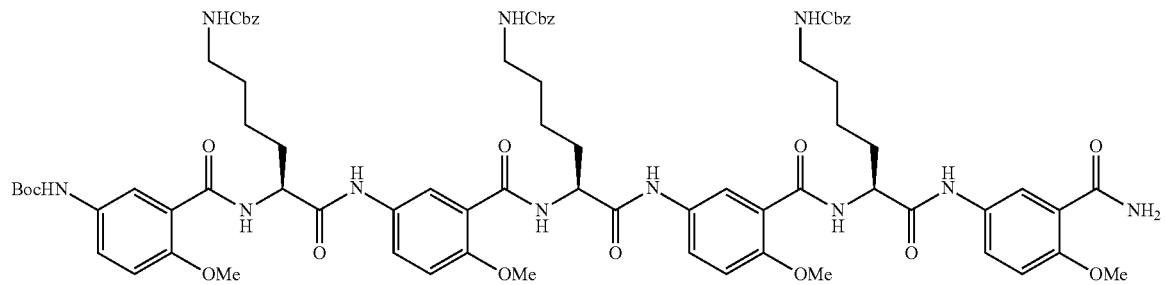

V-2 or pharmaceutically acceptable salt thereof, to form the compound of Formula III-2, or pharmaceutically acceptable salt thereof.

Removal of the Boc group in step d2) can be carried out by using a suitable reagent or suitable reagents, such as an acid (e.g., $H_3PO_4$, TFA, HCl, TsOH, or $H_2SO_4$) or TMSOTf/2,6-lutidine. In some embodiments, an acid (e.g., HCl) is used for removal of the Boc group. In some embodiments, the reagent or acid used for removal of the Boc group can be neat or In some embodiments, the yield of step d2) is greater than about 80%, 85%, 90%, 92%, 95%, 97%, 98%, or 99%. In some embodiments, the yield of step d2) is greater than about 92%.

In some embodiments, the compound of Formula V-2, or pharmaceutically acceptable salt thereof, used herein can be prepared by:

e2) reacting a compound of Formula VI-2:

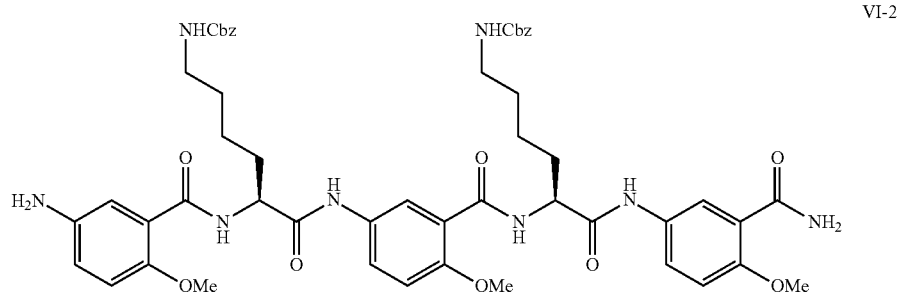 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(N)ccc3OC)ccc2OC)cc1C(N)=O]

or pharmaceutically acceptable salt thereof, with a compound of Formula VII-2:

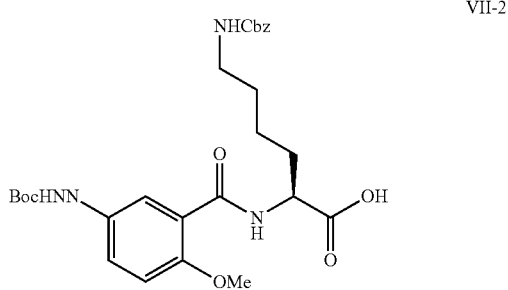

or pharmaceutically acceptable salt thereof, to form the compound of Formula V-2, or pharmaceutically acceptable salt thereof.

The reaction of step e2) can be carried out in the presence of a coupling reagent and an organic base, to form the compound of Formula V-2, or pharmaceutically acceptable salt thereof. Examples of suitable coupling reagents include, but are not limited to, BOP, HBTU, HATU, EDAC, DCC, DIC, Py-BOP, CDI, HOBt, HCTU, a suitable 1,3,5-triazine derivative, and a mixture of two or more thereof.

In some embodiments, the acid used in the coupling reaction (i.e., the compound of Formula VII-2) can be converted to a more reactive species (by using a suitable activating reagent), for example, an acid halide or a mixed anhydride. In such embodiments wherein the acid was converted to an activated species, the coupling reagent is optional for the coupling reaction. In some such embodiments, the activated species can be isolated before the coupling reaction. Examples of suitable activating reagents include, but are not limited to, alkyl chloroformate (e.g., ethyl chloroformate or isobutyl chloroformate), thionyl chloride, oxalyl chloride, cyanuric chloride, and $PBr_3$.

In some embodiments, the activating or coupling reagent in step e2) is chosen from those that prevent racemization of any chiral center present in the reactants (and/or the products). In some embodiments, the coupling reagent in step e2) includes a suitable 1,3,5-triazine derivative (e.g., 2-chloro-4,6-dimethoxy-1,3,5-triazine).

The coupling reaction in step e2) can be carried out in the presence of a suitable base. Examples of suitable bases include, but are not limited to, TEA, DIEA, NMM, DMAP, pyridine, and imidazole. In some embodiments, the base is NMM.

The reaction in step e2) can be carried out in a suitable solvent such as a polar solvent, for example, an ether (e.g., THF), a halogenated solvent (such as DCM or chloroform), or a mixture of suitable solvents. The reaction can be carried out at a suitable temperature, for example, ambient temperature (about 20-25° C.) or up to a temperature at which the solvent in the reaction mixture is at reflux. The reaction product of step e2) can be isolated (including purification) by any suitable techniques known in the art. In some embodiments, the yield of step e2) is greater than about 65%, 70%, 75%, 80%, 85%, 90%, 92%, 95%, 97%, 98%, or 99%. In some embodiments, the yield of step e2) is greater than about 80%.

In some embodiments, the compound of Formula VI-2, or pharmaceutically acceptable salt thereof, used herein can be prepared by:

f2) removing the Boc group from a compound of Formula VIII-2:

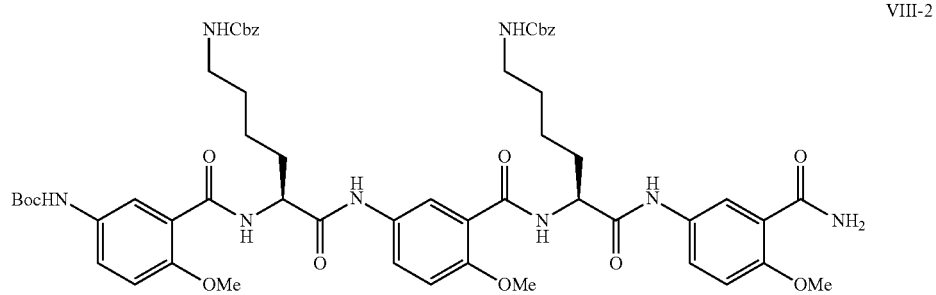 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)OC(C)(C)C)ccc3OC)ccc2OC)cc1C(N)=O]

or pharmaceutically acceptable salt thereof, under an acidic condition to form the compound of Formula VI-2, or pharmaceutically acceptable salt thereof.

Removal of the Boc group in step f2) can be carried out by using a suitable reagent or suitable reagents, such as a an acid (e.g., H$_3$PO$_4$, TFA, HCl, TsOH, or H$_2$SO$_4$) or TMSOTf/2,6-lutidine. In some embodiments, an acid (e.g., HCl) is used for removal of the Boc group. In some embodiments, the reagent or acid used for removal of the Boc group can be neat or present in a suitable solvent such as CH$_2$Cl$_2$, EtOAc, THF, dioxane, water, or a mixture of any two or more of these solvents.

The reaction in step f2) can be carried out in a suitable solvent such as a polar solvent, for example, an ether (e.g., THF), a halogenated solvent (such as DCM), an alcohol (e.g., methanol or ethanol), or a mixture of suitable solvents. The reaction can be carried out at a suitable temperature, for example, ambient temperature (about 20-25° C.) or up to a temperature at which the solvent in the reaction mixture is at reflux. The reaction product of step f2) can be isolated as either the compound of Formula VI-2, or a salt thereof, (for example, using a base such as NaOH to neutralize the acid used in the reaction of step f2)). In some embodiments, the yield of step f2) is greater than about 75%, 80%, 85%, 89%, 90%, 92%, 95%, 97%, 98%, or 99%. In some embodiments, the yield of step f2) is greater than about 89%.

In some embodiments, the compound of Formula VIII-2, or pharmaceutically acceptable salt thereof, used herein can be prepared by:

g2) reacting a compound of Formula IX-2:

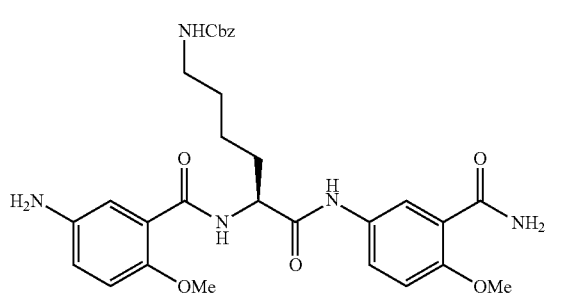

IX-2 or pharmaceutically acceptable salt thereof, with a compound of Formula VII-2:

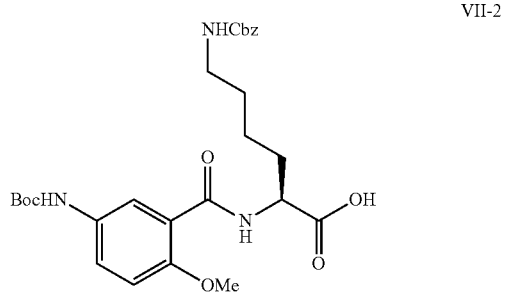 [SMILES: COc1ccc(NC(=O)OC(C)(C)C)cc1C(=O)N[C@@H](CCCCNC(=O)OCc1ccccc1)C(=O)O]

VII-2 or pharmaceutically acceptable salt thereof, to form the compound of Formula VIII-2, or pharmaceutically acceptable salt thereof.

The reaction of step g2) can be carried out in the presence of a coupling reagent and an organic base, to form the compound of Formula VIII-2, or pharmaceutically acceptable salt thereof. Examples of suitable coupling reagents include, but are not limited to, BOP, HBTU, HATU, EDAC, DCC, DIC, Py-BOP, CDI, HOBt, HCTU, a suitable 1,3,5-triazine derivative, and a mixture of two or more thereof.

In some embodiments, the acid used in the coupling reaction (i.e., the compound of Formula VII-2) can be converted to a more reactive species (by using a suitable activating reagent), for example, an acid halide or a mixed anhydride. In such embodiments wherein the acid is converted to an activated species, the coupling reagent is optional for the coupling reaction. In some such embodiments, the activated species can be isolated before the coupling reaction. Examples of suitable activating reagents include, but are not limited to, alkyl chloroformate (e.g., ethyl chloroformate or isobutyl chloroformate), thionyl chloride, oxalyl chloride, cyanuric chloride, and PBr$_3$.

In some embodiments, the activating or coupling reagent in step g2) is chosen from those that prevent racemization of any chiral center present in the reactants (and/or the products). In some embodiments, the coupling reagent in step g2) includes a suitable 1,3,5-triazine derivative (e.g., 2-chloro-4,6-dimethoxy-1,3,5-triazine).

The coupling reaction in step g2) can be carried out in the presence of a suitable base. Examples of suitable bases include, but are not limited to, TEA, DIEA, NMM, DMAP, pyridine, and imidazole. In some embodiments, the base is NMM.

The reaction in step g2) can be carried out in a suitable solvent such as a polar solvent, for example, an ether (e.g., THF), a halogenated solvent (such as DCM or chloroform), or a mixture of suitable solvents. The reaction can be carried out at a suitable temperature, for example, ambient temperature (about 20-25° C.) or up to a temperature at which the solvent in the reaction mixture is at reflux. The reaction product of step g2) can be isolated (including purification) by any suitable techniques known in the art. In some embodiments, the yield of step g2) is greater than about 80%, 85%, 90%, 92%, 95%, 97%, 98%, or 99%. In some embodiments, the yield of step g2) is greater than about 92%.

In some embodiments, the compound of Formula IX-2, or pharmaceutically acceptable salt thereof, used herein can be prepared by:

h2) removing the Boc group from a compound of Formula X-2:

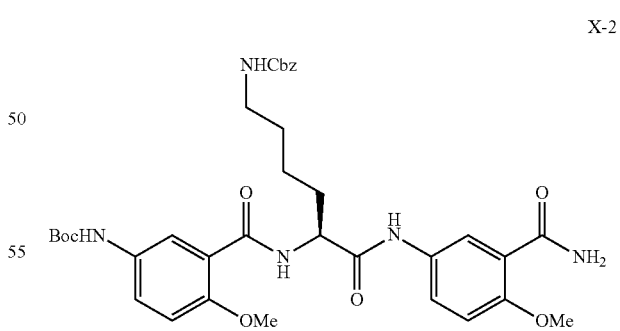

X-2 or pharmaceutically acceptable salt thereof, to form the compound of Formula IX-2, or pharmaceutically acceptable salt thereof.

Removal of the Boc group in step h2) can be carried out by using a suitable reagent or suitable reagents, such as a an acid (e.g., H$_3$PO$_4$, TFA, HCl, TsOH, or H$_2$SO$_4$) or TMSOTf/2,6-lutidine. In some embodiments, an acid (e.g., HCl) is used for removal of the Boc group. In some embodiments, the reagent or acid used for removal of the Boc group can be neat or present in a suitable solvent such as $CH_2Cl_2$, EtOAc, THF, dioxane, water, or a mixture of any two or more of these solvents.

The reaction in step h2) can be carried out in a suitable solvent such as a polar solvent, for example, an ether (e.g., THF), a halogenated solvent (such as DCM), an alcohol (e.g., methanol or ethanol), or a mixture of suitable solvents. The reaction can be carried out at a suitable temperature, for example, ambient temperature (about 20-25° C.) or up to a temperature at which the solvent in the reaction mixture is at reflux. The reaction product of step h2) can be isolated as either the compound of Formula IX-2, or a salt thereof, (for example, using a base such as NaOH to neutralize the acid used in the reaction of step h2)). In some embodiments, the yield of step h2) is greater than about 80%, 85%, 90%, 92%, 93%, 95%, 97%, 98%, or 99%. In some embodiments, the yield of step h2) is greater than about 93%.

In some embodiments, the compound of Formula X-2, or pharmaceutically acceptable salt thereof, used herein can be prepared by:

i2) reacting a compound of Formula VII-2:

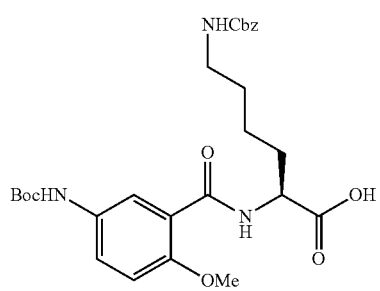

VII-2 or pharmaceutically acceptable salt thereof, with a compound of Formula XI-2:

XI-2 or pharmaceutically acceptable salt thereof, in the presence of a coupling reagent and an organic base to form the compound of Formula X-2, or pharmaceutically acceptable salt thereof.

The reaction of step i2) can be carried out in the presence of a coupling reagent and an organic base to form the compound of Formula X-2, or pharmaceutically acceptable salt thereof. Examples of suitable coupling reagents include, but are not limited to, BOP, HBTU, HATU, EDAC, DCC, DIC, Py-BOP, CDI, HOBt, HCTU, a suitable 1,3,5-triazine derivative, and a mixture of two or more thereof.

In some embodiments, the acid used in the coupling reaction (i.e., the compound of Formula VII-2) can be converted to a more reactive species (by using a suitable activating reagent), for example, an acid halide or a mixed anhydride. In such embodiments wherein the acid is converted to an activated species, the coupling reagent is optional for the coupling reaction. In some embodiments, the activated species can be isolated before the coupling reaction. Examples of suitable activating reagents include, but are not limited to, alkyl chloroformate (e.g., ethyl chloroformate or isobutyl chloroformate), thionyl chloride, oxalyl chloride, cyanuric chloride, and $PBr_3$.

In some embodiments, the activating or coupling reagent in step i2) is chosen from those that prevent racemization of any chiral center present in the reactants (and/or the products). In some embodiments, the coupling reagent in step i2) includes a suitable 1,3,5-triazine derivative (e.g., 2-chloro-4,6-dimethoxy-1,3,5-triazine).

The coupling reaction in step i2) can be carried out in the presence of a suitable base. Examples of suitable bases include, but are not limited to, TEA, DIEA, NMM, DMAP, pyridine, and imidazole. In some embodiments, the base is NMM.

The reaction in step i2) can be carried out in a suitable solvent such as a polar solvent, for example, an ether (e.g., THF), a halogenated solvent (such as DCM or chloroform), or a mixture of suitable solvents. The reaction can be carried out at a suitable temperature, for example, ambient temperature (about 20-25° C.) or up to a temperature at which the solvent in the reaction mixture is at reflux. The reaction product of step i2) can be isolated (including purification) by any suitable techniques known in the art. In some embodiments, the yield of step i2) is greater than about 65%, 70%, 75%, 80%, 85%, 88%, 90%, 92%, 95%, 97%, 98%, or 99%. In some embodiments, the yield of step i2) is greater than about 88%.

Each of the steps provided herein provides a reaction product with one or more chiral centers. In some embodiments, the reaction conditions including reagents (including, for example, solvent, acid, base, coupling reagent, activating reagent) used herein can minimize/prevent racemization of any chiral center present in any of the reactants and/or reaction products. In some embodiments, the ratio of the desired enantiomer, epimer, or diastereomer formed by each step relative to other (undesired) enantiomer, epimer, or diastereomer is greater than about 99:1, 98:2, 97:3, 96:4, 95:5. 94:6, 93:7, 92:8, 91:9, 90:10, 88:12, 85:15, 80:20, or 75:25. In some embodiments, the yield of each of the reaction products in each of the steps herein (isolated as a pure enantiomer, epimer, or diastereomer) is greater than about 75%, 80%, 85%, 90%, 91%, 92%, 93%, 94%, 95%, 96%, 97%, 98%, or 99%. In some embodiments, the yield of each of the reaction products in each of the steps herein (as a pure enantiomer, epimer, or diastereomer) is greater than about 80%, 85%, 90%, 95%, 96%, 97%, 98%, or 99%.

Some steps described herein involve a coupling reaction (coupling a carboxylic acid to an amine compound). The molar ratio of the acid to the amine compound is typically about 0.9:1.0 to about 1.1:1.0. In some embodiments, the molar ratio of the acid to the amine compound is about 0.95:1.00 to 1.05:1.00, about 0.97:1.00 to 1.03:1.00, or about 0.98:100 to 1.02:1.00. In some embodiments, the molar ratio of the acid to the amine compound is about 1.00:1.00.

The processes described herein can be monitored according to any suitable method known in the art. For example, product formation can be monitored by spectroscopic means, such as nuclear magnetic resonance spectroscopy (e.g., $^1H$ or $^{13}C$ NMR), infrared spectroscopy (IR), spectrophotometry (e.g., UV-visible), or mass spectrometry, or by chromatography such as high performance liquid chromatography (HPLC) or thin layer chromatography.

In some embodiments, the techniques above can be used to assess the purity of the reaction mixture, or of a solution containing the product of the reaction, by detecting any product formed or any reactant (to be consumed).

The reactions of the processes described herein can be carried out in air or under an inert atmosphere. Typically, reactions containing reagents or products that are substantially reactive with air can be carried out using air-sensitive synthetic techniques that are well known to the skilled artisan.

The processes described herein involve the protection and deprotection of various chemical groups. The chemistry of protecting groups can be found, for example, in Greene et al., Protective Groups in Organic Synthesis, 2d. Ed., Wiley & Sons, 1991, which is incorporated herein by reference in its entirety.

The reactions of the processes described herein can be carried out in suitable solvents and at suitable temperatures which can be readily chosen by one of skill in the art of organic synthesis. Suitable solvents can be substantially non-reactive with the starting materials (reactants), intermediates, or products at the temperatures at which the reactions are carried out, i.e., temperatures which can range from the solvent's freezing temperature to the solvent's boiling temperature. A particular reaction can be carried out in one solvent or a mixture of more than one solvent. Depending on the particular reaction step, suitable solvents for a particular reaction step can be chosen.

Each of the reaction products (compounds or salts) of the processes described herein can be isolated (including purification) by various techniques known in the art. For example, in some cases it might be desirable to isolate a reaction product by filtration and subsequent precipitation of the product from the filtrate (for example, by removal of all or part of the solvents from the filtrate, or add a different solvent). For another example, in some cases it might be desirable to isolate a reaction product by extraction with an appropriate solvent or mixture of solvents, and subsequent chromatography. Alternately, it might be desirable in some cases to directly collect a reaction product. In some embodiments, an isolated product may be further purified by washing one or more times with an appropriate solvent, or mixture of solvents. In some embodiments, a product can be further purified, for example, by recrystallization. The recrystallization can be performed with a solvent, or with a mixture of solvents. In some embodiments, a reaction product can be further purified, for example, by chromatography (for example on silica gel such as 3-mercaptopropyl ethyl sulfided silica gel). Suitable elution solvents include, but are not limited to, halogenated hydrocarbons, for example methylene chloride, alcohol (e.g. methanol), or mixtures thereof. Those skilled in the art will be able to choose other suitable solvents as elution solvents. The purity of an isolated (or purified) product can be determined by a suitable method such as using HPLC.

The present invention also provides one or more intermediates (compounds and/or salts thereof) described above, which are useful in the preparation of the compound of Formula I, or pharmaceutically acceptable salt thereof.

In order that the invention disclosed herein may be more efficiently understood, examples are provided below. It should be understood that these examples are for illustrative purposes only and are not to be construed as limiting the invention in any manner. Throughout these examples, coupling reactions and protection/deprotection reactions, and other standard reaction/workup/isolation/purification techniques, were carried out according to methods known in the art, using commercially available reagents, except where otherwise noted.

EXAMPLES

Example 1

Synthesis of Compound of Formula I or Pharmaceutically Acceptable Salt Thereof (Route I)

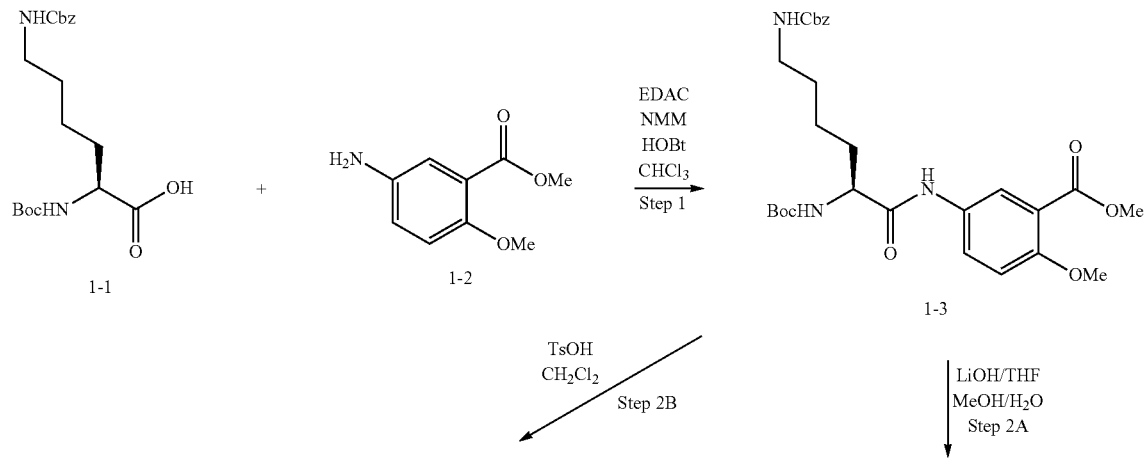

-continued
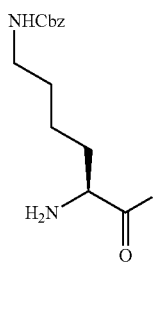 1-5
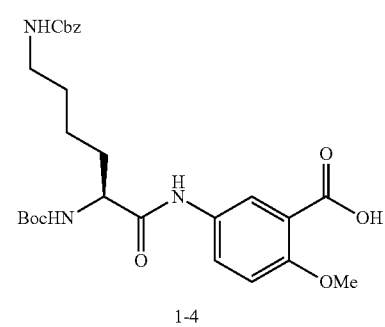 1-4
EDAC/NMM/HOBt/CHCl₃
Step 3
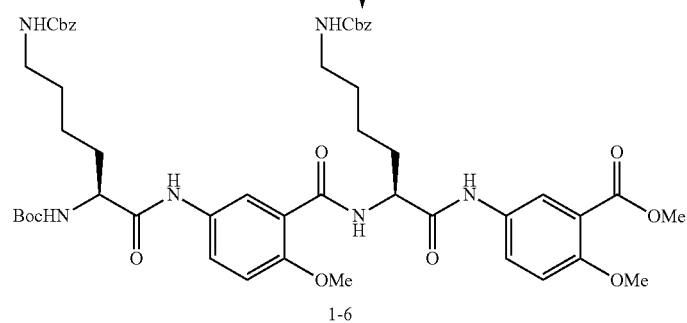 1-6
LiOH/THF
MeOH/H₂O
Step 4
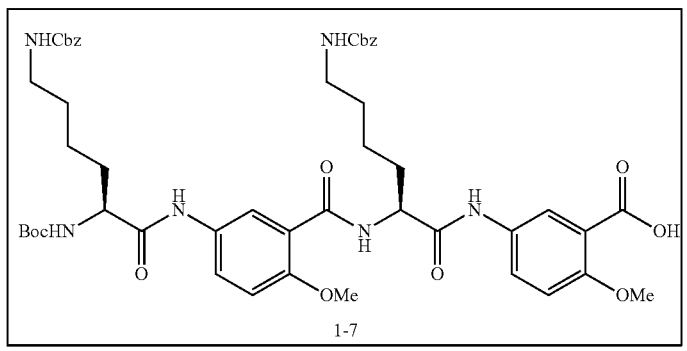 1-7
Split Compound for use in steps 5 and 7
1) Ethylchloroformate
DIEA/CHCl₃
2) NH₃
Step 5
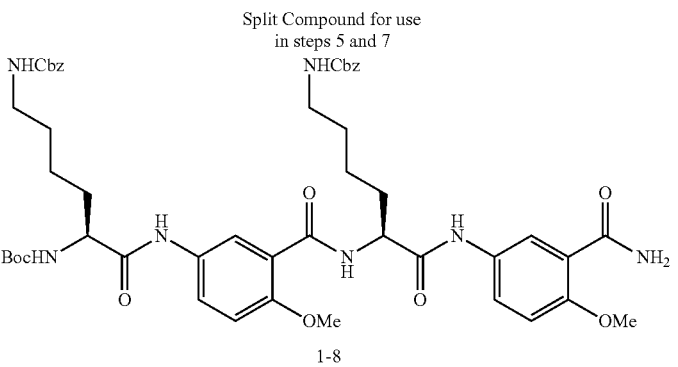 1-8
TFA/CH₂Cl₂
Step 6

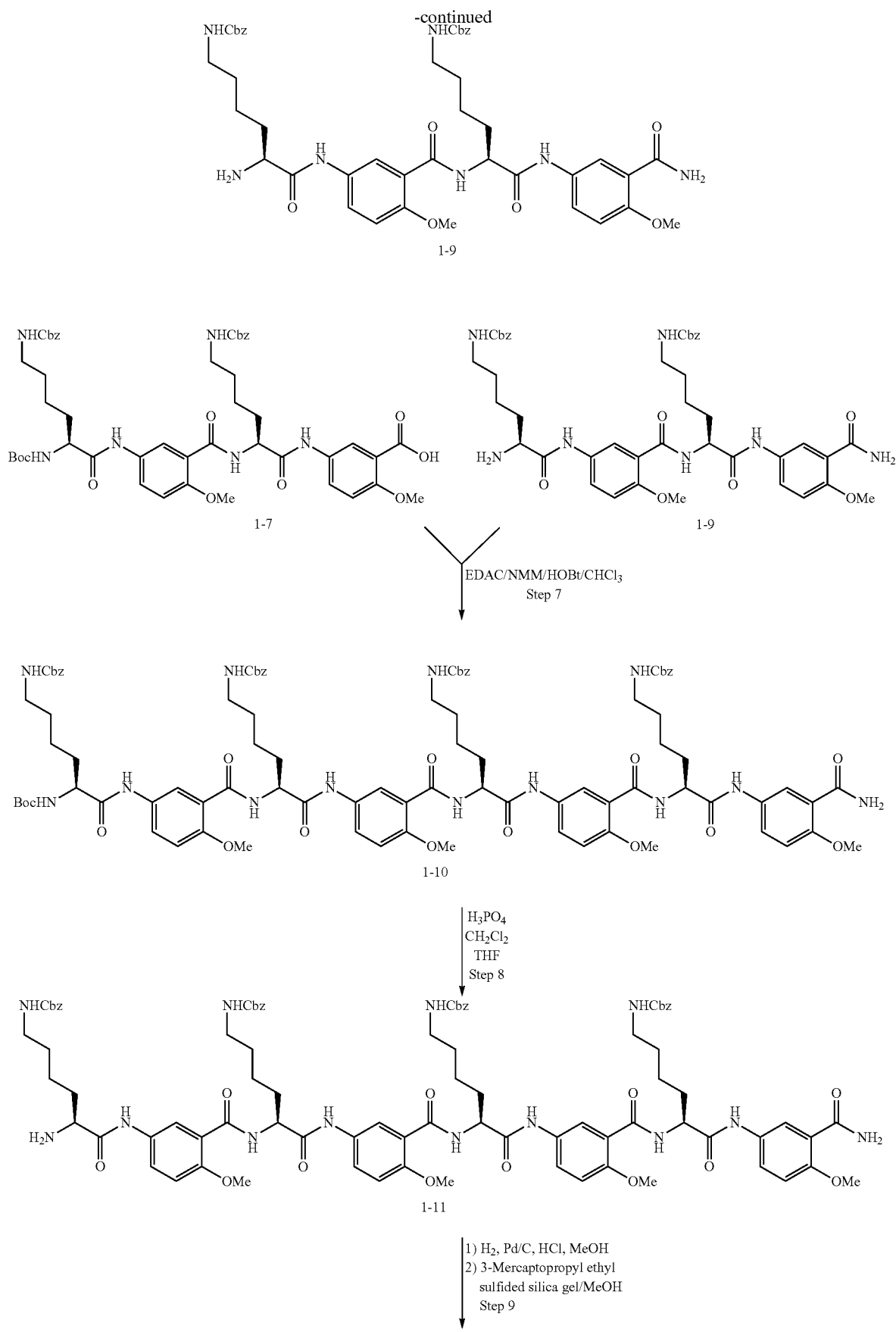

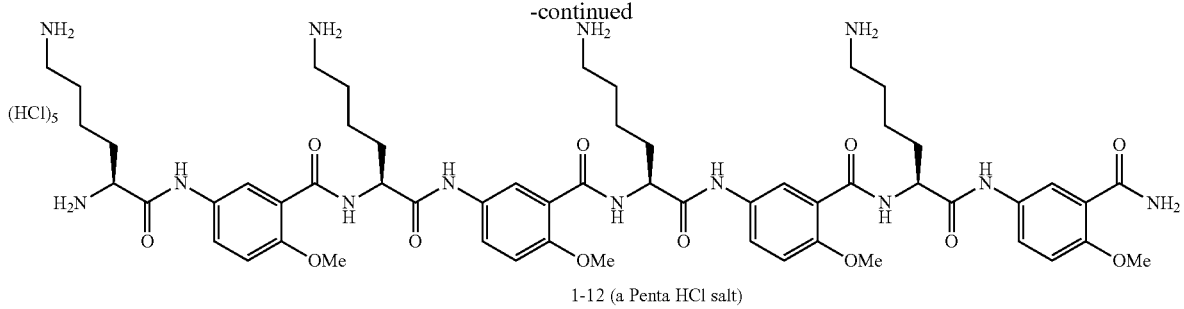

1-12 (a Penta HCl salt)

Step 1: Preparation of Compound 1-3

A mixture of compound 1-1 (1665 g, 4.379 mol, 1.0 eq), compound 1-2 (817 g, 4.51 mol, 1.03 eq), and HOBt (651 g, 4.82 mol, 1.1 eq) in 14.0 L of DCM was treated with NMM (885 g, 8.76 mol, 2.0 eq), followed by a portion wise addition of EDAC (923 g, 4.82 mol, 1.10 eq). The reaction was run at 20° C. and the reaction progress was monitored by in-process HPLC. After the reaction was completed, the reaction mixture was processed by standard extraction procedures to afford compound 1-3 (2192 g, 92.1% yield). An HPLC analysis showed the purity of compound 1-3 was 97-98%. A chiral HPLC method showed that the enantiomeric purity of compound 1-3 is was maintained (from compound 1-1) during Step 1. No undesired enantiomer was detected.

Step 2A: Preparation of Compound 1-4

A mixture of compound 1-3 (1250 g, 2.30 mol), THF (13.8 L), and MeOH (9.4 L) was cooled to 10° C. and treated dropwise over 30 minutes with 4 molar equivalents of LiOH delivered as a 5% solution in water. The reaction mixture was warmed up to room temperature with stirring and the progress was monitored by in-process HPLC. After the reaction was completed, the pH of the reaction mixture was neutralized with aqueous HCl, partially concentrated, acidified with aqueous HCl, and extracted with ethyl acetate (EtOAc). Compound 1-4 (1175 g, 96.5% yield) was obtained for which HPLC analysis showed a purity of 96%. A chiral HPLC method showed that the enantiomeric purity of compound 1-4 was maintained (from compound 1-3) during Step 2A. No undesired enantiomer was detected.

Step 2B: Preparation of Compound 1-5

A solution of compound 1-3 (2556 g, 4.70 mol) in DCM (15.0 L) was treated with p-toluenesulfonic acid (TsOH, 1073 g, 5.6 mol, 1.2 eq); and the mixture was heated to 40° C. The reaction progress was monitored by in-process HPLC. After the reaction was completed, the reaction mixture was cooled to room temperature, treated with an aqueous sodium bicarbonate solution, and then processed by standard extraction procedures to afford compound 1-5 (2065 g, 99% yield), the purity of which was determined to be 96.4% by HPLC analysis.

Step 3: Preparation of Compound 1-6

A mixture of compound 1-5 (1030 g, 2.32 mol, 1.05 eq), HOBt (601 g, 4.45 mol, 2.0 eq), and NMM (670 g, 6.63 mol, 3.0 eq) in chloroform (17.6 L) was treated with a solution of EDAC (511 g, 2.65 mol, 1.2 eq) in chloroform (2.0 L). This mixture was treated by drop wise addition of a solution of compound 1-4 (1170 g, 2.21 mol, 1.0 eq) and NMM (337 g, 3.33 mol, 1.5 eq) in chloroform (4.2 L) and the resultant reaction mixture was stirred at 20-25° C. The reaction progress was monitored by the in-process HPLC method. After the reaction was completed, the reaction mixture was processed by standard extraction procedures. The solid foam obtained showed excess weight, and a purity of approximately 88% by HPLC analysis. The solid foam obtained was subjected to crystallization from heptane/EtOAc. Compound 1-6 (1287 g, 61% yield) was obtained and its purity was determined to be 97.2% by HPLC analysis.

Step 4: Preparation of Compound 1-7

A mixture of compound 1-6 (2516 g, 2.63 mol), THF (16.6 L), and MeOH (10.9 L) was cooled to 10° C. and treated drop wise over 45 minutes with 4 equivalents of LiOH delivered as a 5% solution in water. The reaction mixture was warmed up to room temperature with stirring, and the reaction progress was monitored by in-process HPLC. After the reaction was completed, the reaction mixture was neutralized with aqueous HCl, partially concentrated, acidified with aqueous HCl, and extracted with EtOAc. Compound 1-7 (quantitative yield, 2813 g of the crude product) was obtained and its purity was determined to be 94.7% by HPLC analysis. The crude product was directly used in the next step without further purification.

Step 5: Preparation of Compound 1-8

A solution of compound 1-7 [1490 g of the crude product prepared in Step 4 above, assumed to be the equivalent of 1297 g (1.38 mol) of pure compound 1-7] in chloroform (13.0 L) was cooled to 10° C. and treated with ethyl chloroformate (302 g, 2.78 mol, 2.0 eq) in one portion followed by drop wise addition of DIEA (357 g, 2.76 mol, 2.0 eq.) while monitoring the internal temperature. The reaction mixture was warmed up to ambient temperature with stirring. The reaction progress was monitored to show a complete conversion to the reactive mixed anhydride intermediate by HPLC analysis of a sample that was quenched by 0.5 M ammonia in dioxane and assessed for formation of compound 1-8 and the consumption of compound 1-7. After complete conversion of the acid 1-7 to the anhydride intermediate, the reaction mixture was cooled to 0° C. and treated through a bubbler with ammonia gas (151 g, 8.8 mol, 6.4 eq.) while monitoring the internal temperature. The reaction progress was monitored by in-process HPLC. After the reaction was completed, the reaction mixture was quenched with water and processed by standard extraction procedures. Compound 1-8 (quantitative yield, 1322 g of the crude product) was obtained and its purity was determined to be 93.2% by HPLC analysis. The crude product was directly used in the next step without further purification.

Step 6: Preparation of Compound 1-9

A solution of compound 1-8 (1322 g of the crude product prepared in Step 5 above, assumed to be the equivalent of 1298 g (1.38 mol) of pure compound 1-8) in DCM (4.4 L) was cooled to 0° C. and treated drop wise with TFA (2.1 L, 28 mol, 20 eq.) while maintaining the internal temperature to be below about 10° C. The reaction mixture was warmed up to ambient temperature with stirring. The reaction progress was monitored by in-process HPLC. After the reaction was completed, the reaction mixture was rapidly cooled to −20° C.

then quenched by addition over 30 minutes to a rapidly stirred −5° C. mixture of NaOH (22 eq.) in water (9.6 L) and DCM (4.5 L). The addition rate was such that the internal temperature of the mixture was maintained at below about 10° C. The quenched reaction mixture was processed by standard extraction procedures to afford compound 1-9 (1152 g, 99% yield), and its purity was determined to be 85.0% by HPLC analysis.

Step 7: Preparation of Compound 1-10

A mixture of compound 1-7 (981 g, 1.04 mol, 1.00 eq), compound 1-9 (894 g, 1.06 mol, 1.02 eq), and HOBt (288 g, 2.1 mol, 2.0 eq) in chloroform (17.9 L) was treated with a solution of EDAC (240 g, 1.25 mol, 1.2 eq) in chloroform (2.2 L) followed by an addition of NMM (161 g, 1.6 mol, 1.5 eq.). The reaction mixture was stirred at 20-25° C. and the reaction progress was monitored by in-process HPLC. After the reaction was completed, the reaction mixture was processed by standard extraction procedures to afford compound 1-10 (quantitative yield, 1840 g of crude product) as a solid. The purity of the crude product 1-10 was determined to be 80.0% by HPLC analysis. The crude product was subjected to a first recrystallization from 2-propanol/methanol followed by a second recrystallization from chloroform/2-propanol to afford a purified compound 1-10 (1280 g, 69.8% yield), and its purity was determined to be 95.1% by HPLC analysis.

Step 8: Preparation of Compound 1-11

A mixture of DCM (3.1 L), THF (3.1 L), and phosphoric acid (5323 g, 85%, 46.2 mol, 65 eq.) was prepared and the purified compound 1-10 prepared in Step 7 (1248 g, 0.707 mol) was added portion wise over 30 minutes. The reaction mixture was stirred at 20-25° C. and the reaction progress was monitored by in-process HPLC. After the reaction was completed, the reaction mixture was quenched with aqueous NaOH (the pH of the reaction mixture was adjusted to 8-9) and processed by standard extraction procedures to afford compound 1-11 (quantitative yield, 1323 g of crude product). The purity of the crude product was determined to be 90.5% by HPLC analysis.

The crude product 1-11 was purified by silica gel chromatography. The purification process used 30 g of silica gel (230-400 mesh) per gram of the crude product 1-11. 1% MeOH/DCM to 10% MeOH/DCM (in gradient) were used as elution solvents. After the chromatography, of 460 g (39%) of purified compound 1-11 was obtained. The purity of the purified compound 1-11 was determined to be 97.5% by HPLC analysis.

Step 9: Preparation of Penta HCl Salt of the Compound of Formula I (1-12)

A mixture of the purified compound 1-11 prepared by Step 8 (417 g, 0.251 mol), 10 wt % palladium on carbon (167 g), MeOH (16.7 L), and HCl (5.0 eq., in a 7.2 wt % aqueous solution) was subjected to hydrogen gas at 70 psi pressure. The reaction mixture was agitated at 25° C. and the reaction progress was monitored by in-process HPLC. After the reaction was completed, the reaction mixture was filtered and concentrated by co-distillation with acetonitrile to afford a solid product that was slurried in MTBE, filtered, and dried. The crude product 1-12 was obtained (300 g, 91% yield) as a penta HCl salt of the compound of Formula I. The purity of the crude product was determined to be 97.9% by HPLC analysis.

The crude product 1-12 was further purified. A solution of the crude product 1-12 (274 g, 0.209 mol) in MeOH (13.9 L) was treated with 28 g of 3-mercaptopropyl ethyl sulfided silica gel and stirred for 90 minutes. The mixture was filtered and concentrated by co-distillation with acetonitrile to afford a solid product that was slurried in MTBE, filtered, and dried. HPLC analyses were performed to determine the purity of the salt 1-12 and the level of remaining palladium in the product. This purification process was repeated one more time on the purified product obtained previously (266 g, 0.203 mol) and the second purification process resulted in 219 g (82% recovery) of salt 1-12 that has purity of 97.9% and a Pd level of 2.7 ppm.

Example 2

Synthesis of Compound of Formula I or Pharmaceutically Acceptable Salt Thereof (Route II)

Scheme 2

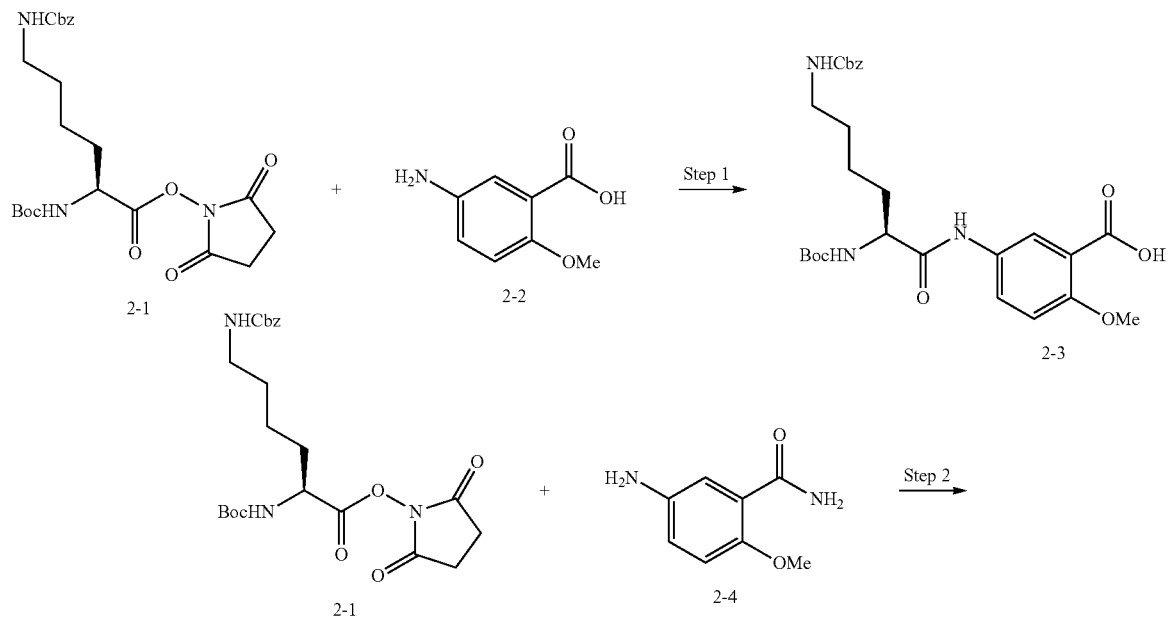

-continued
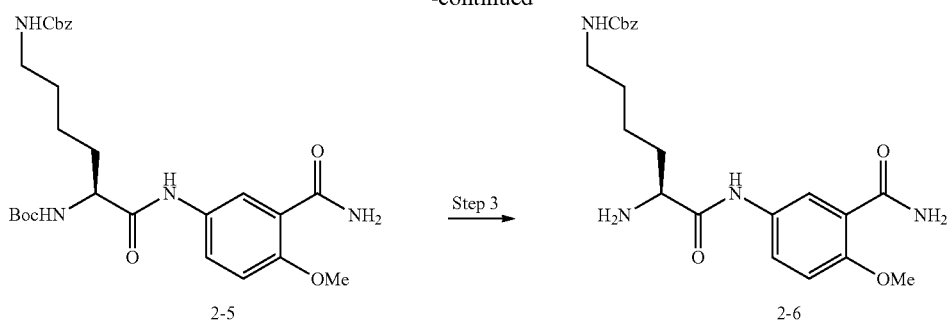
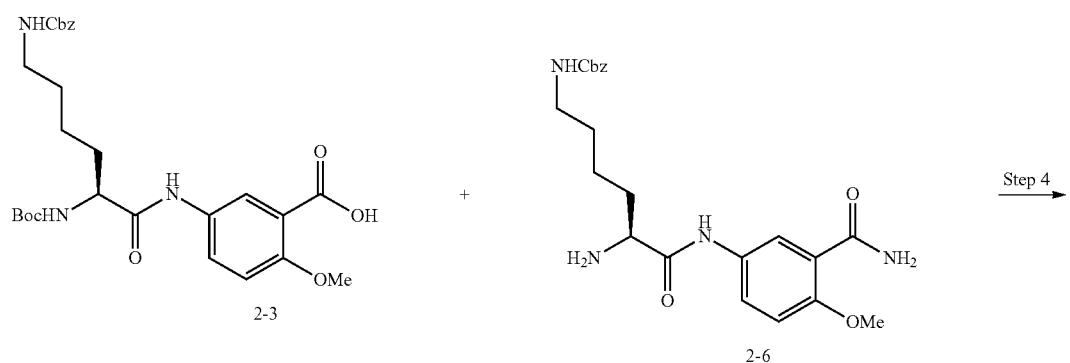
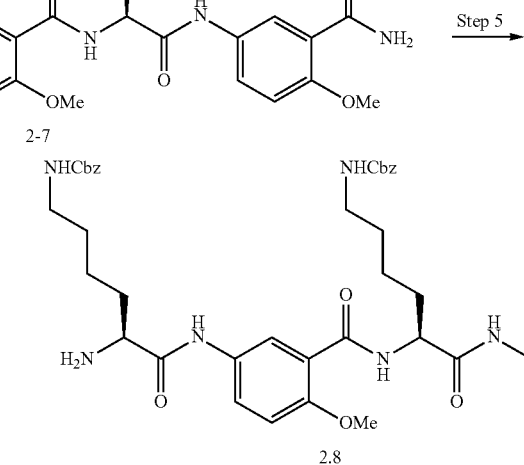
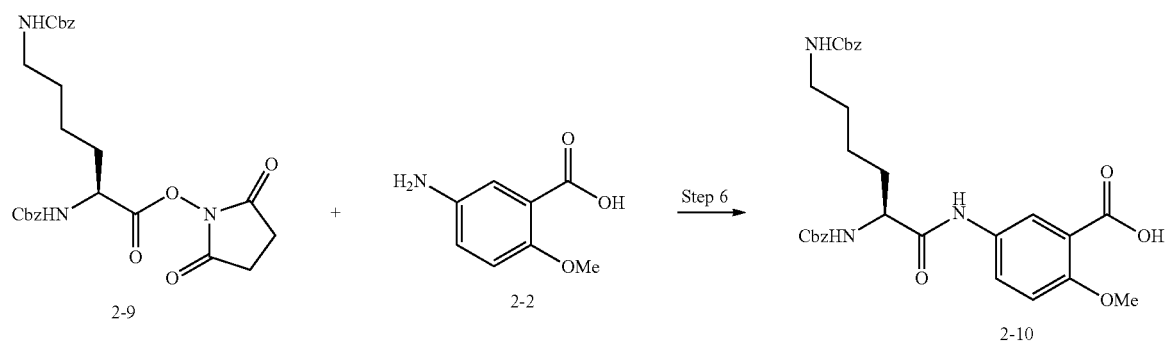

-continued
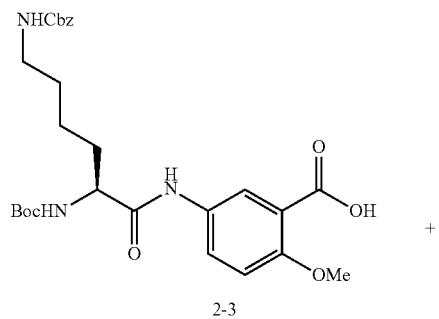
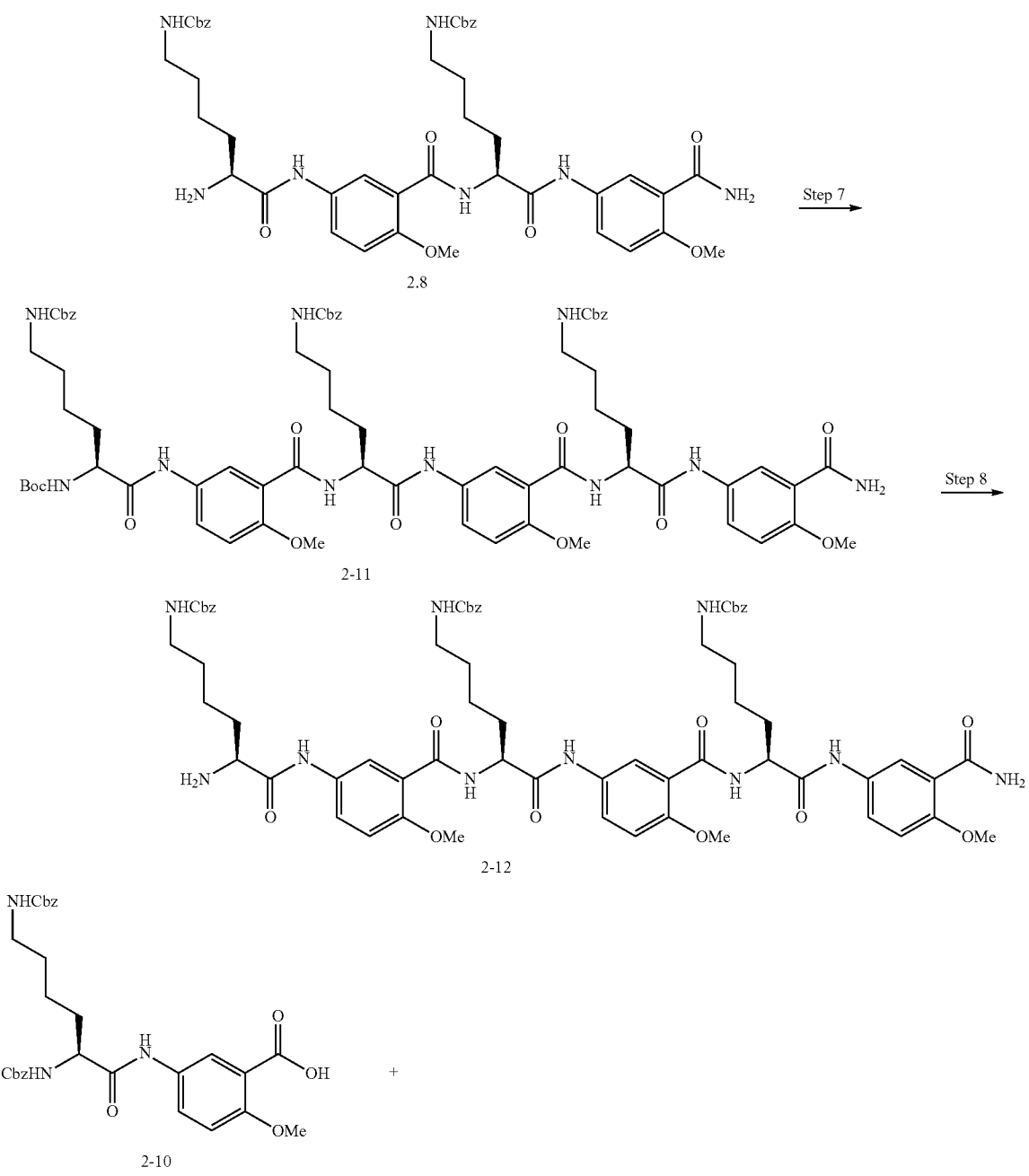

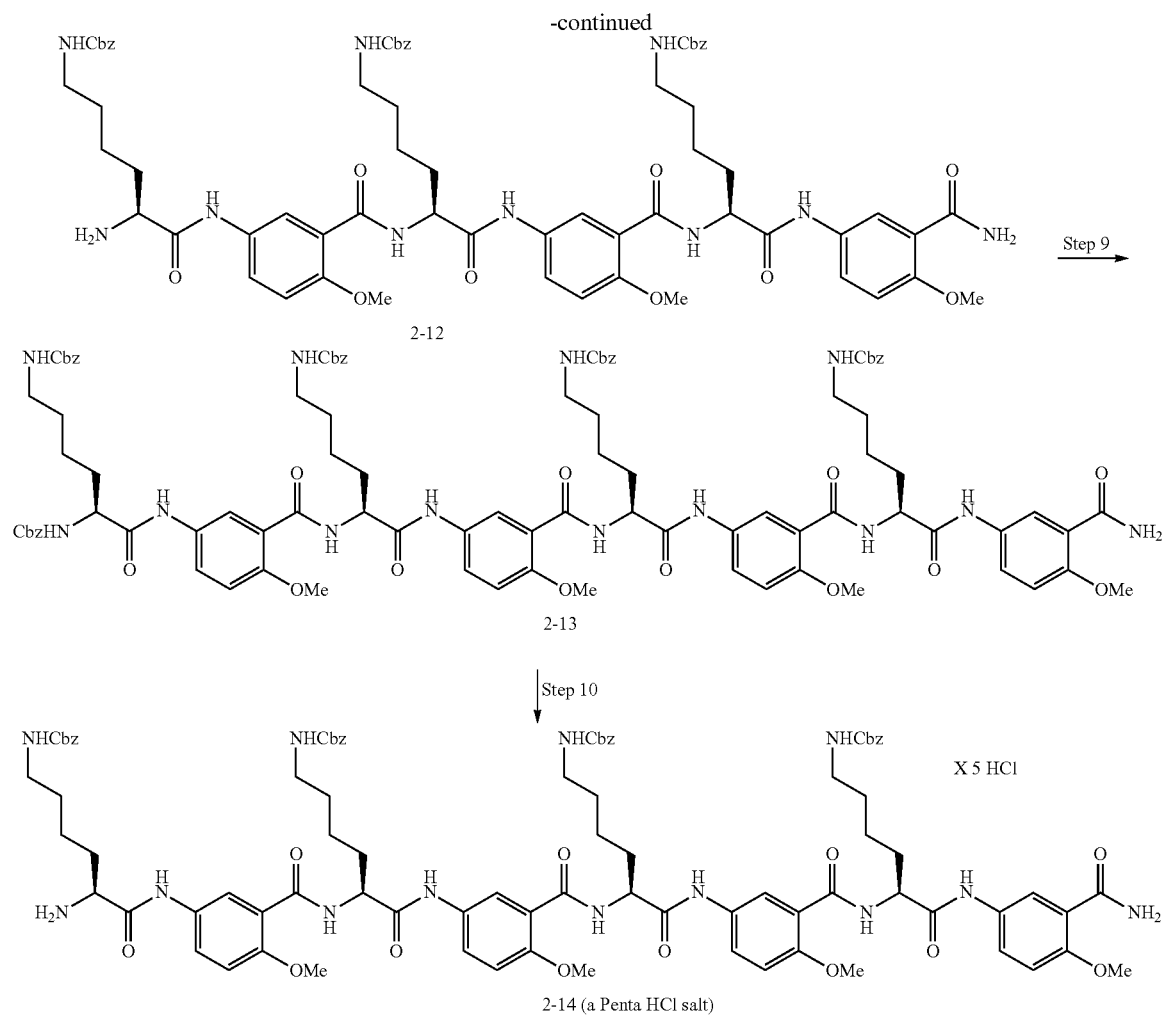

2-14 (a Penta HCl salt)

Step 1: Preparation of Compound 2-3

A mixture of compound 2-1 (0.477 g, 1.00 mmol) and compound 2-2 (0.200 g, 1.20 mmol) in ethyl acetate (5.0 mL) was stirred vigorously while heating to a gentle reflux. The reaction mixture, initially a suspension, became a solution but over time some solid deposited on the reaction flask wall. After 24 hours the reaction was found to be complete by HPLC analysis. The reaction mixture was cooled to room temperature, diluted with ethyl acetate, and serially extracted with distilled water until the resultant aqueous wash had a neutral pH. The organic fraction was dried over $Na_2SO_4$, filtered, and concentrated to provide 0.552 g (greater than theoretical yield due to trapped solvent) of viscous orange syrup that MS/HPLC analysis showed to be 99% compound 2-3. This crude material was purified by crystallization from ethyl acetate to obtain a first crop of 0.345 g (65%) of compound 2-3 as a white powder that had a purity of >99% by MS/HPLC analysis.

Step 2: Preparation of Compound 2-5

A mixture of compound 2-1 (0.477 g, 1.00 mmol) and compound 2-4 (0.200 g, 1.20 mmol) in chloroform (5.0 mL) was stirred vigorously while heating to a gentle reflux. The reaction mixture, initially a suspension, became a solution but over time some solid deposited on the reaction flask wall. After 24 hours the reaction was found to be complete by HPLC analysis. The reaction mixture was cooled to room temperature and concentrated. The residue was dissolved in ethyl acetate and the solution was extracted with distilled water, extracted with saturated $NaHCO_3$, dried over $Na_2SO_4$, filtered, and concentrated. Obtained 0.544 g (103% due to trapped solvent) of viscous yellow oil that MS/HPLC analysis showed to be >99% compound 2-5.

Step 3: Preparation of Compound 2-6

Compound 2-5 (0.127 g, 0.240 mmol) was treated with 3.0 mL of a 1:2 (v/v) solution of trifluoroacetic acid in dichloromethane (cooled at 0° C.) and the mixture was warmed to room temperature over 90 minutes. The reaction mixture was cooled in an ice bath for 30 minutes and treated with 20 mL of 0° C. tert-butyl methyl ether, which caused extensive precipitation of an off-white solid. After residence in the ice bath for one hour, collected the precipitate by suction filtration. The collected solid, which quickly became a syrup due to is hygroscopicity, was dissolved in acetonitrile and concentrated. The residue was extracted between ethyl acetate and saturated $NaHCO_3$ and the organic portion was dried over $Na_2SO_4$, filtered, and concentrated. Obtained 0.091 g (88%) of yellow syrup that MS/HPLC analysis showed was compound 2-6 with a purity of 97%.

Step 4: Preparation of Compound 2-7

A mixture of compound 2-3 (0.158 g, 0.298 mmol) and compound 2-6 (0.127 g, 0.296 mmol) in 25 mL of dichloromethane was treated sequentially with HOBt (0.081 g, 0.60 mmol), EDAC (0.069 g, 0.36 mmol), and N-methylmorpholine (50 µL, 0.45 mmol). The reaction mixture was stirred at room temperature and monitored by MS/HPLC. After 40 hours the reaction mixture was diluted with dichloromethane and extracted with distilled water, saturated NaHCO$_3$, and brine. The organic portion was dried over Na$_2$SO$_4$, filtered, and concentrated. Obtained 0.284 (102% of theoretical due to trapped solvent) of beige residue that MS/HPLC analysis showed was compound 2-7 with a purity of 94%.

Step 5: Preparation of Compound 2-8

Compound 2-7 (0.278 g, 0.296 mmol) was treated with 3.0 mL of a 0° C. 1:2 (v/v) solution of trifluoroacetic acid in dichloromethane and the mixture was warmed to room temperature over 90 minutes. The reaction mixture was cooled in an ice bath for 30 minutes and treated with 20 mL of 0° C. tert-butyl methyl ether, which caused extensive precipitation of an off-white solid. After residence in the ice bath for one hour, collected the precipitate by suction filtration. The collected solid, which quickly became a syrup due to is hygroscopicity, was dissolved in acetonitrile and concentrated. The residue was extracted between dichloromethane and saturated NaHCO$_3$ and the organic portion was dried over Na$_2$SO$_4$, filtered, and concentrated. Obtained 0.226 g (91%) of orange syrup that MS/HPLC analysis showed was compound 2-8 with a purity of 95%.

Step 6: Preparation of Compound 2-10

A mixture of compound 2-9 (0.064 g, 0.125 mmol) and 2-2 (0.025 g, 0.15 mmol) in ethyl acetate (5.0 mL) was stirred vigorously while heating to a gentle reflux. The reaction mixture was a suspension with very fine particles. The reaction progress was monitored by MS/HPLC and found to be complete after 67 hours. The reaction mixture was cooled to room temperature, diluted with ethyl acetate, and serially extracted with distilled water until the resultant aqueous wash had a neutral pH. The organic fraction was dried over Na$_2$SO$_4$, filtered, and concentrated to obtain 0.065 g (92%) of beige waxy residue that MS/HPLC analysis showed to be 89% compound 2-10. This crude material was purified by crystallization from ethyl acetate. Obtained a first crop of 0.040 g (57%) of compound 2-10 as a white powder that had a purity of >99% by MS/HPLC analysis.

Step 7: Preparation of Compound 2-11

A mixture of compound 2-3 (0.058 g, 0.11 mmol) and compound 2-8 (0.092 g, 0.11 mmol) in 10 ml, of dichloromethane was treated sequentially with HOBt (0.030 g, 0.22 mmol), EDAC (0.025 g, 0.13 mmol), and N-methylmorpholine (18 µL, 0.16 mmol). The reaction mixture was stirred at room temperature and monitored by MS/HPLC. After 40 hours the reaction mixture was diluted with dichloromethane and extracted with distilled water, saturated NaHCO$_3$, and brine. The organic portion was dried over Na$_2$SO$_4$, filtered, and concentrated. Obtained 0.145 (98%) of beige residue that MS/HPLC analysis showed was compound 2-11 with a purity of 96%.

Step 8: Preparation of Compound 2-12

Compound 2-11 (0.145 g, 0.107 mmol) was treated with 3.0 mL of a 0° C. 1:2 (v/v) solution of trifluoroacetic acid in dichloromethane and the mixture was warmed to room temperature over 90 minutes. The reaction mixture was cooled in an ice bath for 30 minutes and treated with 20 mL of 0° C. tert-butyl methyl ether, which caused extensive precipitation of an off-white solid. After residence in the ice bath for one hour, collected the precipitate by suction filtration. The collected solid was extracted between dichloromethane and saturated NaHCO$_3$ and the organic portion was dried over Na$_2$SO$_4$, filtered, and concentrated. Obtained 0.125 g (93%) of tan residue that MS/HPLC analysis showed was compound 2-12 with a purity of 92%.

Step 9: Preparation of Compound 2-13

A mixture of compound 2-10 (0.097 g, 0.17 mmol) and compound 2-12 (0.215 g, 0.17 mmol) in 16 mL of dichloromethane was treated sequentially with HOBt (0.046 g, 0.34 mmol), EDAC (0.040 g, 0.21 mmol), and N-methylmorpholine (28 µL, 0.25 mmol). The reaction was stirred at room temperature and monitored by MS/HPLC. After 24 hours the reaction was diluted with dichloromethane and extracted with distilled water, saturated NaHCO$_3$, and brine. The organic portion was dried over Na$_2$SO$_4$, filtered, and concentrated. Obtained 0.281 g (91%) of beige residue that MS/HPLC analysis showed was compound 2-13 with a purity of 82%.

Step 10: Preparation of Compound 2-14

A sample of compound 2-13 that was 82% pure by MS/HPLC (0.281 g, 0.156 mmol) was dissolved in 60 mL of a 5:1 (v/v) mix of methanol and dioxane. The solution was treated with 0.78 mL of cold 1.0 M HCl (5 eq), degassed with argon for 10 minutes, and treated with 100 mg of 10% Pd/C. The resulting mixture was subjected to 75 psi H$_2$ on a Paar shaker for 64 hours. MS/HPLC showed complete conversion to compound 2-14. The reaction mixture was suction filtered through a Celite pad over a sintered glass frit and the filtrate was further filtered through a 0.45 µm frit. The resultant filtrate was concentrated to afford 0.220 g of yellow solid. From this material 0.210 g was treated with 21.0 mL of a 4:1:1 (v/v) mixture of n-butanol, methanol, and water and heated with vigorous stirring to 60° C. for 27 hours. The mixture was cooled to 0° C. and filtered. Obtained 0.103 g (64%) of compound 2-14 as a beige powder with a purity of 98%.

Example 3
Synthesis of Compound of Formula I or Pharmaceutically Acceptable Salt Thereof (Route III)
Scheme 3
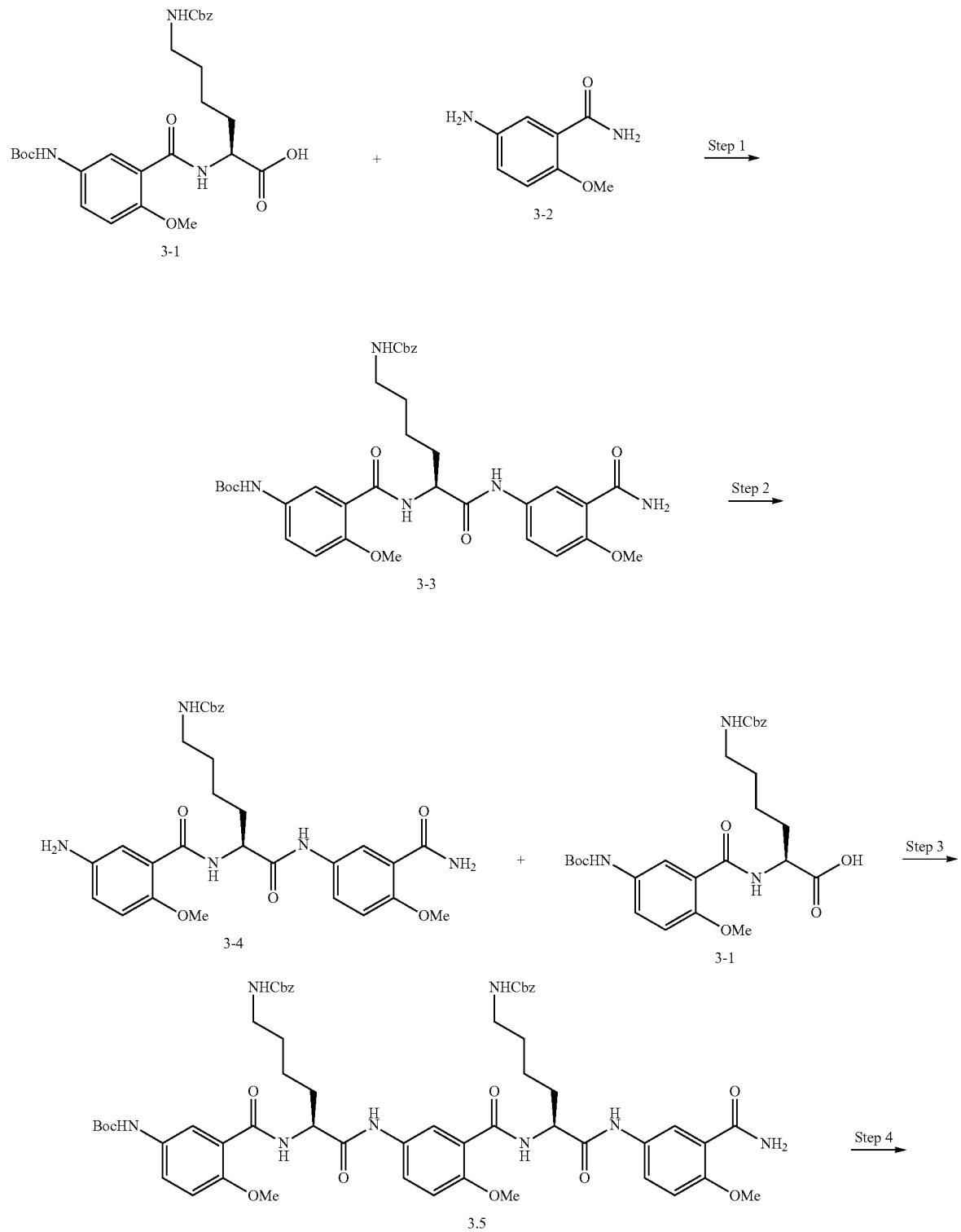

-continued
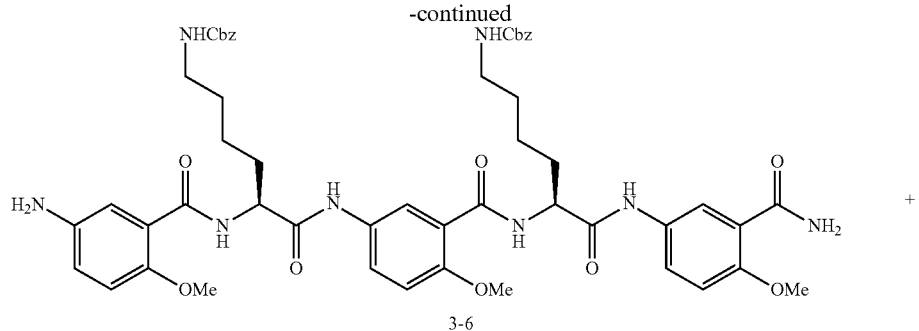
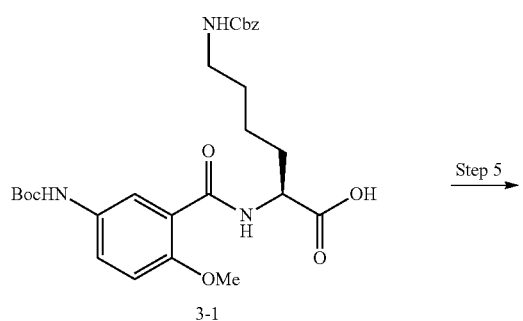
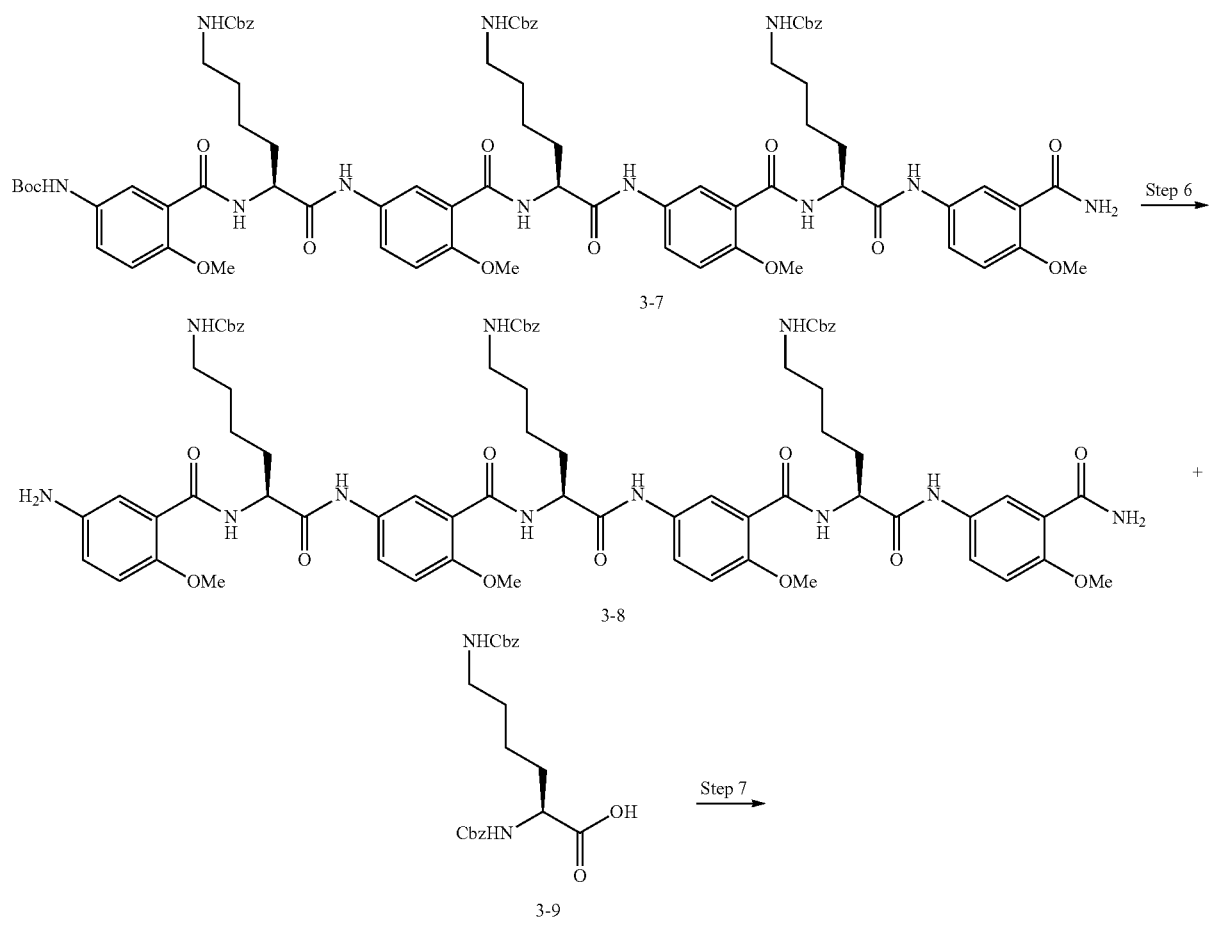

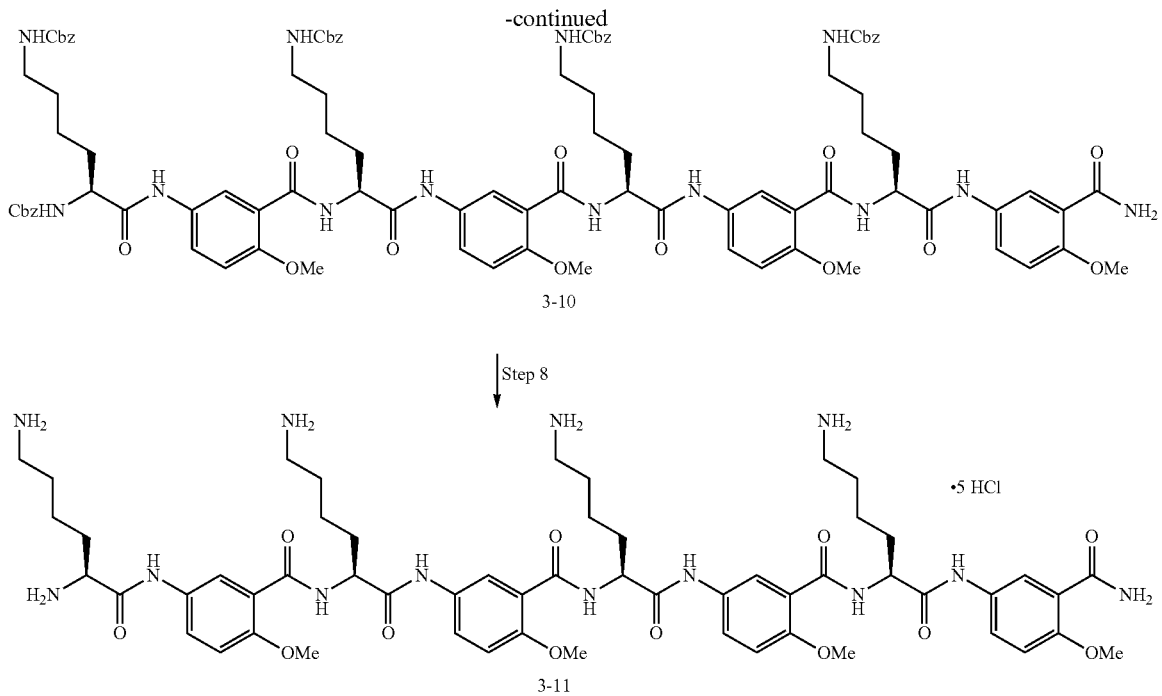

3-10

Step 8

3-11

Step 1: Preparation of Compound 3-3

A mixture of 2-chloro-4,6-dimethoxy-1,3,5-triazine (1.77 g, 1.0 mmol, 1.0 eq.) was stirred in anhydrous THF (200 mL), and N-Methylmorpholine (2.02 g, 2.0 mmol, 2.0 eq.) was added. The resulting mixture was stirred at room temperature for 30 minutes, and then compound 3-1 (5.29 g, 1 mmol, 1 eq., purchased from Astatech, Inc.) and compound 3-2 (purchased from J & W Pharmlab., 1.66 g, 1 mmol, 1.0 eq.) were added. The resulting mixture was stirred at room temperature for 24 hours. Then the solvent was evaporated under vacuum. Water (250 mL) was added and the mixture was stirred for 4 hours. After filtration, the solid was washed with water (3×100 mL) and stirred in water (250 mL) for additional 4 hours. The filtration and washing procedure was repeated twice. Then the solid was dried in the air and then under vacuum. The crude product was purified by crystallization in toluene. Compound 3-3 was obtained (6.0 g, 88% yield). The molecular ion was 678.2 (M+1).

Step 2: Preparation of Compound 3-4

Compound 3-3 (6.78 g, 1 mmol, 1.0 eq.) was dissolved in 100 ml ethyl acetate; and 6.0 ml concentrated HCl solution (72 mmol, 72.0 eq.) was added slowly during a 5-minute period. The solution was stirred at room temperature for another 10 minutes, and then 100 ml saturated aqueous $Na_2CO_3$ solution was added slowly. The precipitate formed was filtered and washed with 100 ml water thrice. Then the solid was dried in the air and then under vacuum. The crude product was purified by crystallization in ethyl acetate and compound 3-4 (5.4 g) was obtained in 93.4% yield. The molecular ion was 578.3 (M+1).

Step 3: Preparation of Compound 3-5

2-Chloro-4,6-dimethoxy-1,3,5-triazine (0.89 g, 0.5 mmol, 1 eq.) was stirred in anhydrous THF (200 mL). N-Methylmorpholine (1.01 g, 1.0 mmol, 2.0 eq.) was added. The resulting mixture was stirred at room temperature for 30 minutes, then Compound 3-1 (2.65 g, 0.5 mmol, 1.0 eq.) and compound 3-4 (2.89 g, 0.5 mmol., 1.0 eq.) were added. The mixture was stirred at room temperature for 24 hours. Then the solvent was evaporated completely under vacuum. Water (250 mL) was added and the mixture was stirred for 4 hours. After filtration, the solid obtained was washed with water (3×100 mL) and stirred in water (250 mL) for another 4 hours. The filtration and washing procedure were repeated twice. Then the solid was dried in the air and then under vacuum. The crude product was purified by crystallization in toluene. Compound 3-5 (5.0 g) was obtained in 92% yield. The molecular ion was 1089.5 (M+1).

Step 4: Preparation of Compound 3-6

Compound 3-5 (5.05 g, 0.5 mmol, 1.0 eq.) was dissolved in 100 ml ethyl acetate. A concentrated HCl solution (6.0 mL, 72.0 mmol, 144 eq.) was added slowly during a 5-minute period. The resulting solution was stirred at room temperature for another 10 minutes, and then 100 ml saturated $Na_2CO_3$ aqueous solution was added slowly. The precipitate formed was filtered and washed with 100 ml water thrice. Then the solid was dried in the air and then under vacuum. The crude product was purified by crystallization in ethyl acetate and compound 1-6 (4.4 g) was obtained in 89% yield. The molecular ion was 989.4 (M+1).

Step 5: Preparation of Compound 3-7

2-Chloro-4,6-dimethoxy-1,3,5-triazine (0.59 g, 0.33 mmol, 1.0 eq.) was stirred in anhydrous THF (100 mL). N-Methylmorpholine (0.70 g, 0.66 mmol, 2.0 eq.) was added. The resulting mixture was stirred at room temperature for 30 minutes, then compound 3-1 (1.70 g, 0.33 mmol, 1.0 eq.) and compound 3-6 (3.20 g, 0.33 mmol, 1.0 eq.) were added. The mixture was stirred at room temperature for 24 hours. Then the solvent was evaporated completely under vacuum. Water (150 mL) was added and the mixture was stirred for 4 hours. After filtration, the solid obtained was washed with water (3×100 mL) and stirred in water (250 mL) for additional 4 hours. The filtration and washing procedure were repeated twice. Then the solid obtained was dried in the air and then under vacuum. The crude product was purified by crystallization in toluene. Compound 3-7 (4.0 g) was obtained in 80% yield. The molecular ion was 1500.2 (M+1).

Step 6: Preparation of Compound 3-8

Compound 3-7 (5.0 g, 0.3 mmol, 1.0 eq.) was dissolved in 100 ml dichloromethane. A concentrated HCl solution (3 mL, 36.0 mmol, 120.0 eq.) was added slowly during a 5-minute period. The resulting solution was stirred at room temperature for another 10 minutes, and then 100 ml saturated $Na_2CO_3$ aqueous solution was added slowly. The precipitate was filtered and washed with 100 mL water thrice. Then the solid obtained was dried in the air and then under vacuum. The crude product was purified by crystallization in ethyl acetate and compound 3-8 (4.2 g) was obtained in 92% yield. The molecular ion was 1400.3 (M+1).

Step 7: Preparation of Compound 3-10

2-Chloro-4,6-dimethoxy-1,3,5-triazine (0.177 g, 0.10 mmol, 1.0 eq.) was stirred in anhydrous THF (50 mL). N-Methylmorpholine (0.202 g, 0.2 mmol, 2.0 eq.) was added. The resulting mixture was stirred at room temperature for 30 minutes. Then compound 3-9 (0.414 g, 0.1 mmol, 1.0 eq.) and compound 3-8 (1.40 g 0.1 mmol, 1.0 eq.) were added. The resulting mixture was stirred at room temperature for 24 hours. Then the solvent was evaporated completely under vacuum. Water (150 mL) was added and the mixture was stirred for 4 hours. After filtration, the solid obtained was washed with water (3×100 mL) and stirred in water (100 mL) for 4 hours. The filtration and washing procedure were repeated twice. Then the solid obtained was dried in the air and then under vacuum. The crude product was purified by silica gel column chromatography. Compound 3-10 (1.50 g) was obtained in 79% yield. The molecular ion was 1796 (M+1).

Step 8: Preparation of Salt 3-11

Compound 3-10 (1.80 g, 0.1 mmol, 1.0 eq.) dissolved in 10 ml dichloromethane and 10 ml methanol, and the solution was degassed with argon for 5 minutes. 10% Pd/C (250 mg) was added. Then it was followed by an addition of 5 ml 1 N HCl solution. The reaction mixture is then subjected to 70 PSI $H_2$ overnight. The catalyst was filtered with celite and the solvent in the filtrate was removed. Penta HCl salt of the compound of Formula I (salt 3-11, 0.90 g) was obtained in 87% yield. The molecular ion was 1126.4 (M+1).

Reference Example 1

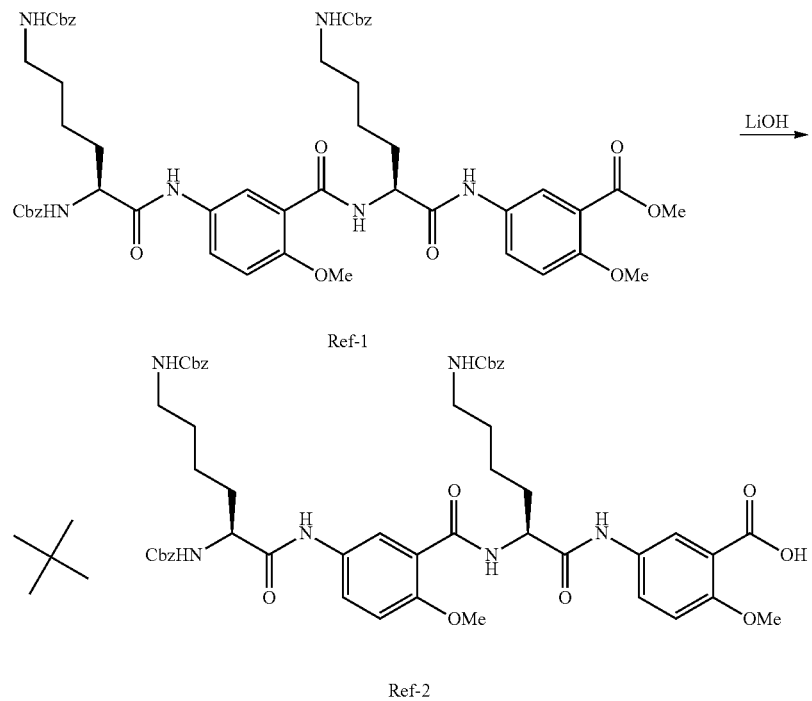

A solution of the methyl ester compound Ref-1 (0.854 g, 0.086 mmol) in a mixture of 5.1 mL of THF and 3.4 mL of methanol was treated with 1.7 mL of a 2.0 M aqueous solution of lithium hydroxide (4 equivalents) in one portion. The reaction was stirred at room temperature and became orange and clouded with precipitate within a few minutes. After 16 hours the starting material Ref-1 was found to be completely consumed by TLC, and the reaction mixture was cooled in an ice bath, treated with 3.4 mL of cold 1.0 M HCl to neutralize to the base used. The quenched mixture was partially concentrated using a rotary evaporator and the residue was extracted between dichloromethane and water. The organic phase was dried over $Na_2SO_4$, filtered, and concentrated. Obtained 0.704 g of yellow residue, which would be 83% of theoretical yield. MS/HPLC showed the mixture was 97% pure but it was not the desired product Ref-2.

MS/HPLC and $^1H$ NMR showed that no desired product Ref-2 was present in the reaction mixture. MS/HPLC also confirmed that all starting materials were consumed. Two main products were formed and isolated (M+1=885 and 899), but neither of them is the desired product Ref-2. One product of the reaction had an M+1 of 885, which corresponds to a compound that resulted from methyl ester hydrolysis and also loss of one benzyl group with $CO_2$ remaining Clearly this product of the undesired reaction was not a simple Cbz group cleavage. The other product of the reaction had an M+1 of 899, which corresponds to a compound that resulted from degradation of a Cbz group but with the methyl ester still intact. While not wishing to be bound by a particular theory, it is believed that the Cbz groups on the sidechains were not

81 affected by these conditions and that only the Cbz group on the α-amine was involved in the reaction.

Example 4

Purification

A purification procedure has been developed and successfully performed on scale under GMP controls. This process was applied to the material obtained as compound 1-12. It is generally applicable to purification of the compound of Formula I.

A sample of 120 g (0.0917 mol) of compound 1-12 was further treated with 1080 mL of methanol and 1080 mL of distilled water, agitated for at least 30 minutes at 20-25° C. to dissolve, and filtered. The flask and collected material were rinsed with 240 mL of 1:1 (volume) methanol/distilled water; the filtrates were combined and heated to a temperature of 55-60° C. The heated solution was treated with 3600 mL of n-butanol dropwise over 45 minutes while maintaining a temperature of 55-60° C. Upon completion of addition, the mixture was cooled slowly to 0-5° C. over a minimum of 3 hours. The cold temperature was maintained for a minimum of 2 hours after which the precipitate was collected by filtration and washed with 480 mL of 3:1:1 (volume) n-butanol/methanol/distilled water at 0-5° C. The solid was dried to a constant weight under nitrogen. Obtained 98.3 g of compound 1-12 as a pale tan solid with an HPLC peak area purity of 99.6%.

Having now fully described this invention, it will be understood to those of ordinary skill in the art that the same can be performed within a wide and equivalent range of conditions and other parameters without affecting the scope of the invention or any embodiment thereof. All documents, e.g., scientific publications, patents, patent applications, and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document. Various modifications of the invention, in addition to those described herein, will be apparent to those skilled in the art from the foregoing description. Such modifications are also intended to fall within the scope of the appended claims.

What is claimed is:

1. A method for preparing a compound of Formula I:

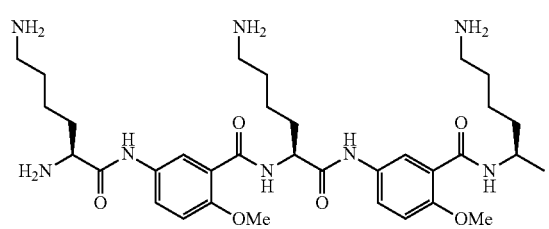

82

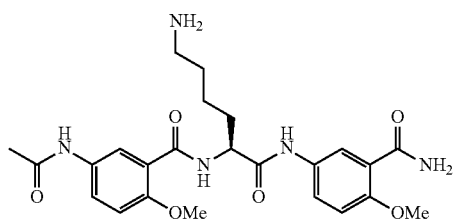

or pharmaceutically acceptable salt thereof, comprising:

a) removing the Cbz groups from a compound of Formula II:

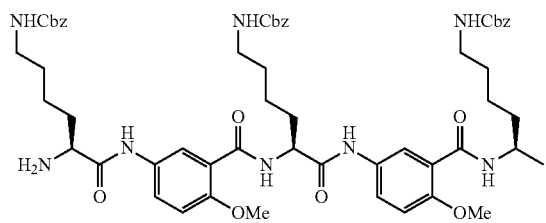

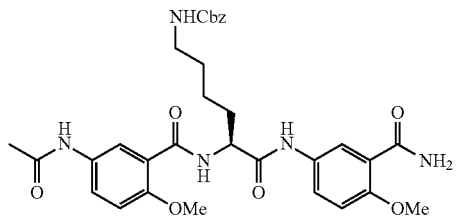

or pharmaceutically acceptable salt thereof, under a hydrogenation/hydrogenolysis condition to form the compound of Formula I, or pharmaceutically acceptable salt thereof; and b) optionally isolating the compound of Formula I, or pharmaceutically acceptable salt thereof.

2. The method of claim 1 further comprising:

c) removing the Boc group from a compound of Formula III:

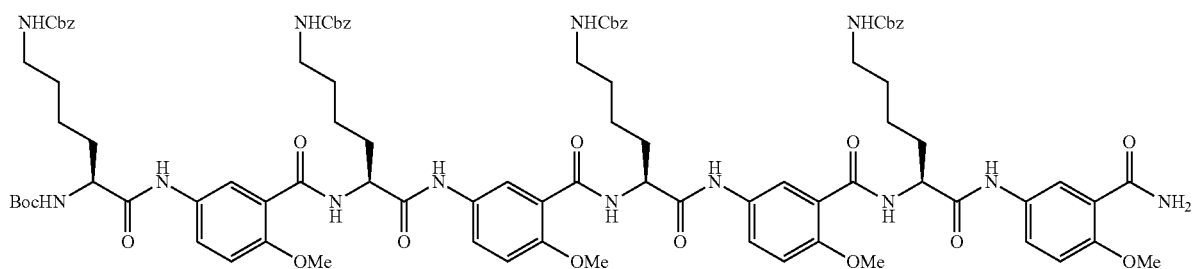

III or pharmaceutically acceptable salt thereof, in the presence of an acid to form the compound of Formula II, or pharmaceutically acceptable salt thereof.

3. The method of claim 2 further comprising:
d) reacting a compound of Formula IV:

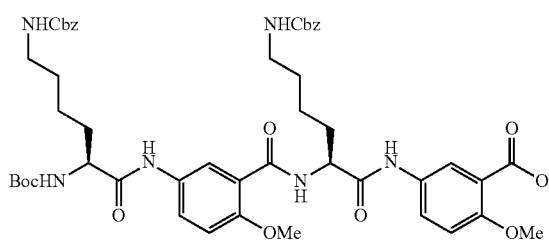

IV or pharmaceutically acceptable salt thereof, with a compound of Formula V:

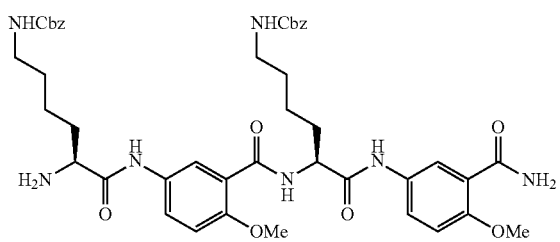

V or pharmaceutically acceptable salt thereof, in the presence of a coupling reagent and an organic base to form the compound of Formula III, or pharmaceutically acceptable salt thereof.

4. The method of claim 3 further comprising:
e) reacting a compound of Formula IV:

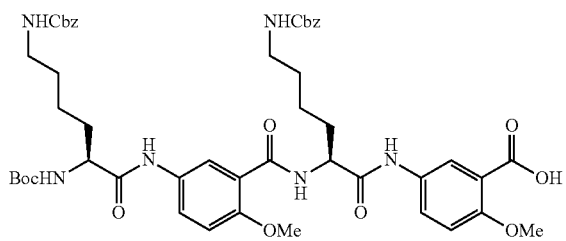

IV or pharmaceutically acceptable salt thereof, with ammonia or an ammonia producing reagent, in the presence of an activating reagent and an organic base to form a compound of Formula VI:

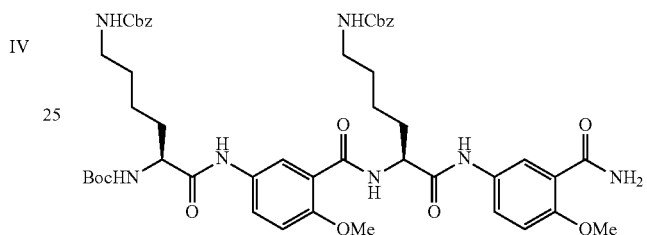

VI or pharmaceutically acceptable salt thereof; and
f) removing the Boc group from the compound of Formula VI, or pharmaceutically acceptable salt thereof, in the presence of an acid to form the compound of Formula V, or pharmaceutically acceptable salt thereof.

5. The method of claim 4 further comprising:
g) hydrolyzing a compound of Formula VII:

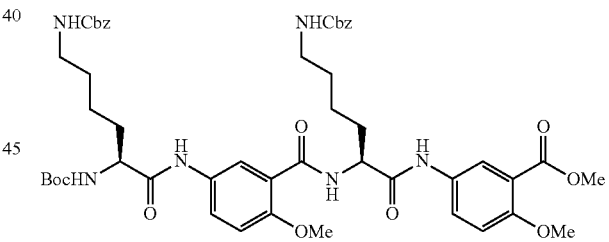

VII or pharmaceutically acceptable salt thereof, in the presence of a base to form the compound of Formula IV.

6. The method of claim 5 further comprising:
h) reacting a compound of Formula VIII:

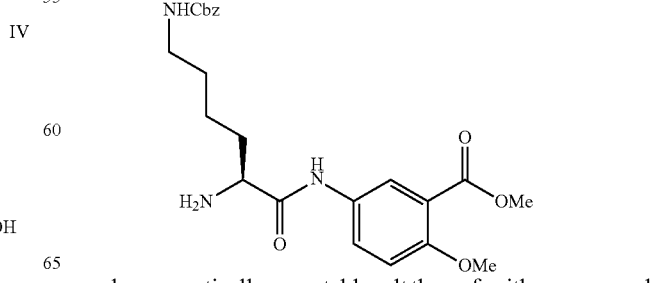

VIII or pharmaceutically acceptable salt thereof, with a compound of Formula IX:

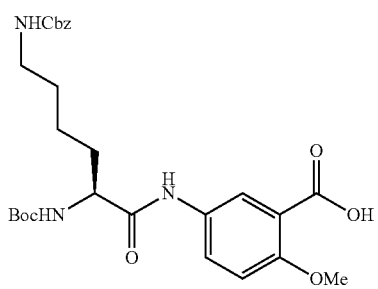

or pharmaceutically acceptable salt thereof, in the presence of a coupling reagent and an organic base to form the compound of Formula VII, or pharmaceutically acceptable salt thereof.

7. The method of claim 6 further comprising:

i) hydrolyzing a compound of Formula X:

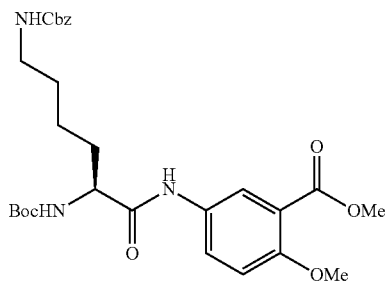

or pharmaceutically acceptable salt thereof, in the presence of a base to form the compound of Formula IX; and
j) removing the Boc group from a compound of Formula X, or pharmaceutically acceptable salt thereof, in the presence of an acid to form the compound of Formula VIII, or pharmaceutically acceptable salt thereof.

8. The method of claim 7 further comprising:

k) reacting a compound of Formula XI:

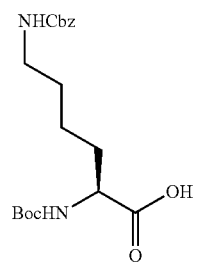

or pharmaceutically acceptable salt thereof, with a compound of Formula XII:

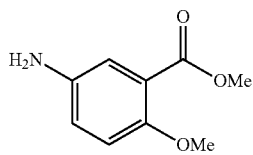

or pharmaceutically acceptable salt thereof, in the presence of a coupling reagent and an organic base to form the compound of Formula X, or pharmaceutically acceptable salt thereof.

9. A method for preparing a compound of formula I:

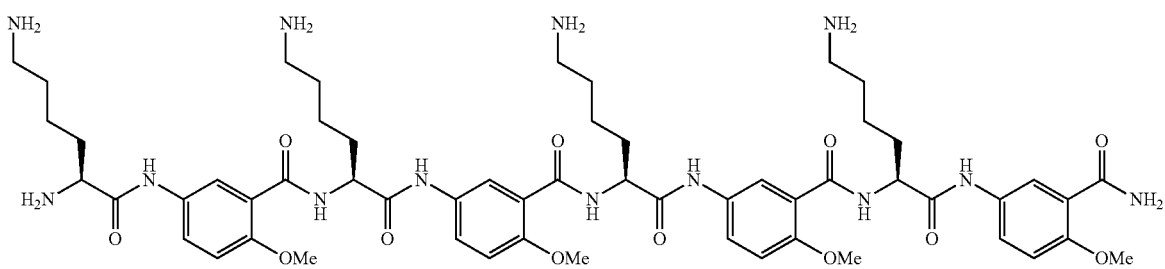

or pharmaceutically acceptable salt thereof, comprising:

a1) removing the Cbz groups from a compound of Formula II-1:

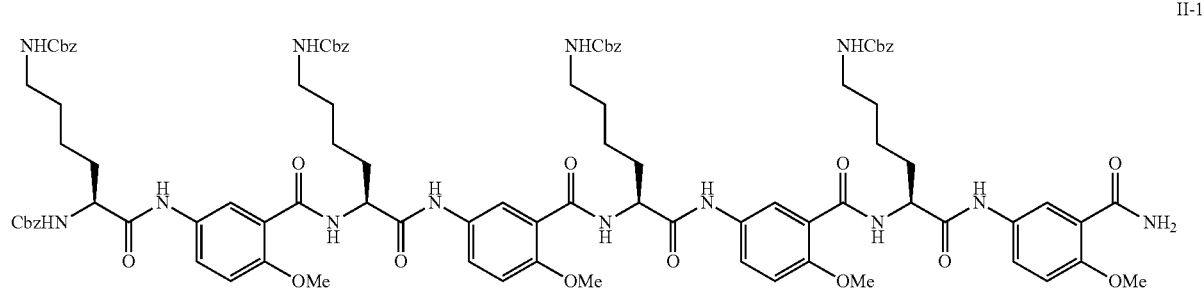 [SMILES: "II-1" ; COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)[C@H](CCCCNC(=O)OCc4ccccc4)NC(=O)c4cc(NC(=O)[C@H](CCCCNC(=O)OCc5ccccc5)NC(=O)OCc5ccccc5)ccc4OC)ccc3OC)ccc2OC)cc1C(N)=O]

II-1 or pharmaceutically acceptable salt thereof, under a hydrogenation/hydrogenolysis condition to form the compound of Formula I, or pharmaceutically acceptable salt thereof; and
b1) optionally isolating the compound of Formula I, or pharmaceutically acceptable salt thereof.
10. The method of claim 9 further comprising:
c1) reacting a compound of Formula III-1:

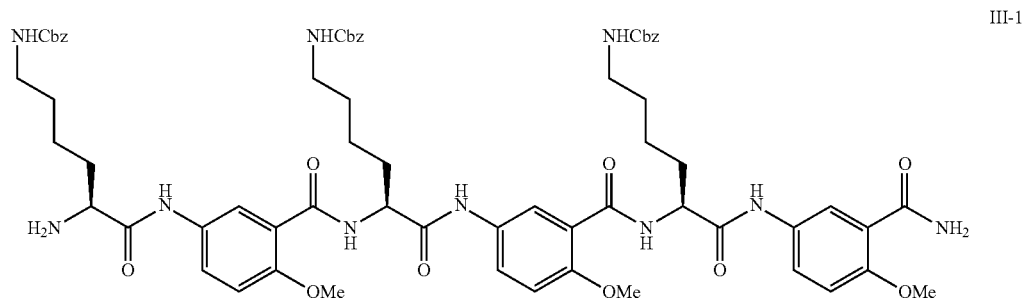 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)[C@@H](N)CCCCNC(=O)OCc4ccccc4)ccc3OC)ccc2OC)cc1C(N)=O]

III-1 or pharmaceutically acceptable salt thereof, with a compound of Formula IV-1:

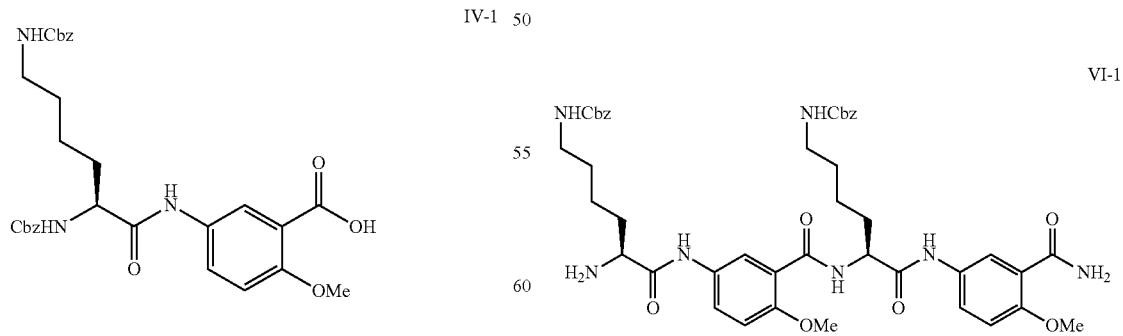

IV-1 or pharmaceutically acceptable salt thereof, in the presence of a coupling reagent and an organic base to form the compound of Formula II-1, or pharmaceutically acceptable salt thereof.

11. The method of claim 10 further comprising:

d1) reacting a compound of Formula VI-1:

VI-1 or pharmaceutically acceptable salt thereof, with a compound of Formula VII-1:

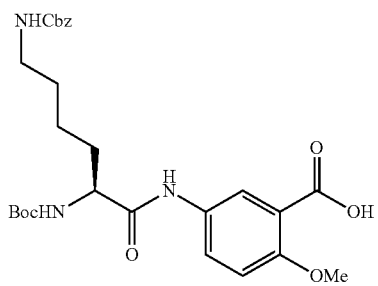

VII-1 or pharmaceutically acceptable salt thereof, in the presence of a coupling reagent and an organic base to form a compound of Formula V-1:

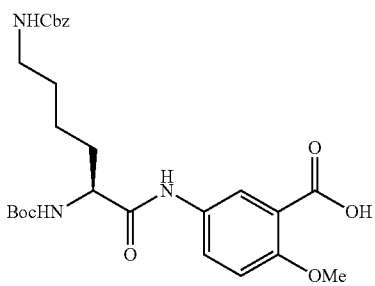

VII-1 or pharmaceutically acceptable salt thereof, in the presence of a coupling reagent and an organic base to form a compound of Formula IX-1:

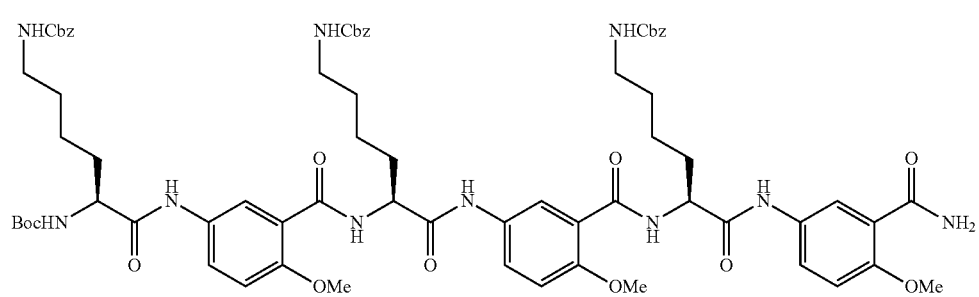

V-1 or pharmaceutically acceptable salt thereof; and e1) removing the Boc group from the compound of Formula V-1, or pharmaceutically acceptable salt thereof, in the presence of an acid to form the compound of Formula III-1, or pharmaceutically acceptable salt thereof.

12. The method of claim 10 further comprising:

f1) reacting a compound of Formula VIII-1:

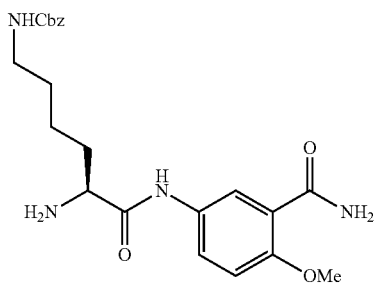

VIII-1 or pharmaceutically acceptable salt thereof, with a compound of Formula VII-1:

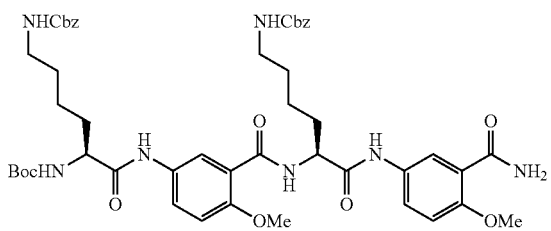

IX-1 or pharmaceutically acceptable salt thereof; and g1) removing the Boc group from the compound of Formula IX-1, or pharmaceutically acceptable salt thereof, in the presence of an acid to form the compound of Formula VI-1, or pharmaceutically acceptable salt thereof.

13. The method of claim 12 further comprising:

h1) reacting a compound of Formula XI-1:

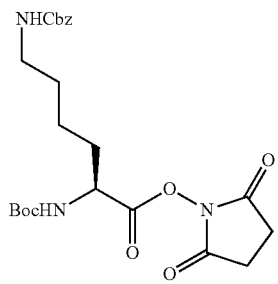

XI-1 or pharmaceutically acceptable salt thereof, with a compound of Formula XII-1:

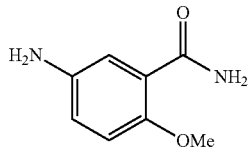

XII-1 or pharmaceutically acceptable salt thereof, optionally in the presence of an organic base to form a compound of Formula X-1:

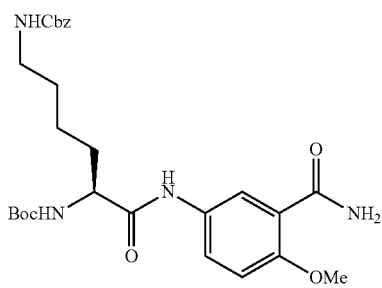

X-1 or pharmaceutically acceptable salt thereof; and i1) removing the Boc group from the compound of Formula X-1 or pharmaceutically acceptable salt thereof, in the presence of an acid to form the compound of Formula VIII-1, or pharmaceutically acceptable salt thereof.

14. The method of claim 12 further comprising:

j1) reacting a compound of Formula XI-1:

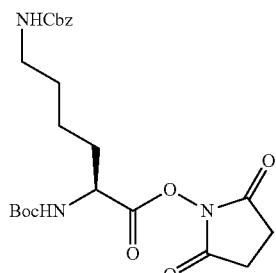

XI-1 or pharmaceutically acceptable salt thereof, with a compound of Formula XIII-1:

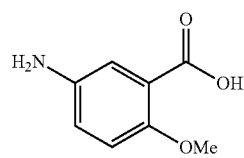

XIII-1 or pharmaceutically acceptable salt thereof, to form the compound of Formula VII-1, or pharmaceutically acceptable salt thereof.

15. The method of claim 14 further comprising:

k1) reacting a compound of Formula XIV-1:

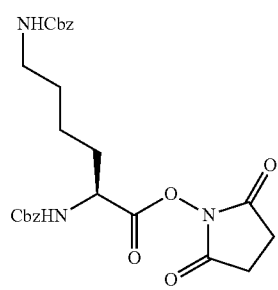

XIV-1 or pharmaceutically acceptable salt thereof, with a compound of Formula XIII-1:

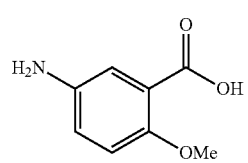

XIII-1 or pharmaceutically acceptable salt thereof, to form the compound of Formula IV-1, or pharmaceutically acceptable salt thereof.

16. The method of claim 9 further comprising:
c2) reacting a compound of Formula III-2:

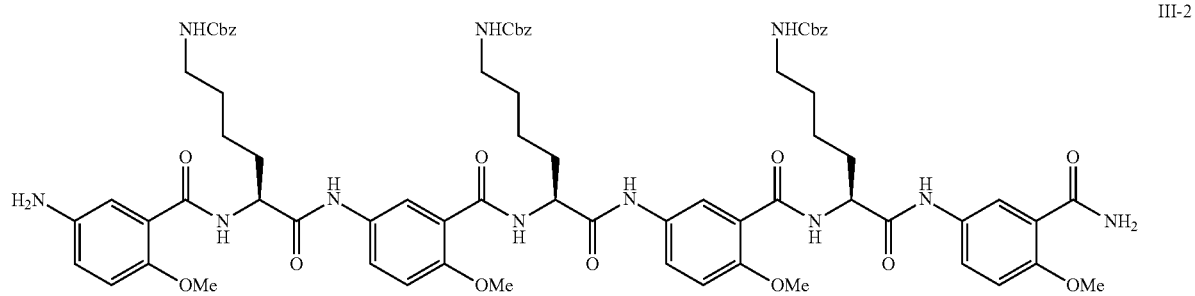 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)[C@H](CCCCNC(=O)OCc4ccccc4)NC(=O)c4cc(N)ccc4OC)ccc3OC)ccc2OC)cc1C(N)=O]

III-2 or pharmaceutically acceptable salt thereof, with a compound of Formula IV-2:

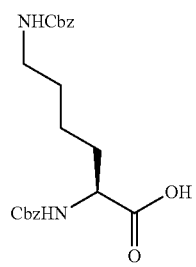

IV-2 or pharmaceutically acceptable salt thereof, in the presence of a coupling reagent and an organic base to form the compound of Formula II-1, or pharmaceutically acceptable salt thereof.

17. The method of claim 16 further comprising:

d2) removing the Boc group from a compound of Formula V-2:

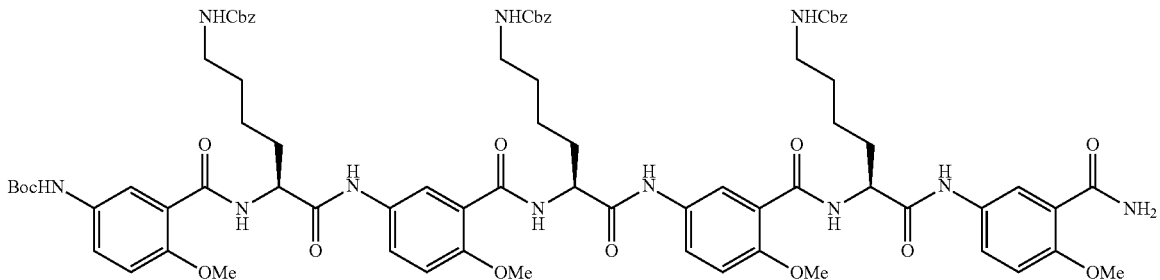

V-2 or pharmaceutically acceptable salt thereof, under an acidic condition to form the compound of Formula III-2, or pharmaceutically acceptable salt thereof.

18. The method of claim 17, further comprising:

e2) reacting a compound of Formula VI-2:

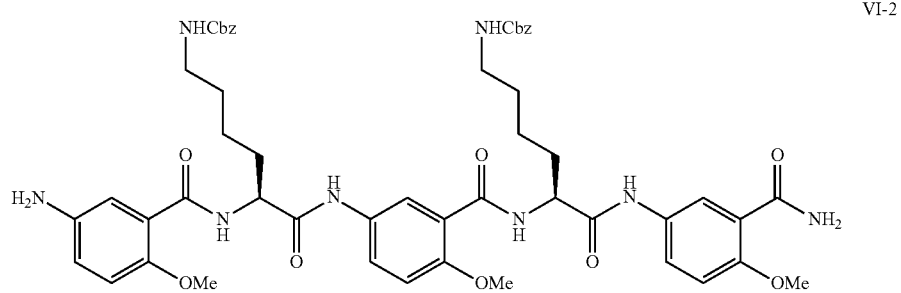 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(N)ccc3OC)ccc2OC)cc1C(N)=O]

VI-2 or pharmaceutically acceptable salt thereof, with a compound of Formula VII-2:

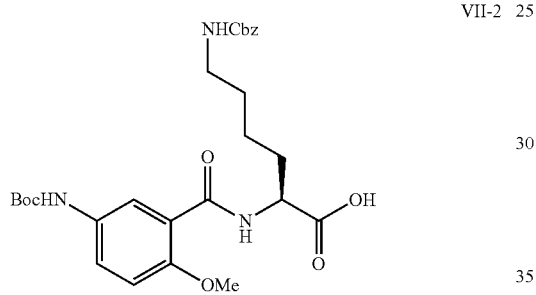

VII-2 or pharmaceutically acceptable salt thereof, in the presence of a coupling reagent and an organic base to form the compound of Formula V-2, or pharmaceutically acceptable salt thereof.

19. The method of claim 18 further comprising:

f2) removing the Boc group from a compound of Formula VIII-2:

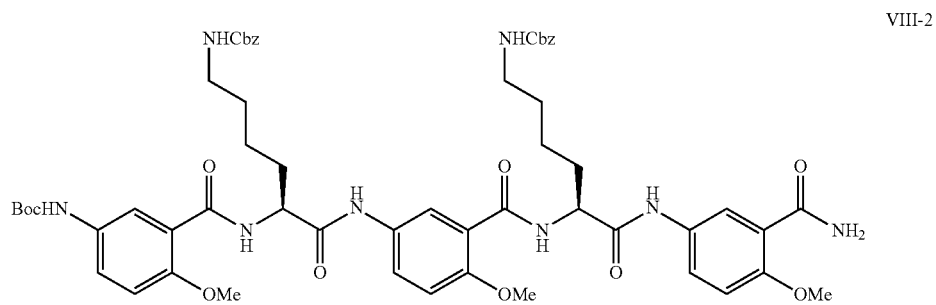 [SMILES: COc1ccc(NC(=O)[C@H](CCCCNC(=O)OCc2ccccc2)NC(=O)c2cc(NC(=O)[C@H](CCCCNC(=O)OCc3ccccc3)NC(=O)c3cc(NC(=O)OC(C)(C)C)ccc3OC)ccc2OC)cc1C(N)=O]

VIII-2 or pharmaceutically acceptable salt thereof, under an acidic condition to form the compound of Formula VI-2, or pharmaceutically acceptable salt thereof.

20. The method of claim 19 further comprising:
g2) reacting a compound of Formula IX-2:

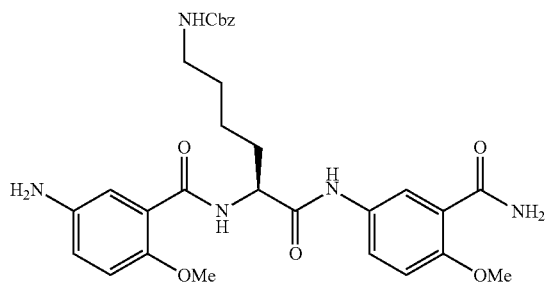

IX-2 or pharmaceutically acceptable salt thereof, with a compound of Formula VII-2:

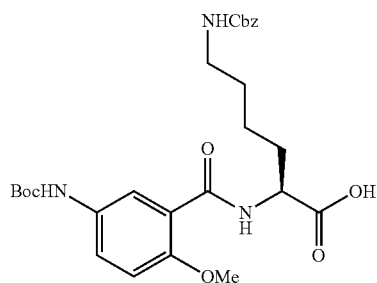

VII-2 or pharmaceutically acceptable salt thereof, in the presence of a coupling reagent and an organic base to form the compound of Formula VIII-2, or pharmaceutically acceptable salt thereof.

21. The method of claim 20 further comprising:
h2) removing the Boc group from a compound of Formula X-2:

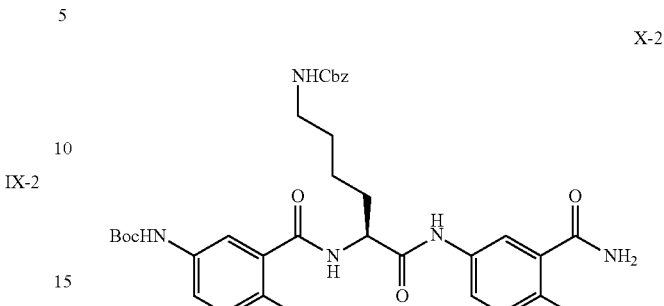

X-2 or pharmaceutically acceptable salt thereof, under an acidic condition to form the compound of Formula IX-2, or pharmaceutically acceptable salt thereof.

22. The method of claim 21 further comprising:
i2) reacting a compound of Formula VII-2:

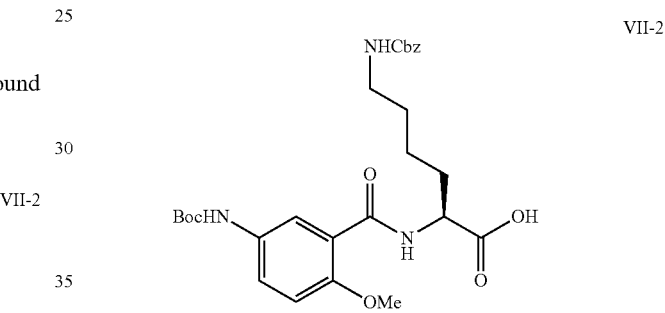

VII-2 or pharmaceutically acceptable salt thereof, with a compound of Formula XI-2:

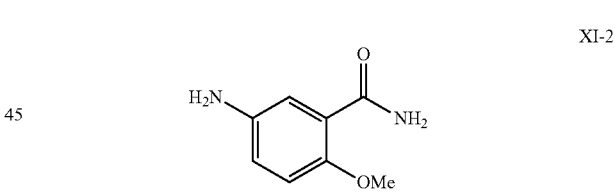

XI-2 or pharmaceutically acceptable salt thereof, in the presence of a coupling reagent and an organic base to form the compound of Formula X-2, or pharmaceutically acceptable salt thereof.

23. A compound chosen from:

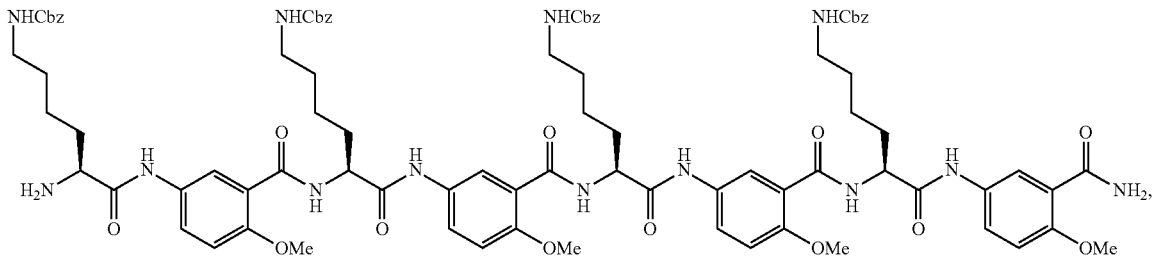

99 100
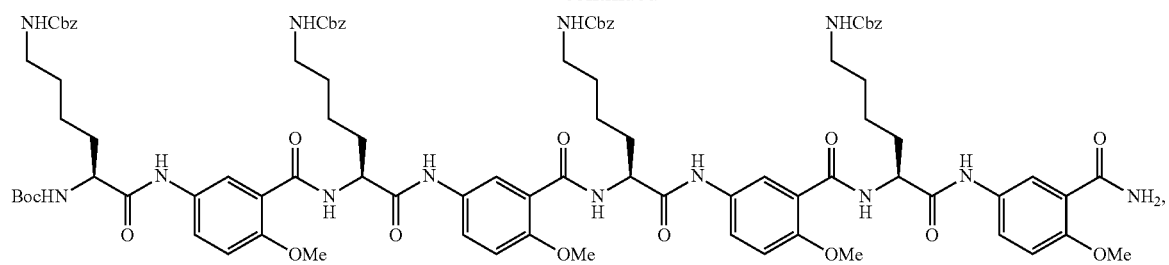
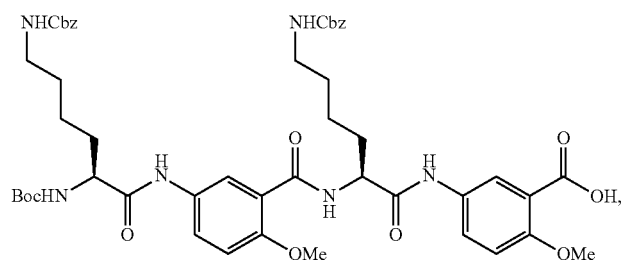
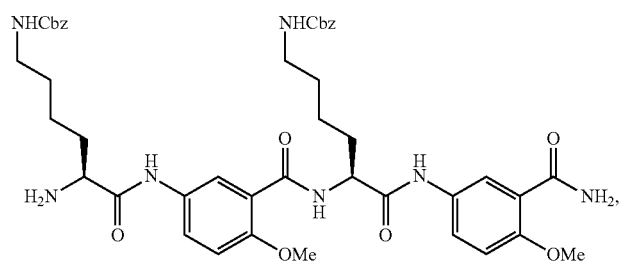
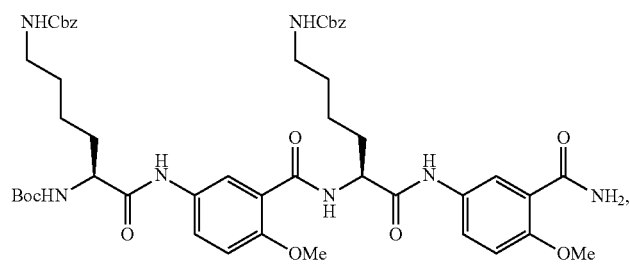
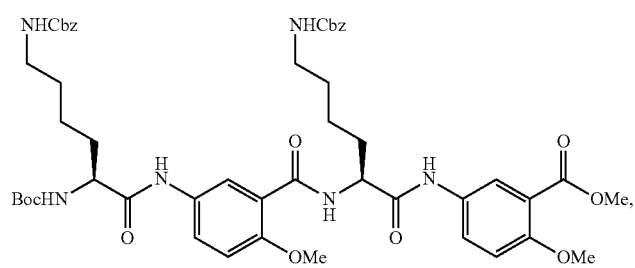
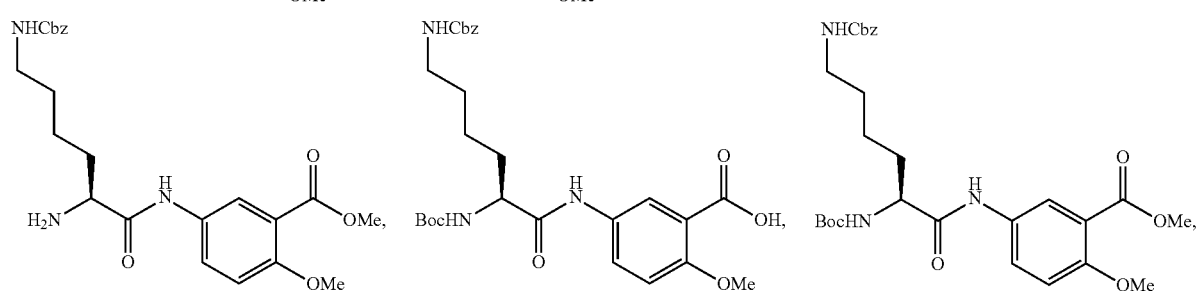

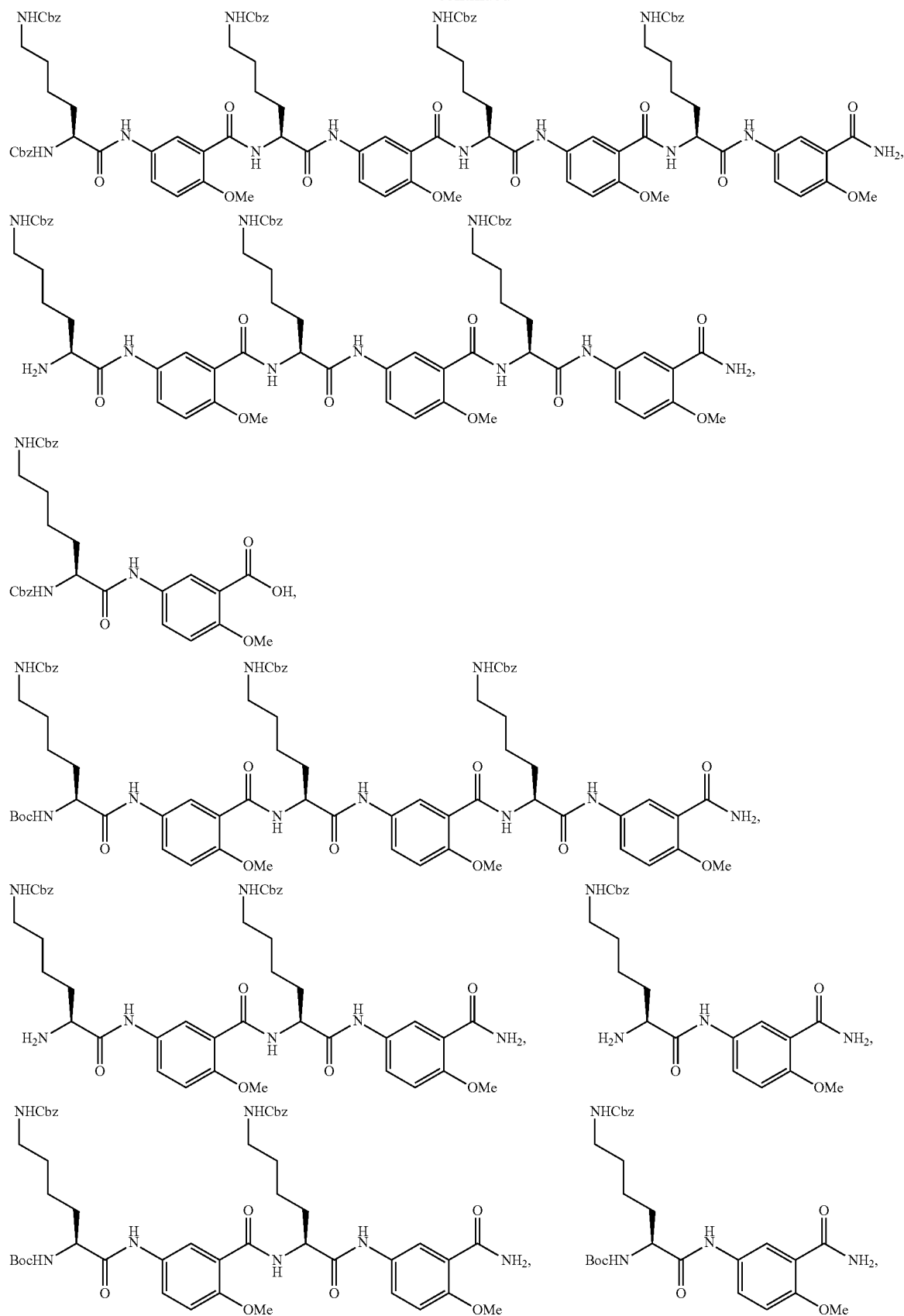

103
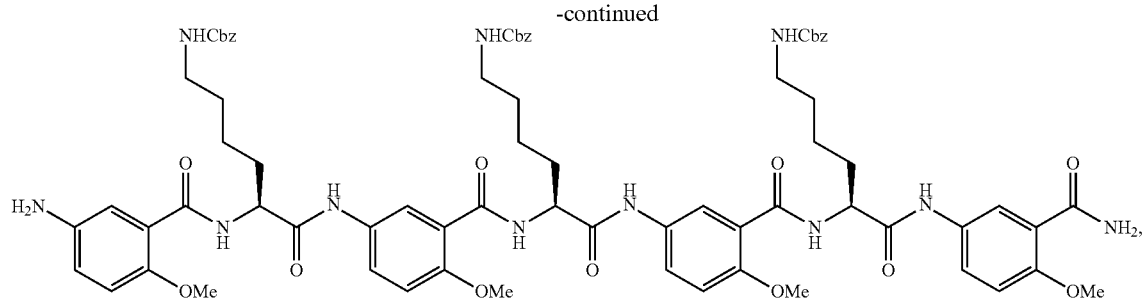
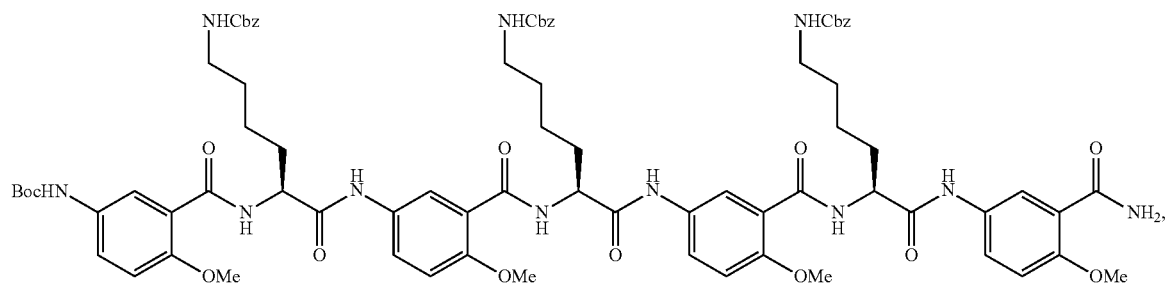
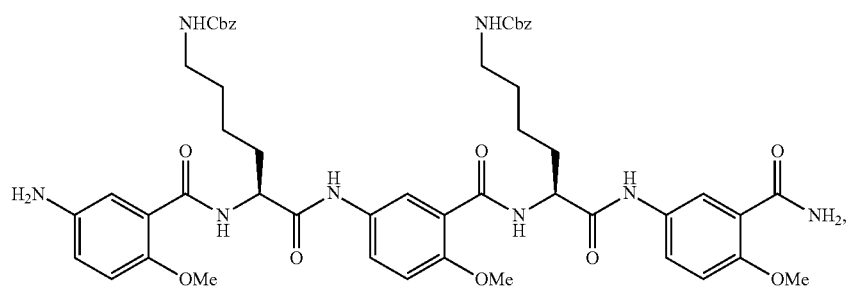
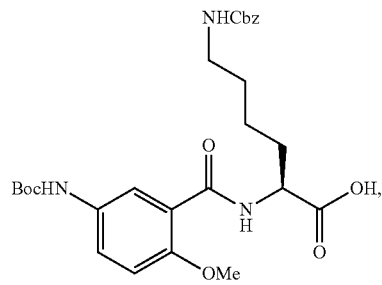
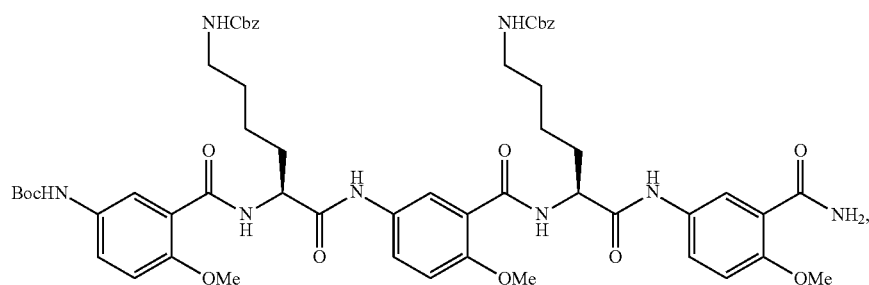

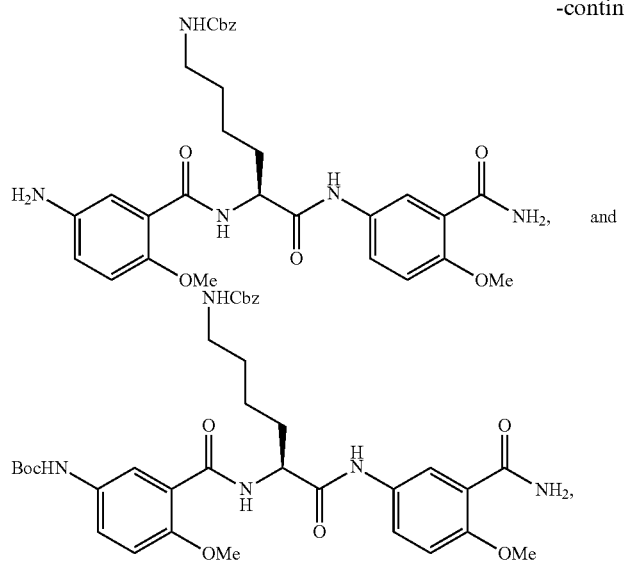
or pharmaceutically acceptable salt thereof.
* * * * *